United States Patent
Biediger et al.

(10) Patent No.: US 9,512,109 B2
(45) Date of Patent: Dec. 6, 2016

(54) AGONISTS THAT ENHANCE BINDING OF INTEGRIN-EXPRESSING CELLS TO INTEGRIN RECEPTORS

(75) Inventors: Ronald J. Biediger, Houston, TX (US); William C. Gundlach, IV, Houston, TX (US); Robert V. Market, Houston, TX (US); Michael M. Savage, Houston, TX (US); Peter Vanderslice, Houston, TX (US)

(73) Assignee: TEXAS HEART INSTITUTE, Houston, TX (US)

( * ) Notice: Subject to any disclaimer, the term of this patent is extended or adjusted under 35 U.S.C. 154(b) by 485 days.

(21) Appl. No.: 13/885,537

(22) PCT Filed: Nov. 16, 2011

(86) PCT No.: PCT/US2011/060996
§ 371 (c)(1),
(2), (4) Date: May 15, 2013

(87) PCT Pub. No.: WO2012/068251
PCT Pub. Date: May 24, 2012

(65) Prior Publication Data
US 2013/0236434 A1    Sep. 12, 2013

Related U.S. Application Data

(60) Provisional application No. 61/414,271, filed on Nov. 16, 2010.

(51) Int. Cl.
| | |
|---|---|
| C07D 333/20 | (2006.01) |
| C07D 409/14 | (2006.01) |
| C07D 275/02 | (2006.01) |
| A61K 47/48 | (2006.01) |
| C07C 271/20 | (2006.01) |
| C07C 311/08 | (2006.01) |
| C07D 213/64 | (2006.01) |
| C07D 317/60 | (2006.01) |
| A61K 35/17 | (2015.01) |
| A61K 35/51 | (2015.01) |
| C07D 333/10 | (2006.01) |
| C07D 409/12 | (2006.01) |
| C07D 413/14 | (2006.01) |
| A61K 35/12 | (2015.01) |
| C07C 229/34 | (2006.01) |
| C07C 271/22 | (2006.01) |
| C07D 333/24 | (2006.01) |

(52) U.S. Cl.
CPC ............ *C07D 409/14* (2013.01); *A61K 35/12* (2013.01); *A61K 35/17* (2013.01); *A61K 35/51* (2013.01); *A61K 47/481* (2013.01); *C07C 229/34* (2013.01); *C07C 271/20* (2013.01); *C07C 271/22* (2013.01); *C07C 311/08* (2013.01); *C07D 213/64* (2013.01); *C07D 275/02* (2013.01); *C07D 317/60* (2013.01); *C07D 333/10* (2013.01); *C07D 333/20* (2013.01); *C07D 333/24* (2013.01); *C07D 409/12* (2013.01); *C07D 413/14* (2013.01)

(58) Field of Classification Search
CPC .......................... C07D 333/10; C07D 333/20
USPC .......................................................... 549/41
See application file for complete search history.

(56) References Cited

U.S. PATENT DOCUMENTS

| | | | |
|---|---|---|---|
| 5,142,048 A | 8/1992 | Hemmi | |
| 5,250,517 A | 10/1993 | Branca | |
| 7,452,904 B2 | 11/2008 | Catena Ruiz et al. | |
| 2005/0222193 A1 | 10/2005 | Hanauer et al. | |
| 2010/0168468 A1 | 7/2010 | Tsunenaga et al. | |

FOREIGN PATENT DOCUMENTS

| | | |
|---|---|---|
| CA | 2021740 | 1/1991 |
| CA | 1331564 | 12/1998 |
| CA | 2325741 | 7/1999 |
| CA | 2397831 | 8/2001 |
| WO | WO 9208694 | 5/1992 |
| WO | WO 9952898 | 10/1999 |

OTHER PUBLICATIONS

Pop et al. Redox targeting of LY231617, an antioxidant with potential use in the treatment of brain damage. Int. J. Pharm. 140, pp. 33-44 (1996).*

STN entry for CAS RN 733783-15-8 (STN entry date Aug. 27, 2004).*

Viswajanani J Sattigeri et al; Synthesis and Biological Evaluation of Ureido Derivatives as VLA-4 Antagonists; Indian Journal of Chemistry; vol. 45B, Nov. 2006, pp. 2534-2541; Jun. 2, 2005; accepted (revised) Oct. 13, 2006.

Dramane I. Laine et al; Discovery of Novel 8-Azoniabicyclo(3.2.1.)octane Carbamates; as Muscarinic Acetylcholine Receptor Antagonists; Available online Sep. 25, 2007.

Sham S. Nikam et al; NovelQuenchers for Solution Phase Parallel Synthesis; Tetrahedron Letters 39, (1998) 1121-1124; Dec. 2, 1997.

T Benneche, et al; Pyrimidinones as Reversible Metaphase Arresting Agents; Eur J Med Chem (1993) 28, 463-472; (Aug. 31, 1992; accepted Dec. 15, 1992).

(Continued)

*Primary Examiner* — Barbara P Badio
*Assistant Examiner* — Sara E Townsley
(74) *Attorney, Agent, or Firm* — Conley Rose, P.C.

(57) ABSTRACT

A method of enhancing binding of cells to an integrin-binding ligand comprises treating integrin-expressing cells in vitro with an agonist of integrin, wherein the integrin is selected from the group consisting of α4β1, α5β1, α4β7, αvβ3 and αLβ2, and contacting the treated cells with an integrin-binding ligand; integrin agonist compounds having the general formula I; methods of treating integrin-expressing cells with such agonists to enhance binding; and therapeutic methods comprising administering agonist-treated cells or agonist compounds to a mammal.

1 Claim, No Drawings

(56) References Cited

OTHER PUBLICATIONS

Ralph Nicholas Salvatore, et al; An effiecient one-pot Synthesis of N-alkyl carbamates from Primary Amines using Cs2CO3; Department of Chemistry, University of South Florida; Tetrahedron Letters 42 (2001) 6023-6025.
Mari Antonietta Casadei, et al; Electrogenerated Superoxide-Activated Carbon Dioxide, A new Mild and Safe approach to Organic Carbamtes; J. Org. Chem 1997, 62, 6754-6759.
Raines, et al; Synthesis and Pharmacology of a Series of Substituted 2-Aminomethylpyrroles; The national Drug drug Company, Research Laboratories; Journal of Medicinal Chemistry, 1970, vol. 13,No. 6.
T Benneche, et al; Pyrimidinones as Reversible Metaphase Arresting Agents; department of Chemistry, (1993) 28, 463-472.
Stark et al; Novel Carbamates as Poteny Histamine H3 Receptor Antagonists with High in Vitro and Orall in Vivo Activity; J med. Chem. 1996, 39, 1157-1163.
Okubo, et al; Design, Synthesis and Structure-Affinity Relationships of Aryloxynilide Derivatives as Novel Peripheral Benzodiazepine Receptor Ligands; Bioorganic & Medicinal Chemistry 12 (2004) 423-438.
Wei Yang, e al; A Small Molecule Agonist of an Integrin Lb2; J. Biol. Chem. 2006, 281: 37904-37912.
A. Perdih, et al; Small Molecule Antagonists of Integrin Receptors; Current Medicinal Chemistry, 2010, 17, 2371-2392.
Faridi, et al: Identification of Novel Agonists of the Integrin CD11b/CD18; Bioorganic & Medicinal Chemistry Letters 19 (2009), 6902-6906.
Bjorklund, et al. Stabilization of the Activated amb2 Integrin by a Small Molecule Inhibits Leukocyte Migration and Recruitment; Biochemistry 2006, 45, 4862-2871; Revised Manuscript Received Jan. 12, 2006.
Partial European Search Report dated May 4, 2015 for EP Application No. 14191380 (6 pages).
Extended European Search Report dated May 12, 2015 for EP Application No. 14191380.6 (1 page).
Office Action dated Jul. 9, 2015 for Canadian Application 2818336 (4 pages).
Extended European Search Report dated Mar. 3, 2014 for EP 11841201.4 (10 pages).
Masui Y et al: "One-pot synthesis N-acyl-substituted sulfamides from chlorosulfonyl isocyanate via the Burgess-type intermediates". Tetrahedron Letters. Pergamon. GB. vol. 45. No. 9. Feb. 23, 2004. pp. 1853-1856. (4 pages).
Pretsch E et al: II Ionophores of the Type 1 of 3-Oxapentane Oiamides, Helvetica Chimica Acta, Verlag Helvetica Chimica Acta, CH, vol. 63, No. I, 23 Jan. 1980, pp. 191-196 (6 pages).
Faridi Mohd H et al: "Identification of novel agonists of the integrin CDIIb/CDI8" • Bioorganic & Medicinal Chemistry Letters. Pergamon. Amsterdam. NL vol. 19. No. 24. Dec. 15, 2009, pp. 6902-6906 (5 pages).
Vanderslice et al: "Small Molecule Agonist of Very Late Antigen-4 (VLA-4) Integrin Induces Progenitor Cell Adhesion". Ournal of Biological Chemistr, vol. 288. No. 27. May 23, 2013, pp. 19414-19428 (16 pages).
Zigeuner et al: "Studien auf dem Gebiet der Hamstoff-Formaldehyd. Kondensation* xv. Mitteilung: Uber Hydroxybenzylurone". Monatshefte Fur Chemie. vol. 87. No. 3, Jan. 1, 1956, pp. 406-420 (15 pages).
Abdaoui, Mohamed et al: "A New Family of 1 Potential Oncostatics: 2-Chloroethylnitrososulfamides (CENS)—1. Synthesis. Structure. and Pharmacological Evaluation (Preliminary Results)". Bioorganic & Medicinal Chemistry.vol. 4. No. 8. Jan. 1, 1996, pp. 1227-1235 (9 pages).
Ulhrich K et al: "Synthesis of dendritic polyamides via a convergent growth approach". Journal of the Chemical Society. Perkin Transactions 1. vol. 1. No. 13, Jan. 1, 1992 p. 1623-1630 (8 pages).
Salvatore, R., et al., Efficient and selective N-alkylation of carbamates in presences of CS2CO3 and TBAI (3 pages).
PCT/US2011/060996 International Search Report and Written Opinion dated May 22, 2012 (11 pgs.).

* cited by examiner

AGONISTS THAT ENHANCE BINDING OF INTEGRIN-EXPRESSING CELLS TO INTEGRIN RECEPTORS

BACKGROUND

1. Technical Field

The present disclosure generally relates to N,N-disubstituted amide, carbamate, urea and sulfonamide compounds and to their use as integrin agonists for enhancing binding of integrin-expressing cells to integrin-binding ligands or receptors.

2. Description of Related Art

Many human diseases are characterized by severe tissue damage which leads to faulty or decreased organ function. Cell-based therapies using stem cells or progenitor cells have shown promise in improving functional outcomes and regenerating tissue. These positive effects appear to be the result of differentiation of the injected cells into the relevant cell type and/or by release of paracrine factors that stimulate restoration of host tissue. The cells usually considered for use in these procedures are embryonic stem cells, adult stem/progenitor cells, or induced pluripotent stem cells. The cells are typically injected intravenously or directly into, or around, the damaged tissue. Regardless of the cell type, mechanism of action, or how they are delivered, it is critical that the cells home to, and are retained in, the relevant injured tissue. Low levels of cell retention observed in animal models and clinical trials are considered one of the major impediments to the progress of cell-based therapy. Even when cells are injected locally, less than 10% of injected cells are typically retained after one hour and this number decreases over time. The retention rates are even lower when delivered systemically. Methods that increase the rate of retention of exogenously delivered cells would greatly further efforts in regenerative medicine.

The process by which cells adhere to tissues is mediated by adhesion molecules expressed on the cell surface. These adhesion molecules bind to their respective ligands on the cells and extracellular matrix that comprise the tissue. One of the predominant classes of adhesion molecules that mediate these interactions are a family of cell surface receptors called integrins. The integrins are heterodimeric proteins comprised of an α and a β subunit. At present, 18α subunits and 8β subunits have been identified that combine to form no less than 24 distinct integrin receptor pairs each with its own ligand specificity. Ligands recognized by integrins include extracellular matrix molecules (e.g., fibronectin, vitronectin, laminin, collagen) and members of the immunoglobulin supergene family (e.g. vascular cell adhesion molecule (VCAM)-1, intracellular adhesion molecule (ICAM)-1, mucosal addressin cell adhesion molecule (MAdCAM)-1). As cell adhesion receptors, integrins are not only involved in cellular homing, but also cell migration, proliferation, and survival.

In animal models of ischemic disease, pretreatment of progenitor cells with antibodies or other biologics that can activate integrins have been shown to increase cell incorporation into the relevant tissue and improve neovascularization (Chavakis, E., et al. 2005. Role of beta2-integrins for homing and neovascularization capacity of endothelial progenitor cells. *J Exp Med* 201:63-72; and Chavakis, E., A., et al. 2007. High-mobility group box 1 activates integrin-dependent homing of endothelial progenitor cells. *Circ Res* 100:204-212). There is continuing interest in integrin-mediated adhesion and in its potential therapeutic applications.

SUMMARY

In accordance with some embodiments of the invention, chemical compounds are disclosed that can enhance the integrin-mediated binding of cells to their respective ligands. In various embodiments, integrins targeted by these compounds include, but are not limited to, α4β1, α4β7, α5β1, αLβ2 and αVβ3. In various embodiments, ligands include, but are not limited to, VCAM-1, fibronectin, MAdCAM-1, ICAM-1, ICAM-2, and vitronectin.

In some embodiments, a chemical compound is provided having the general formula (I)

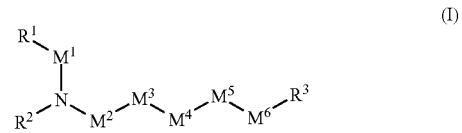

wherein
$R^1$ is selected from the group consisting of aryl and aralkyl,
$R^2$ is alkyl, aryl, or aralkyl,
$M^1$ is $CH_2$,
$M^2$ is CO,
$M^3$ is O, S, or $NR^6$, wherein
$R^6$ when present is hydrogen or lower alkyl,
$M^4$ is absent or $CH_2$,
$M^5$ is $(CR^{11}R^{12})$, wherein
$R^{11}$ is hydrogen,
$R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $O(CH_2CH_2O)_sR^{24}$, $COOR^{24}$, alkyl, and hydroxyalkyl, wherein s is an integer of 1 to 6,
$R^{21}$ and $R^{22}$ when present are independently selected from the group consisting of hydrogen or lower alkyl,
$R^{23}$ when present is selected from the group consisting of hydroxyalkyl, alkoxyalkyl, alkyl, aryl, aralkyl and alkoxycarbonylalkyl,
provided that when $M^3$ is $NR^6$, $M^4$ is absent, and $R^{12}$ is $CONR^{22}R^{23}$, then $R^{23}$ is not 1-(1,3-benzodioxol-5-yl)-3-ethoxy-3-oxopropyl,
$R^{24}$ when present is selected from the group consisting of alkyl, aryl, aralkyl, heterocyclyl, cycloalkyl, cycloalkylalkyl, and heterocyclylalkyl,
$M^6$ is $(CH_2)_q$, wherein q is an integer from 0 to 6,
$R^3$ is selected from the group consisting of hydrogen, $CONR^{13}R^{14}$, $NR^{15}COOR^{16}$, $NR^{15}COR^{16}$, $NR^{15}CONR^{13}R^{14}$, $NR^{15}SO_2R^{16}$, $OCOR^{16}$, $COOR^{16}$, $OR^{16}$, $SR^{16}$, heterocyclyl, hydroxyl, hydroxyalkyl, guanadino, alkyl and aryl, wherein
$R^{13}$ and $R^{15}$ when present are independently hydrogen or lower alkyl,
$R^{14}$ and $R^{16}$ when present are independently selected from the group consisting of hydrogen, alkyl, aryl, aralkyl, cycloalkyl, heterocyclyl, cycloalkylalkyl, and heterocyclylalkyl,
$R^1$, $R^2$, $R^3$, $R^{12}$, $R^{14}$, $R^{16}$, $R^{23}$ and $R^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), and —OCO(dialkylamino).

In some embodiments, the compound is selected from the group consisting of methyl(6S,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl(6S,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl (6S,10S)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; methyl(6S,10S)-10-(1,3-benzodioxol-5-yl)-6-butyl-9-methyl-3,8-dioxo-1-(2-thienyl)-2-(2-thienyl)-2-(2-thienylmethyl)-4-oxa-2,7,9-triazadodecan-12-oate; ethyl(6S,10R)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; methyl (10S)-10-(1,3-benzodioxol-5-yl)-3,8-dioxo-1-(2-thienyl)-2-(2-thienylmethyl)-4-oxa-2,7,9-triazadodecan-12-oate; methyl 3,8-dioxo-1-(2-thienyl)-2-(2-thienylmethyl)-4-oxa-2,7,9-triazadodecan-12-oate; methyl(6S,10S)-10-(1,3-benzodioxol-5-yl)-6-butyl-2-methyl-3,8-dioxo-1-(2-thienyl)-4-oxa-2,7,9-triazadodecan-12-oate; methyl(6S)-6-butyl-3,8-dioxo-1-(2-thienyl)-2-(2-thienylmethyl)-4-oxa-2,7,9-triazadodecan-12-oate; (2S)-2-{[(1,3-benzodioxol-5-ylmethyl)carbamoyl]amino}hexyl bis(2-thienylmethyl)carbamate; methyl(6S,10S)-6-butyl-3,8-dioxo-10-phenyl-1-(2-thienyl)-2-(2-thienylmethyl)-4-oxa-2,7,9-triazadodecan-12-oate; (2S)-2-({[(1S)-1-(1,3-benzodioxol-5-yl)-3-hydroxypropyl]carbamoyl}amino)hexyl bis(2-thienylmethyl)carbamate; (2S)-2-[(benzylcarbamoyl)amino]hexyl bis(2-thienylmethyl)carbamate; (2S)-2-[(morpholin-4-ylcarbonyl)amino]hexyl bis(2-thienylmethyl)carbamate; (2S)-2-{[(3-methoxypropyl)carbamoyl]amino}hexyl bis(2-thienylmethyl)carbamate; (2S)-2-{[(2-methoxyethyl)carbamoyl]amino}hexyl bis(2-thienylmethyl)carbamate; tert-butyl[(2S)-1-{[bis(2-thienylmethyl)carbamoyl]oxy}hexan-2-yl]carbamate; (2S)-2-[(tert-butylcarbamoyl)amino]hexyl bis(2-thienylmethyl)carbamate; (2S)-2-[(isopropylcarbamoyl)amino]hexyl bis(2-thienylmethyl)carbamate; (2S)-2-[(methylcarbamoyl)amino]hexyl bis(2-thienylmethyl)carbamate; tert-butyl[(2R)-1-{[bis(2-thienylmethyl)carbamoyl]oxy}hexan-2-yl]carbamate; benzyl{(5S)-6-{[bis(2-thienylmethyl)carbamoyl]oxy}-5-[(tert-butoxycarbonyl)amino]hexyl}carbamate; methyl(9S,13S)-13-(1,3-benzodioxol-5-yl)-9-({[bis(2-thienylmethyl)carbamoyl]oxy}methyl)-3,11-dioxo-1-phenyl-2-oxa-4,10,12-triazapentadecan-15-oate; (2S)-2-acetamidohexyl bis(2-thienylmethyl)carbamate; methyl(3R)-3-(1,3-benzodioxol-5-yl)-3-{[(2S)-2-{[bis(2-thienylmethyl)carbamoyl]amino}hexanoyl]amino}propanoate; methyl(3R)-3-(1,3-benzodioxol-5-yl)-3-{[(2R)-2-{[bis(2-thienylmethyl)carbamoyl]amino}hexanoyl]amino}propanoate; methyl(3S)-3-(1,3-benzodioxol-5-yl)-3-{[(2R)-2-{[bis(2-thienylmethyl)carbamoyl]amino}hexanoyl]amino}propanoate; methyl(6R,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl(6R,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl(2S)-2-{[bis(2-thienylmethyl)-carbamoyl]amino}hexanoate; methyl(2R)-2-{[bis(2-thienylmethyl)carbamoyl]amino}hexanoate; 3-[(2S)-1-hydroxyhexan-2-yl]-1,1-bis(2-thienylmethyl) urea; 3-[(2R)-1-hydroxyhexan-2-yl]-1,1-bis(2-thienylmethyl)urea; methyl(2S)-6-{[(benzyloxy)carbonyl]amino}-2-{[bis(2-thienylmethyl)carbamoyl]amino}hexanoate; methyl{[bis(2-thienylmethyl)carbamoyl](methyl) amino}acetate; methyl{[bis(2-thienylmethyl)carbamoyl] amino}acetate; methyl{[bis(2-thienylmethyl)carbamoyl] (butyl)amino}acetate; 3-(3-hydroxypropyl)-1,1-bis(2-thienylmethyl)urea; methyl(2R)-{[bis(2-thienylmethyl)carbamoyl]amino}(phenyl)acetate; tert-butyl{[bis(2-thienylmethyl)carbamoyl]amino}acetate; tert-butyl{[bis(2-thienylmethyl)carbamoyl](butyl)amino}acetate; benzyl {(5S)-6-{[bis(4-methoxybenzyl)carbamoyl]oxy}-5-[(tert-butoxycarbonyl)amino]hexyl}carbamate; tert-butyl[(2S)-1-{[bis(4-methoxybenzyl)carbamoyl]oxy}hexan-2-yl]carbamate; methyl(6S,10S)-10-(1,3-benzodioxol-5-yl)-6-butyl-2-(4-methoxybenzyl)-1-(4-methoxyphenyl)-3,8-dioxo-4-oxa-2,7,9-triazadodecan-12-oate; (2S)-2-({[(1S)-1-(1,3-benzodioxol-5-yl)-3-hydroxypropyl]carbamoyl}amino)hexyl bis(4-methoxybenzyl)carbamate; (2S)-2-[(tert-butoxycarbonyl)amino]hexyl dibenzylcarbamate; methyl(6S,10S)-10-(1,3-benzodioxol-5-yl)-2-benzyl-6-butyl-3,8-dioxo-1-phenyl-4-oxa-2,7,9-triazadodecan-12-oate; tert-butyl[(2S)-1-{[bis(4-methylbenzyl)carbamoyl]oxy}hexan-2-yl]carbamate; methyl(6S,10S)-10-(1,3-benzodioxol-5-yl)-6-butyl-2-(4-methylbenzyl)-1-(4-methylphenyl)-3,8-dioxo-4-oxa-2,7,9-triazadodecan-12-oate; tert-butyl[(2S)-1-{[bis(4-chlorobenzyl)carbamoyl]oxy}hexan-2-yl]carbamate; methyl(6S,10S)-10-(1,3-benzodioxol-5-yl)-6-butyl-2-(4-chlorobenzyl)-1-(4-chlorophenyl)-3,8-dioxo-4-oxa-2,7,9-triazadodecan-12-oate; (2S)-2-[(tert-butoxycarbonyl)amino]hexyl(4-bromobenzyl)(2-thienylmethyl)carbamate; methyl(6S,10S)-10-(1,3-benzodioxol-5-yl)-2-(4-bromobenzyl)-6-butyl-3,8-dioxo-1-(2-thienyl)-4-oxa-2,7,9-triazadodecan-12-oate; methyl(6S,10S)-2-(4-azidoobenzyl)-10-(1,3-benzodioxol-5-yl)-6-butyl-3,8-dioxo-1-(2-thienyl)-4-oxa-2,7,9-triazadodecan-12-oate; (2S)-2-[(tert-butoxycarbonyl)amino]hexyl phenyl(2-thienylmethyl)carbamate; methyl(6S,10S)-10-(1,3-benzodioxol-5-yl)-6-butyl-3,8-dioxo-2-phenyl-1-(2-thienyl)-4-oxa-2,7,9-triazadodecan-12-oate; tert-butyl[(2S)-1-{[bis(3-thienylmethyl)carbamoyl]oxy}hexan-2-yl]carbamate; methyl(6S,10S)-10-(1,3-benzodioxol-5-yl)-6-butyl-3,8-dioxo-1-(3-thienyl)-2-(3-thienylmethyl)-4-oxa-2,7,9-triazadodecan-12-oate; benzyl[(5S)-5-[(tert-butoxycarbonyl)amino]-6-{[butyl(2-thienylmethyl)carbamoyl]oxy}hexyl] carbamate; (2S)-2-[(tert-butoxycarbonyl)amino]hexyl butyl (2-thienylmethyl)carbamate; methyl(3S,7S)-3-(1,3-benzodioxol-5-yl)-7-butyl-5,10-dioxo-11-(2-thienylmethyl)-9-oxa-4,6,11-triazapentadecan-1-oate; benzyl[(5S)-5-[(tert-butoxycarbonyl)amino]-6-{[(2-methoxyethyl)(2-thienylmethyl)carbamoyl]oxy}hexyl]carbamate; (2S)-2-[(tert-butoxycarbonyl)amino]hexyl(2-methoxyethyl)(2-thienylmethyl)carbamate; methyl(9S,13S)-13-(1,3-benzodioxol-5-yl)-9-butyl-6,11-dioxo-5-(2-thienylmethyl)-2,7-dioxa-5,10,12-triazapentadecan-15-oate; (2S)-2-[({3-[(methylsulfonyl)amino]benzyl}carbamoyl)amino]hexyl(2-methoxyethyl)(2-thienylmethyl)carbamate; (2S)-2-{[(4-bromobenzyl)carbamoyl]amino}hexyl bis(2-thienylmethyl)carbamate; (2S)-2-{[(4-azidobenzyl)carbamoyl]amino}hexyl bis(2-thienylmethyl)carbamate; tert-butyl[(2S)-1-{[bis(2-thienylmethyl)carbamoyl]thio}hexan-2-yl]carbamate; and methyl (6S,10S)-10-(1,3-benzodioxol-5-yl)-6-butyl-3,8-dioxo-1-(2-thienyl)-2-(2-thienylmethyl)-4-thia-2,7,9-triazadodecan-12-oate.

In some embodiments, a chemical compound is provided having the general formula (I), wherein
$R^1$ is aryl or aralkyl,
$R^2$ is alkyl, aryl or aralkyl,
$M^1$ is $CH_2$,
$M^2$ is CO,
$M^3$ is absent,
$M^4$ is absent or is $CH_2$,
$M^5$ is $(CR^{11}R^{12})$,
$M^6$ is $(CH_2)_q$, wherein q is an integer of 0 to 6,
$R^{11}$ is hydrogen, and
$R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $OCOR^{24}$, $OR^{24}$, $SCOR^{24}$, $SR^{24}$, $N_3$, CN, and $O(CH_2CH_2O)_sR^{24}$, wherein
s is an integer of 1 to 6,
$R^{21}$ and $R^{22}$ when present are independently selected from the group consisting of hydrogen, lower alkyl, or aralkyl,
$R^{23}$ when present is selected from the group consisting of hydroxyalkyl, alkoxyalkyl, alkyl, aryl, aralkyl, and alkoxycarbonylalkyl, $R^{24}$ when present is selected from the group consisting of alkyl, aryl, aralkyl, heterocyclyl, cycloalkyl, cycloalkylalkyl and heterocyclylalkyl, provided that when $M^3$ and $M^4$ are absent, $R^{12}$ is not of the formula:

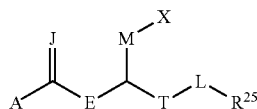

wherein,
A is selected from the group consisting of —O—, —S—, and —NR$^{26}$—,
E is selected from the group consisting of —CH$_2$—, —O—, —S—, and —NR$^{27}$—,
J is selected from the group consisting of —O—, —S—, and —NR$^{28}$—,
T is selected from the group consisting of CO and (CH$_2$)$_b$ wherein b is an integer of zero to three,
L is selected from the group consisting of —(CH$_2$)$_n$—, —O—, —S—, and —NR$^{29}$— wherein n is an integer of zero to three,
M is selected from the group consisting of CR$^{30}$R$^{31}$ and (CH$_2$)$_u$ wherein u is an integer of zero or one,
X is selected from the group consisting of CO$_2$B, PO$_3$H$_2$, SO$_3$H, OPO$_3$H$_2$, CONHCOR$^{32}$, CONHSO$_2$R$^{33}$, oxazolyl, tetrazolyl and hydrogen,
B, $R^{25}$, $R^{26}$, $R^{27}$, $R^{28}$, $R^{29}$, $R^{30}$, $R^{31}$, $R^{32}$ and $R^{33}$ are independently selected from the group consisting of hydrogen, halogen alkyl, alkenyl, alkynyl, alkoxy, alkenoxy, alkynoxy, thioalkoxy, aliphatic acyl, —CF$_3$, nitro, amino, cyano, N(C$_1$-C$_3$ alkyl)CO(C$_1$-C$_3$ alkyl), C$_1$-C$_3$ alkylamino, alkenylamino, alkynylamino, di(C$_1$-C$_3$ alkyl)amino, CO$_2$(C$_1$-C$_3$ alkylamino), CONH(C$_1$-C$_3$ alkylamino), CH=NOH, PO$_3$H$_2$, OPO$_3$H$_2$, CON(C$_1$-C$_3$ alkyl)$_2$, haloalkyl, alkoxycarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkenyl, aralkyl, alkylheterocyclyc, heterocyclycalkyl, sulfonyl, sulfonamide, carbamate, aryloxyalkyl, carboxyl and CONH(benzyl), wherein B, X, $R^{25}$, $R^{26}$, $R^{27}$, $R^{28}$, $R^{29}$, $R^{30}$, $R^{31}$ and $R^{32}$ are unsubstituted or substituted with at least one electron donating or electron withdrawing group,
$R^3$ is selected from the group of hydrogen, $NR^{15}COOR^{16}$, $NR^{15}COR^{16}$, $NR^{15}CONR^{13}R^{14}$, $NR^{15}SO_2R^{16}$, $OCOR^{16}$, $COOR^{16}$, alkyl, $SR^{16}$, heterocyclyl, hydroxyl, hydroxyalkyl, guanadino and aryl, wherein
$R^{13}$ and $R^{15}$ when present are independently hydrogen, lower alkyl, or aralkyl,
$R^{14}$ and $R^{16}$ when present are independently selected from the group consisting of hydrogen, alkyl, aralkyl, cycloalkyl, cycloalkylalkyl, heterocyclyl and heterocyclylalkyl provided that when $R^3$ is hydrogen, alkyl or aryl, $R^{12}$ is not hydrogen, and
provided that when $R^1$ is phenyl, $R^3$ is benzyloxycarbonylamino, and $R^{12}$ is hydrogen, $R^2$ is not 2-methoxybenzyl,
and
$R^1$, $R^2$, $R^3$, $R^{12}$, $R^{13}$, $R^{14}$, $R^{15}$, $R^{16}$, $R^{21}$, $R^{22}$, $R^{23}$ and $R^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, hydroxyalkyl, aryloxy, hydroxyaryl, alkoxyaryl, halo, haloalkyl, haloaryl, haloalkoxy, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), —OCO(dialkylamino).

In some embodiments, a compound is selected from the group consisting of (2R)-2-({[(1S)-1-(1,3-benzodioxol-5-yl)-3-hydroxypropyl]carbamoyl}amino)-N,N-bis(2-thienylmethyl)hexanamide; methyl(3S)-3-(1,3-benzodioxol-5-yl)-3-[({3-[bis(2-thienylmethyl)amino]-3-oxopropyl}carbamoyl)amino]propanoate; (2S)-2-[(tert-butylcarbamoyl)amino]-N,N-bis(2-thienylmethyl)hexanamide; tert-butyl{(2S)-1-[bis(2-thienylmethyl)amino]-1-oxohexan-2-yl}carbamate; benzyl{(5S)-6-[bis(2-thienylmethyl)amino]-5-[(tert-butoxycarbonyl)(methyl)amino]-6-oxohexyl}carbamate; benzyl{(5S)-6-[bis(2-thienylmethyl)amino]-5-[(tert-butoxycarbonyl)amino]-6-oxohexyl}carbamate; benzyl{(5R)-6-[bis(2-thienylmethyl)amino]-5-[(tert-butoxycarbonyl)amino]-6-oxohexyl}carbamate; tert-butyl{(2R)-1-[bis(2-thienylmethyl)amino]-1-oxohexan-2-yl}carbamate; (2S)-2-acetamido-N,N-bis(2-thienylmethyl)hexanamide; benzyl{(5S)-5-acetamido-6-[bis(2-thienylmethyl)amino]-6-oxohexyl}carbamate; (2R)-2-acetamido-N,N-bis(2-thienylmethyl)hexanamide; benzyl{(5S)-5-(benzoylamino)-6-[bis(2-thienylmethyl)amino]-6-oxohexyl}carbamate; (2S)-2-[(phenylsulfonyl)amino]-N,N-bis(2-thienylmethyl)hexanamide; (2S)-2-[methyl(phenylsulfonyl)amino]-N,N-bis(2-thienylmethyl)hexanamide; 2-[(phenylsulfonyl)amino]-N,N-bis(2-thienylmethyl)acetamide; 2-[methyl(phenylsulfonyl)amino]-N,N-bis(2-thienylmethyl)acetamide; (2S)-2-[(methylsulfonyl)amino]-N,N-bis(2-thienylmethyl)hexanamide; (2S)-2-({[3-(4-methoxyphenoxy)propyl]sulfonyl}amino)-N,N-bis(2-thienylmethyl)hexanamide; benzyl{(5S)-6-[bis(2-thienylmethyl)amino]-6-oxo-5-[(2-thienylsulfonyl)amino]hexyl}carbamate; benzyl{(5S)-5-[(tert-butoxycarbonyl)amino]-6-[(3-methoxybenzyl)(2-thienylmethyl)amino]-6-oxohexyl}carbamate; benzyl{(5S)-6-[bis(3-methoxybenzyl)

amino]-5-[(tert-butoxycarbonyl)amino]-6-oxohexyl}carbamate; benzyl{(5R)-5-[(tert-butoxycarbonyl)amino]-6-[(3-methoxybenzyl)(2-thienylmethyl)amino]-6-oxohexyl}carbamate; benzyl{(5R)-6-[bis(3-methoxybenzyl)amino]-5-[(tert-butoxycarbonyl)amino]-6-oxohexyl}carbamate; benzyl[(5S)-5-[(tert-butoxycarbonyl)amino]-6-oxo-6-{[2-(2-thienyl)ethyl](2-thienylmethyl)amino}hexyl]carbamate; benzyl[(5R)-5-[(tert-butoxycarbonyl)amino]-6-oxo-6-{[2-(2-thienyl)ethyl](2-thienylmethyl)amino}hexyl]carbamate; benzyl[(5S)-5-[(tert-butoxycarbonyl)amino]-6-(dibenzylamino)-6-oxohexyl]carbamate; benzyl{(5S)-5-[(tert-butoxycarbonyl)amino]-6-[(4-nitrobenzyl)(2-thienylmethyl)amino]-6-oxohexyl}carbamate; benzyl{(5R)-5-[(tert-butoxycarbonyl)amino]-6-[(4-nitrobenzyl)(2-thienylmethyl)amino]-6-oxohexyl}carbamate; tert-butyl[(2R)-1-[(4-aminobenzyl)(2-thienylmethyl)amino]-6-{[(benzyloxy)carbonyl]amino}-1-oxohexan-2-yl]carbamate; tert-butyl[(2S)-1-[(4-aminobenzyl)(2-thienylmethyl)amino]-6-{[(benzyloxy)carbonyl]amino}-1-oxohexan-2-yl]carbamate; benzyl{(5S)-5-[(tert-butoxycarbonyl)amino]-6-[methyl(2-thienylmethyl)amino]-6-oxohexyl}carbamate; benzyl{(5S)-5-[(tert-butoxycarbonyl)amino]-6-[butyl(2-thienylmethyl)amino]-6-oxohexyl}carbamate; benzyl{(5S)-6-[bis(4-methoxybenzyl)amino]-5-[(tert-butoxycarbonyl)amino]-6-oxohexyl}carbamate; benzyl{(5S)-5-[(tert-butoxycarbonyl)amino]-6-oxo-6-[(pyridin-4-ylmethyl)(2-thienylmethyl)amino]hexyl}carbamate; benzyl{(5S)-5-[(tert-butoxycarbonyl)amino]-6-oxo-6-[(pyridin-3-ylmethyl)(2-thienylmethyl)amino]hexyl}carbamate; benzyl{(5S)-6-[bis(pyridin-4-ylmethyl)amino]-5-[(tert-butoxycarbonyl)amino]-6-oxohexyl}carbamate; tert-butyl{(2S)-1-[bis(2-thienylmethyl)amino]-1-oxo-6-[(2-thienylsulfonyl)amino]hexan-2-yl}carbamate; tert-butyl{(2S)-6-acetamido-1-[bis(2-thienylmethyl)amino]-1-oxohexan-2-yl}carbamate; tert-butyl{(2S)-1-[bis(2-thienylmethyl)amino]-1-oxo-6-[(trifluoroacetyl)amino]hexan-2-yl}carbamate; tert-butyl{(2S)-1-[bis(2-thienylmethyl)amino]-6-[(methylsulfonyl)amino]-1-oxohexan-2-yl}carbamate; tert-butyl{(2S)-1-[bis(2-thienylmethyl)amino]-1-oxo-6-[(2-thienylcarbonyl)amino]hexan-2-yl}carbamate; tert-butyl{(2S)-1-[bis(2-thienylmethyl)amino]-1-oxo-6-[(phenylsulfonyl)amino]hexan-2-yl}carbamate; tert-butyl{(2S)-1-[bis(2-thienylmethyl)amino]-1-oxo-6-[(pyridin-3-ylcarbonyl)amino]hexan-2-yl}carbamate; tert-butyl{(2S)-1-[bis(2-thienylmethyl)amino]-1-oxo-6-[(2-thienylacetyl)amino]hexan-2-yl}carbamate; tert-butyl{(2S)-1-[bis(2-thienylmethyl)amino]-6-hydroxy-1-oxohexan-2-yl}carbamate; tert-butyl[(2S)-1-[bis(2-thienylmethyl)amino]-1-oxo-6-{[(trifluoromethyl)sulfonyl]amino}hexan-2-yl]carbamate; tert-butyl{(2S)-6-[(benzylsulfonyl)amino]-1-[bis(2-thienylmethyl)amino]-1-oxohexan-2-yl}carbamate; tert-butyl{(2S)-6-[benzyl(trifluoroacetyl)amino]-1-[bis(2-thienylmethyl)amino]-1-oxohexan-2-yl}carbamate; tert-butyl[(1R)-2-[bis(2-thienylmethyl)amino]-1-(4-hydroxyphenyl)-2-oxoethyl]carbamate; methyl (4S)-5-[bis(2-thienylmethyl)amino]-4-[(tert-butoxycarbonyl)amino]-5-oxopentanoate; benzyl{(3S)-4-[bis(thiophen-2-ylmethyl)amino]-3-[(tert-butoxycarbonyl)amino]-4-oxobutyl}carbamate; benzyl{(4S)-5-[bis(2-thienylmethyl)amino]-4-[(tert-butoxycarbonyl)amino]-5-oxopentyl}carbamate; tert-butyl{2-[bis(2-thienylmethyl)amino]-2-oxoethyl}carbamate; tert-butyl{2-[bis(2-thienylmethyl)amino]-2-oxoethyl}methylcarbamate; N,N-bis(2-thienylmethyl)-6-[(2-thienylsulfonyl)amino]hexanamide; N-{6-[bis(2-thienylmethyl)amino]-6-oxohexyl}thiophene-2-carboxamide; N-{6-[bis(2-thienylmethyl)amino]-6-oxohexyl}-N-(2-thienylmethyl)thiophene-2-carboxamide; N-benzyl-N-{6-[bis(2-thienylmethyl)amino]-6-oxohexyl}thiophene-2-carboxamide; 6-[benzyl(2-thienylsulfonyl)amino]-N,N-bis(2-thienylmethyl)hexanamide; 6-[methyl(2-thienylsulfonyl)amino]-N,N-bis(2-thienylmethyl)hexanamide; 6-[(benzylsulfonyl)amino]-N,N-bis(2-thienylmethyl)hexanamide; 6-[(2-thienylacetyl)amino]-N,N-bis(2-thienylmethyl)hexanamide; N-{6-[bis(2-thienylmethyl)amino]-6-oxohexyl}-N-(3-methoxybenzyl)thiophene-2-carboxamide; 6-[(3-methoxybenzyl)(2-thienylsulfonyl)amino]-N,N-bis(2-thienylmethyl)hexanamide; 6-[(benzylsulfonyl)(3-methoxybenzyl)amino]-N,N-bis(2-thienylmethyl)hexanamide; benzyl{6-[bis(2-thienylmethyl)amino]-6-oxohexyl}carbamate; tert-butyl{6-[bis(thiophen-2-ylmethyl)amino]-6-oxohexyl}carbamate; tert-butyl[(2S)-1-[bis(2-thienylethyl)amino]-3-(4-hydroxyphenyl)-1-oxopropan-2-yl]carbamate; Methyl(5S)-6-[bis(2-thienylmethyl)amino]-5-[(tert-butoxycarbonyl)amino]-6-oxohexanoate; (2S)-2-[acetyl(methyl)amino]-N,N-bis(2-thienylmethyl)hexanamide; benzyl{(5S)-5-[acetyl(methyl)amino]-6-[bis(2-thienylmethyl)amino]-6-oxohexyl}carbamate; (2S)-6-{[(benzyloxy)carbonyl]amino}-1-[bis(2-thienylmethyl)amino]-1-oxohexan-2-yl acetate; tert-butyl{(2S)-6-[benzyl(2-thienylsulfonyl)amino]-1-[bis(2-thienylmethyl)amino]-1-oxohexan-2-yl}carbamate; benzyl{(5S)-6-{bis[4-(trifluoromethoxy)benzyl]amino}-5-[(tert-butoxycarbonyl)amino]-6-oxohexyl}carbamate; benzyl[(5S)-5-[(tert-butoxycarbonyl)amino]-6-oxo-6-{(2-thienylmethyl) [2-(trifluoromethyl)benzyl]amino}hexyl]carbamate; benzyl[(5S)-5-[(tert-butoxycarbonyl)amino]-6-oxo-6-{(2-thienylmethyl) [2-(trifluoromethoxy)benzyl]amino}hexyl]carbamate; benzyl[(5S)-5-[(tert-butoxycarbonyl)amino]-6-{[2-(difluoromethoxy)benzyl](2-thienylmethyl)amino]-6-oxohexyl}carbamate; tert-butyl{6-[bis(4-methoxybenzyl)amino]-6-oxohexyl}carbamate; N-{6-[bis(4-methoxybenzyl)amino]-6-oxohexyl}-4-methoxybenzamide; N-{6-[bis(4-methoxybenzyl)amino]-6-oxohexyl}-4-methoxy-N-(4-methoxybenzyl)benzamide; N-{6-[bis(2-thienylmethyl)amino]-6-oxohexyl}-N-methylthiophene-2-carboxamide; 6-[(3-methoxybenzyl)(2-thienylacetyl)amino]-N,N-bis(2-thienylmethyl)hexanamide; tert-butyl{4-[bis(2-thienylmethyl)amino]-4-oxobutyl}carbamate; methyl(3S)-3-(1,3-benzodioxol-5-yl)-3-[({4-[bis(2-thienylmethyl)amino]-4-oxobutyl}carbamoyl)amino]propanoate; 6-{[(3-chloropropyl)sulfonyl]amino}-N,N-bis(4-methoxybenzyl)hexanamide; 6-(1,1-dioxido-1,2-thiazolidin-2-yl)-N,N-bis(4-methoxybenzyl)hexanamide; N,N-bis(4-methoxybenzyl)-6-({[2-(morpholin-4-yl)ethyl]sulfonyl}amino)hexanamide; 3-{[bis(2-thienylmethyl)carbamoyl]amino}-N,N-bis(2-thienylmethyl)propanamide; tert-butyl{3-[bis(2-thienylmethyl)amino]-3-oxopropyl}butylcarbamate; 3-{[bis(2-thienylmethyl)carbamoyl](butyl)amino}-N,N-bis(2-thienylmethyl)propanamide; 3-{butyl[(2-thienylmethyl)carbamoyl]amino}-N,N-bis(2-thienylmethyl)propanamide; 4-(1,1-dioxido-1,2-thiazolidin-2-yl)-N,N-bis(2-thienylmethyl)butanamide; N,N-bis(2-thienylmethyl)-3-{[(2-thienylmethyl)carbamoyl]amino}propanamide; benzyl{(5S)-6-[bis(2-thienylmethyl)amino]-5-hydroxy-6-oxohexyl}carbamate; benzyl{(5S)-6-bis(2-thienylmethyl)amino]-5-cyano-6-oxohexyl}carbamate; benzyl{(5R)-5-azido-6-[bis(2-thienylmethyl)amino]-6-oxohexyl}carbamate; S-{(2R)-6-{[(benzyloxy)carbonyl]amino}-1-[bis(2-thienylmethyl)amino]-1-oxohexan-2-yl}ethanethioate; tert-butyl[(2S)-1-[bis(2-thienylmethyl)amino]-6-({[(4-bromobenzyl)oxy]carbonyl}amino)-1-oxohexan-2-yl]carbamate;

4-azidobenzyl{(5S)-6-[bis(2-thienylmethyl)amino]-5-[(tert-butoxycarbonyl)amino]-6-oxohexyl}carbamate; benzyl {(5S)-6-[(4-bromobenzyl)(2-thienylmethyl)amino]-5-[(tert-butoxycarbonyl)amino]-6-oxohexyl}carbamate; tert-butyl [(2S)-1-[(4-azidobenzyl)(2-thienylmethyl)amino]-6-{[(benzyloxy)carbonyl]amino}-1-oxohexan-2-yl]carbamate; tert-butyl{(2S)-1-[(4-bromobenzyl)(2-thienylmethyl)amino]-1-oxohexan-2-yl}carbamate; benzyl{(5S)-6-[bis(3-thienylmethyl)amino]-5-[(tert-butoxycarbonyl)amino]-6-oxohexyl}carbamate; and benzyl{(5S)-5-[(tert-butoxycarbonyl)amino]-6-[(cyclopropylmethyl)(2-thienylmethyl)amino]-6-oxohexyl}carbamate.

In some embodiments, a chemical compound is provided having the general formula (I), wherein $R^1$ is alkyl, aryl or aralkyl, $R^2$ is selected from the group consisting of aralkyl and alkyl, provided that when $R^1$ is alkyl, $R^2$ is aralkyl, $M^1$ is CO or $SO_2$, provided that when $M^1$ is $SO_2$ and $R^1$ is phenyl, 4-methylphenyl or 2,4,6-trimethylphenyl, $R^2$ is not alkyl, 2-phenethyl, benzyl, or 2-methoxy-2-oxoethyl, and when $M^1$ is CO and $R^1$ is 2-furyl, 4-pyridyl, or 3,5-dinitrophenyl, $R^2$ is not alkyl, benzyl or 2-(1H-indol-2-yl)ethyl, $M^2$ is absent or $CH_2$, $M^3$ and $M^4$ are absent, $M^5$ is ($CR^{11}R^{12}$), $R^{11}$ is hydrogen, $R^{12}$ is selected from the group consisting of hydrogen, $NR^{21}CONR^{22}R^{23}$, $NR^{21}COR^{24}$, $NR^{21}SO_2R^{24}$, $NR^{21}COOR^{24}$, $CONR^{22}R^{23}$, $COOR^{24}$, $O(CH_2CH_2O)_sR^{24}$ hydroxyalkyl and alkoxyalkyl, wherein s is an integer of 1 to 6, $M^6$ is $(CH_2)_q$ where q is an integer of 0 to 6, $R^3$ is selected from the group consisting of $NR^{15}COOR^{16}$, $NR^{15}COR^{16}$, $NR^{15}CONR^{13}R^{14}$, and $NR^{15}SO_2R^{16}$, and $R^{13}$, $R^{21}$ and $R^{22}$, when present, are independently selected from the group consisting of hydrogen and lower alkyl, and $R^{14}$, $R^{15}$ $R^{16}$, $R^{23}$ and $R^{24}$, each of which when present, is independently selected from the group consisting of hydrogen, alkyl, aryl, cycloalkyl, cycloalkylalkyl, heterocyclyl, heterocyclylalkyl and aralkyl, and $R^1$, $R^2$, $R^3$, $R^{12}$, $R^{14}$, $R^{15}$, $R^{16}$, $R^{23}$ and $R^{24}$ when present may independently be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO_2(alkyl), —NHSO_2(aryl), —NHSO_2(aralkyl), alkoxycarbonyl, alkoxycarbonylalkyl, —OCO(alkylamino) and —OCO(dialkylamino).

In some embodiments, a compound is selected from the group consisting of methyl(2S)-6-{[(benzyloxy)carbonyl] amino}-2-[benzyl(2-thienylsulfonyl)amino]hexanoate; methyl(2S)-6-{[(benzyloxy)carbonyl]amino}-2-[benzyl (phenylsulfonyl)amino]hexanoate; methyl(2S)-6-{[(benzyloxy)carbonyl]amino}-2-[(2-thienylcarbonyl)(2-thienylmethyl)amino]hexanoate; methyl(2S)-6-{[(benzyloxy) carbonyl]amino}-2-[(2-thienylacetyl)(2-thienylmethyl) amino]hexanoate; methyl(2S)-2-[benzyl(isobutylsulfonyl) amino]-6-{[(benzyloxy)carbonyl]amino}hexanoate; benzyl{(5S)-5-[(tert-butoxycarbonyl)amino]-6-[(2-thienylmethyl)(2-thienylsulfonyl)amino]hexyl}carbamate; benzyl {(5S)-5-[(tert-butoxycarbonyl)amino]-6-[(2-thienylacetyl) (2-thienylmethyl)amino]hexyl}carbamate; benzyl{(5S)-5-[(tert-butoxycarbonyl)amino]-6-[(methylsulfonyl)(2-thienylmethyl)amino]hexyl}carbamate; benzyl{(5S)-5-[(tert-butoxycarbonyl)amino]-6-[(phenylsulfonyl)(2-thienylmethyl)amino]hexyl}carbamate; benzyl{(5S)-5-[(tert-butoxycarbonyl)amino]-6-[(2-thienylcarbonyl)(2-thienylmethyl)amino]hexyl}carbamate; N,N'-heptane-1,7-diylbis[N-(2-thienylmethyl)benzamide]; N,N'-heptane-1,7-diylbis[N-(2-thienylmethyl)thiophene-2-carboxamide]; benzyl[(5S)-5-[(tert-butoxycarbonyl)amino]-6-{[(4-methoxyphenyl)sulfonyl](2-thienylmethyl)amino}hexyl] carbamate; benzyl{(5S)-5-[(tert-butoxycarbonyl)amino]-6-[(4-methoxybenzoyl)(2-thienylmethyl)amino] hexyl}carbamate; N,N'-hexane-1,6-diylbis[N-(2-thienylmethyl)thiophene-2-carboxamide]; N,N'-hexane-1,6-diylbis[N-(3-methoxybenzyl)thiophene-2-carboxamide]; tert-butyl{5-[(4-methoxybenzyl)(2-thienylsulfonyl)amino] pentyl}carbamate; N,N'-pentane-1,5-diylbis[N-(3-methoxybenzyl)thiophene-2-sulfonamide]; N-(3-methoxybenzyl)-N-{5-[(2-thienylsulfonyl)amino]pentyl}thiophene-2-sulfonamide; tert-butyl{5-[(2-thienylcarbonyl)(2-thienylmethyl)amino]pentyl}carbamate; N-(3-methoxybenzyl)-N-{5-[(2-thienylcarbonyl)amino] pentyl}thiophene-2-carboxamide; and N,N'-pentane-1,5-diylbis[N-(3-methoxybenzyl)thiophene-2-carboxamide].

In some embodiments, a chemical compound is selected having the general formula (I) wherein $R^1$ is aryl or aralkyl, $R^2$ is alkyl or aralkyl, $M^1$ is $CH_2$, $M^2$ is CO, $M^3$ is absent or is O or $CH_2$, $M^4$ is absent or is $CH_2$, $M^5$ is absent or is O or $(CR^{11}R^{12})$, $R^{11}$ is hydrogen, $R^{12}$ is selected from the group consisting of hydrogen, $NR^{21}CONR^{22}R^{23}$, $NR^{21}COR^{24}$, $NR^{21}SO_2R^{24}$ and $NR^{21}COOR^{24}$, $M^6$ is selected from the group consisting of $(CH_2)_q$, $(CH_2)_q$—CH=CH—$(CH_2)_r$, $(CH_2)_q$-arylene-$(CH_2)_r$ and $(CH_2CH_2O)_q$, wherein q and r are independently integers from 0 to 6, $R^3$ is $CONR^{13}R^{14}$, $R^{21}$ and $R^{22}$ each of which, when present is independently selected from the group of hydrogen and lower alkyl, $R^{13}$, $R^{14}$, $R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl, and $R^1$, $R^2$, $R^{13}$, $R^{14}$, $R^{23}$ and $R^{24}$ when present may be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO_2(alkyl), —NHSO_2 (aryl), —NHSO_2(aralkyl), alkoxycarbonyl, alkoxycarbonylalkyl, —OCO(alkylamino), and —OCO(dialkylamino).

In some embodiments, a compound is selected from the group consisting of N,N,N',N'-tetrakis(2-thienylmethyl)pentanediamide; N-(3-methoxybenzyl)-N,N',N'-tris(2-thienylmethyl)pentanediamide; N,N,N'-tris(2-thienylmethyl)pentanediamide; N'-[2-(2-thienyl)ethyl]-N,N-bis(2-thienylmethyl)pentanediamide; N-[2-(2-thienyl)ethyl]-N,N', N'-tris(2-thienylmethyl)pentanediamide; N,N-bis(pyridin-4-ylmethyl)-N',N'-bis(2-thienylmethyl)pentanediamide; N,N-bis(pyridin-3-ylmethyl)-N',N'-bis(2-thienylmethyl)pentanediamide; N,N-bis(3-methoxybenzyl)-N',N'-bis(2-thienylmethyl)pentanediamide; N,N,N',N'-tetrakis(4-methoxybenzyl)pentanediamide; N,N,N',N'-tetrakis(2-thienylmethyl)hexanediamide; N,N,N',N'-tetrakis(4-methoxybenzyl)hexanediamide; N,N,N',N'-tetrakis(3-methoxybenzyl)hexanediamide; N,N,N',N'-tetrakis(2-thienylmethyl)heptanediamide; 2,2'-(1,3-phenylene)bis[N,N-bis(2-thienylmethyl)acetamide]; N,N,N',N'-tetrakis(4-methoxybenzyl)heptanediamide; N,N,N',N'-tetrakis(2-thienylmethyl)octanediamide; (3E)-N,N,N',N'-tetrakis(2-thienylmethyl)hex-3-enediamide; 2,2'-oxybis[N,N-bis(2-thienylmethyl)acetamide]; 3-oxo-1-(2-thienyl)-2-(2-thienylmethyl)-4,7,10-trioxa-2-azadodecan-12-yl bis(2-thienylmethyl)carbamate; N,N,N',N'-tetrakis(4-methoxybenzyl)succinamideethane-1,2-diyl bis[bis(2-thienylmethyl)carbamate]; N,N,N',N'-tetrakis(4-methoxybenzyl)octanediamide; N,N,N',N'-tetrakis(2-thienylmethyl)pyridine-3,5-dicarboxamide; N,N,N',N'-tetrakis(2-thienylmethyl)pyridine-2,6-dicarboxamide; N,N,N',N'-tetrakis(2-thienylmethyl)pyridine-2,4-dicarboxamide; 2,2'-(1,4-phenylene)bis[N,N-bis(2-thienylmethyl)acetamide]; 8-{2-[bis(2-thienylmethyl)amino]-2-oxoethoxy}-N,N-bis(2-thienylmethyl)quinoline-2-carboxamide; N,N'-bis(4-methoxybenzyl)-N,N'-bis(2-thienylmethyl)hexanediamide; and tert-butyl{(2S)-1,6-bis[bis(2-thienylmethyl)amino]-1,6-dioxohexan-2-yl}carbamate.

In some embodiments a chemical compound is provided having the general formula (I), wherein
$R^1$ is aryl or aralkyl,
$R^2$ is alkyl or aralkyl,
$M^1$ is $CH_2$,
$M^2$ is $SO_2$ or CO,
$M^3$ is absent or is $CH_2$,
$M^4$ is absent or is $CH_2$,
$M^5$ is absent or is $(CR^{11}R^{12})$,
$R^{11}$, when present, is hydrogen,
$R^{12}$, when present, is selected from the group consisting of hydrogen, alkyl, $NR^{21}CONR^{22}R^{23}$, $NR^{21}COR^{24}$, $NR^{21}SO_2R^{24}$ and $NR^{21}COOR^{24}$,
$M^6$ is $(CH_2)_q$, or $NR^{34}(CH_2)_q$, wherein q is an integer from 0 to 6,
$R^3$ is selected from the group consisting of $CONR^{13}R^{14}$, $SO_2NR^{13}R^{14}$, $NR^{15}COOR^{16}$, $NR^{15}COR^{16}$, $NR^{15}CONR^{13}R^{14}$, and $NR^{15}SO_2R^{16}$,
$R^{15}$, $R^{16}$, $R^{21}$ and $R^{22}$, each of which when present, is independently selected from the group of hydrogen, lower alkyl, and aralkyl,
$R^{13}$, $R^{14}$, $R^{23}$ and $R^{24}$, each of which, when present is independently selected from the group consisting of hydrogen, alkyl, aryl, cycloalkyl, cycloalkylalkyl, heterocyclyl, heterocyclylalkyl and aralkyl,
$R^{34}$, when present, is selected form the group consisting of alkyl, aralkyl, $COR^{35}$, and $SO_2R^{35}$,
$R^{35}$ is selected form the group consisting of alkyl, aryl, and aralkyl, and
$R^1$, $R^2$, $R^{13}$, $R^{14}$, $R^{15}$, $R^{16}$, $R^{23}$, $R^{24}$, $R^{34}$ and $R^{35}$, when present, may be either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxy, alkoxy, azido, haloalkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(aralkyl), —NHCO(haloalkyl), —NHSO$_2$(alkyl), —NHSO$_2$(aryl), —NHSO$_2$(aralkyl), alkoxycarbonyl, alkoxycarbonylalkyl, —OCO(alkylamino), and —OCO(dialkylamino),
with the proviso that when $M_2$ is CO, then $M^6$ is $NR^{34}(CH_2)_q$ wherein q is not 0.

In some embodiments, a compound is selected from the group consisting of N-{2-[bis(2-thienylmethyl)sulfamoyl]ethyl}-N-(2-thienylmethyl)thiophene-2-sulfonamide; N-{2-[bis(2-thienylmethyl)sulfamoyl]ethyl}-N-(2-thienylmethyl)thiophene-2-carboxamide; 2-{butyl[(2-thienylmethyl)carbamoyl]amino}-N,N-bis(2-thienylmethyl)ethanesulfonamide; 2-{[bis(2-thienylmethyl)carbamoyl](butyl)amino}-N,N-bis(2-thienylmethyl)ethanesulfonamide; N-{3-[bis(2-thienylmethyl)sulfamoyl]propyl}-N-(2-thienylmethyl)thiophene-2-sulfonamide; 2-[(methylsulfonyl)(2-thienylmethyl)amino]-N,N-bis(2-thienylmethyl)ethanesulfonamide; 2-{[bis(2-thienylmethyl)carbamoyl]amino}-N,N-bis(2-thienylmethyl)ethanesulfonamide; N-{2-[bis(2-thienylmethyl)sulfamoyl]ethyl}thiophene-2-sulfonamide; N-{2-[bis(2-thienylmethyl)sulfamoyl]ethyl}-2-(2-thienyl)acetamide; N-{2-[bis(2-thienylmethyl)sulfamoyl]ethyl}thiophene-2-carboxamide; N,N-bis(2-thienylmethyl)-2-{[(2-thienylmethyl)carbamoyl]amino}ethanesulfonamide; 2-({2-[bis(2-thienylmethyl)sulfamoyl]ethyl}amino)-N,N-bis(2-thienylmethyl)acetamide; 3-[{2-[bis(2-thienylmethyl)amino]-2-oxoethyl}(butyl)amino]-N,N-bis(2-thienylmethyl)propanamide; 2-[{2-[bis(2-thienylmethyl)sulfamoyl]ethyl}(methyl)amino]-N,N-bis(2-thienylmethyl)acetamide; 2-[{2-[bis(2-thienylmethyl)sulfamoyl]ethyl}(butyl)amino]-N,N-bis(2-thienylmethyl)acetamide; 3-({2-[bis(2-thienylmethyl)sulfamoyl]ethyl}amino)-N,N-bis(2-thienylmethyl)propanamide; 3-({2-[bis(2-thienylmethyl)sulfamoyl]ethyl}amino)-N,N-bis(4-methoxybenzyl)propanamide; 3-({2-[bis(4-methoxybenzyl)sulfamoyl]ethyl}amino)-N,N-bis(2-thienylmethyl)propanamide; 3-[{2-[bis(2-thienylmethyl)sulfamoyl]ethyl}(methyl)amino]-N,N-bis(2-thienylmethyl)propanamide; 3-[{2-[bis(4-methoxybenzyl)sulfamoyl]ethyl}(methyl)amino]-N,N-bis(2-thienylmethyl)propanamide; (2S)-2-({2-[bis(2-thienylmethyl)sulfamoyl]ethyl}amino)-N,N-bis(2-thienylmethyl)hexanamide; (2S)-2-({2-[bis(4-methoxybenzyl)sulfamoyl]ethyl}amino)-N,N-bis(2-thienylmethyl)hexanamide; 2-(acetyl{2-[bis(2-thienylmethyl)sulfamoyl]ethyl}amino)-N,N-bis(2-thienylmethyl)acetamide; and 2-(acetyl{2-[bis(4-methoxybenzyl)sulfamoyl]ethyl}amino)-N,N-bis(2-thienylmethyl)acetamide.

In some embodiments, a compound is selected from the group consisting of tert-butyl[(2S)-1-{[bis(cyclopropylmethyl)carbamoyl]oxy}hexan-2-yl]carbamate; (2S)-2-[(tert-butoxycarbonyl)amino]hexyl diisobutylcarbamate; methyl (8S,12S)-12-(1,3-benzodioxol-5-yl)-8-butyl-4-isobutyl-2-methyl-5,10-dioxo-6-oxa-4,9,11-triazatetradecan-14-oate; and benzyl{(5S)-6-[bis(cyclopropylmethyl)amino]-5-[(tert-butoxycarbonyl)amino]-6-oxohexyl}carbamate.

In accordance with certain embodiments, a pharmaceutical composition is provided comprising an above-described compound or a pharmaceutically acceptable salt thereof; and a pharmaceutically acceptable carrier.

In accordance with certain embodiments, a method of treating integrin-expressing cells is provided. The integrin may be one or more of α4β1, α5β1, α4β7, αvβ3 and αLβ2, for example. In some embodiments, the method of treating integrin-expressing cells comprises contacting at least one integrin-expressing cell in vitro with an agonist of said integrin, wherein said agonist is a compound having the general formula (I), wherein
- $R^1$ and $R^2$ are independently selected from the group consisting of alkyl, aryl, aralkyl, cycloalkyl, cycloalkylalkyl, haloalkyl, heterocylcyl and heterocyclylalkyl,
- one of $M^1$ and $M^2$ is CO or $SO_2$ and the other is $(CR^4R^5)_l$, provided that when $M^2$ is CO, $M^3$ is O, S, $NR^6$ or $(CR^7R)_m$, and provided that when $M^2$ is $SO_2$ or $(CR^4R^5)_l$, $M^3$ is $(CR^7R^8)_m$,
- $M^4$ is absent or $(CR^9R^{10})_n$,
- $M^5$ is absent or is O or $(CR^{11}R^{12})_p$,
- $M^6$ is absent or is selected from the group consisting of $(CH_2)_q$, $(CH_2)_q$—CH═CH—$(CH_2)_r$, $(CH_2)_q$-arylene-$(CH_2)_r$, $(CH_2CH_2O)_q$, and $NR^{34}(CH_2)_q$, and
- $R^3$ is selected from the group consisting of hydrogen, OH, $OR^{16}$, $CONR^{13}R^{14}$, $NR^{15}COOR^{16}$, $NR^{15}COR^{16}$, $NR^{15}CONR^{13}R^{14}$, $NR^{15}SO_2R^{16}$, $OCOR^{16}$, $COOR^{16}$, alkyl, aryl, aralkyl, $SR^{16}$, heterocyclyl, hydroxyalkyl and guanadino,
- $R^{34}$, when present, is selected form the group consisting of alkyl, aralkyl, $COR^{35}$, and $SO_2R^{35}$,
- $R^{35}$, when present, is selected form the group consisting of alkyl, aryl, and aralkyl, and
- $R^{12}$, when present, is selected from the group consisting of hydrogen, alkyl, OH, $N_3$, CN, $NR^{21}CONR^{22}R^{23}$, $NR^{21}COR^{24}$, $NR^{21}COOR^{24}$, $NR^{21}SO_2R^{24}$, $CONR^{22}R^{23}$, $COOR^{24}$, $OCOR^{24}$, $OR^{24}$, $SCOR^{24}$, $SR^{24}$, azido, CN, and $O(CH_2CH_2O)_sR^{24}$,
- $R^4$, $R^5$, $R^6$, $R^7$, $R^8$, $R^9$, $R^{10}$, $R^{11}$, $R^{15}$, and $R^{21}$, each of which when present, is independently selected from the group consisting of hydrogen, lower alkyl and aralkyl,
- $R^{13}$, $R^{14}$, $R^{16}$, $R^{22}$, $R^{23}$ and $R^{24}$, each of which when present, is independently selected from the group consisting of alkyl, aryl, aralkyl, cycloalkyl, cycloalkylalkyl, haloalkyl, heterocyclyl, heterocyclylalkyl, alkoxycarbonyl, alkoxycarbonylalkyl,
- l, m, n and p are independently integers from 0 to 1,
- q, r and s are independently integers from 0 to 6,
- $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{21}$, $R^{22}$, $R^{23}$, $R^{24}$, $R^{34}$ and $R^{35}$, each of which when present, is independently either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxyl, alkoxy, haloalkoxy, azido, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO(haloalkyl), —NHSO$_2$(alkyl), —NHSO$_2$(aryl), alkoxycarbonyl, alkoxycarbonylalkyl, —OCO(alkylamino), —OCO(dialkylamino).

In accordance with certain embodiments, a method of enhancing binding of cells to an integrin-binding ligand is provided, wherein the method comprises treating integrin-expressing cells in vitro with an agonist of integrin described above, wherein said integrin is selected from the group consisting of α4β1, α5β1, α4β7, αvβ3 and αLβ2; and contacting the treated cells with an integrin-binding ligand.

In some embodiments, the agonist of integrin utilized in an above described method is a compound selected from the group consisting of methyl(3R)-3-(1,3-benzodioxol-5-yl)-3-[({(2R)-1-[bis(2-thienylmethyl)amino]-1-oxohexan-2-yl}carbamoyl)amino]propanoate; methyl(3S)-3-(1,3-benzodioxol-5-yl)-3-[({(2R)-6-{[(benzyloxy)carbonyl]amino}-1-[bis(thiophen-2-ylmethyl)amino]-1-oxohexan-2-yl}carbamoyl)amino]propanoate; methyl(3S)-3-(1,3-benzodioxol-5-yl)-3-[({(2R)-1-[bis(thiophen-2-ylmethyl)amino]-1-oxohexan-2-yl}carbamoyl)amino]propanoate; methyl(3R)-3-(1,3-benzodioxol-5-yl)-3-[({(2S)-1-[bis(2-thienylmethyl)amino]-1-oxohexan-2-yl}carbamoyl)amino]propanoate; methyl(3S)-3-(1,3-benzodioxol-5-yl)-3-[({2-[bis(2-thienylmethyl)amino]-2-oxoethyl}carbamoyl)amino]propanoate; methyl(3S)-3-(1,3-benzodioxol-5-yl)-3-[({2-[bis(2-thienylmethyl)amino]-2-oxoethyl}carbamoyl)amino]propanoate; methyl(3S)-3-(1,3-benzodioxol-5-yl)-3-{[{2-[bis(2-thienylmethyl)amino]-2-oxoethyl}(methyl)carbamoyl]amino}propanoate; methyl(3R)-3-(1,3-benzodioxol-5-yl)-3-{[{2-[bis(2-thienylmethyl)amino]-2-oxoethyl}(methyl)carbamoyl]amino}propanoate; methyl(3R)-3-(1,3-benzodioxol-5-yl)-3-[({2-[bis(2-thienylmethyl)amino]-2-oxoethyl}carbamoyl)amino]propanoate; methyl (2R)-[({(2S)-1-[bis(thiophen-2-ylmethyl)amino]-1-oxohexan-2-yl}carbamoyl)amino](phenyl)ethanoate; methyl 3-[({(2S)-1-[bis(2-thienylmethyl)amino]-1-oxohexan-2-yl}carbamoyl)amino]propanoate; (2S)-2-[(isopropylcarbamoyl)amino]-N,N-bis(2-thienylmethyl)hexanamide; (2S)-2-[(methylcarbamoyl)amino]-N,N-bis(2-thienylmethyl)hexanamide; (2S)-2-[(benzylcarbamoyl)amino]-N,N-bis(2-thienylmethyl)hexanamide; (2R)-2-[(benzylcarbamoyl)amino]-N,N-bis(2-thienylmethyl)hexanamide; benzyl{(5S)-5-[(benzylcarbamoyl)amino]-6-[bis(2-thienylmethyl)amino]-6-oxohexyl}carbamate; (2S)-2-{[(1,3-benzodioxol-5-ylmethyl)carbamoyl]amino}-N,N-bis(2-thienylmethyl)hexanamide; benzyl[(5S)-6-[bis(2-thienylmethyl)amino]-6-oxo-5-{[(pyridin-3-ylmethyl)carbamoyl]amino}hexyl]carbamate; (2S)-2-{[(pyridin-3-ylmethyl)carbamoyl]amino}-N,N-bis(2-thienylmethyl)hexanamide; (2S)-2-({[(6-methoxypyridin-3-yl)methyl]carbamoyl}amino)-N,N-bis(2-thienylmethyl)hexanamide; (2S)-2-({[3-(morpholin-4-yl)benzyl]carbamoyl}amino)-N,N-bis(2-thienylmethyl)hexanamide; (2S)-2-{[(4-hydroxybenzyl)carbamoyl]amino}-N,N-bis(2-thienylmethyl)hexanamide; (2S)-2-({[4-(dimethylamino)benzyl]carbamoyl}amino)-N,N-bis(2-thienylmethyl)hexanamide; benzyl[(5S)-6-[bis(2-thienylmethyl)amino]-5-({[3-(morpholin-4-yl)benzyl]carbamoyl}amino)-6-oxohexyl]carbamate; benzyl{(5S)-6-[bis(2-thienylmethyl)amino]-5-[({3-[(methylsulfonyl)amino]benzyl}carbamoyl)amino]-6-oxohexyl}carbamate; benzyl{(2S)-6-{[(benzyloxy)carbonyl]amino}-1-[bis(2-thienylmethyl)amino]-1-oxohexan-2-yl}carbamate; benzyl{(2S)-1-[bis(2-thienylmethyl)amino]-1-oxohexan-2-yl}carbamate; benzyl{(5S)-6-[bis(2-thienylmethyl)amino]-5-[(ethoxycarbonyl)amino]-6-oxohexyl}carbamate; benzyl[(5S)-6-[bis(2-thienylmethyl)amino]-5-(butyrylamino)-6-oxohexyl]carbamate; and benzyl{(5S)-6-[bis(2-thienylmethyl)amino]-6-oxo-5-[(3-phenoxypropanoyl)amino]hexyl}carbamate.

In other embodiments, an integrin agonist used in a method of enhancing binding of cells to an integrin-binding ligand is selected from the group consisting of compounds having the general formula (I) wherein
- $R^1$ is selected from the group consisting of alkyl, aryl, and aralkyl,
- $R^2$ is selected from the group consisting of alkyl, aryl, aralkyl, alkoxyalkyl and hydroxyalkyl,
- $M^1$ is $CH_2$,
- $M^2$ is $SO_2$;
- $M^3$, $M^4$, $M^5$, and $M^6$ independently are absent or are $CH_2$;
- $R^3$ is selected from the group consisting of alkyl, aryl, aralkyl, aryloxyalkyl, alkoxyalkyl, cycloalkyl and cycloalkylalkyl;
- $R^1$, $R^2$ and $R^3$ are independently either unsubstituted or substituted with one or more substituents selected from the group consisting of alkyl, aryl, aralkyl, cycloalkyl, cycloalkylalkyl, heterocyclyl, heterocyclylalkyl, heterocyclylaryl, hydroxyl, alkoxy, hydroxyalkyl, aryloxy, hydroxyaryl, alkoxyaryl, halo, haloalkyl, haloaryl, amino, alkylamino, dialkylamino, arylamino, diarylamino, —NHCO(alkyl), —NHCO(aryl), —NHCO (haloalkyl), —NHSO$_2$(alkyl), —NHSO$_2$(aryl), alkoxycarbonyl, alkoxycarbonylalkyl, —OCO(alkylamino), —OCO(dialkylamino).

In accordance with some further embodiments, an integrin agonist used in a method of enhancing binding of cells to an integrin-binding ligand is selected from the group consisting of N-bis(2-thienylmethyl)benzenesulfonamide; N,N-bis(2-thienylmethyl)acetamide; 1-phenyl-N,N-bis(2-thienylmethyl)methanesulfonamide; 2-methyl-N,N-bis(2-thienylmethyl)propane-1-sulfonamide; N-(3-methoxybenzyl)-N-(2-thienylmethyl)benzenesulfonamide; N-(3-methoxybenzyl)-N-(2-thienylmethyl)propane-2-sulfonamide; N-(3-methoxybenzyl)-2-methyl-N-(2-thienylmethyl)propane-1-sulfonamide; N-(4-hydroxybenzyl)-3-methoxy-N-(2-thienylmethyl)benzenesulfonamide; N-[2-(2-thienyl)ethyl]-N-(2-thienylmethyl)benzenesulfonamide; N,N-dibenzylbenzenesulfonamide; N-(pyridin-3-ylmethyl)-N-(2-thienylmethyl)benzenesulfonamide; N-butyl-N-(2-thienylmethyl)benzenesulfonamide; N-(3-hydroxypropyl)-N-(2-thienylmethyl)benzenesulfonamide; N-(2-methoxyethyl)-N-(2-thienylmethyl)benzenesulfonamide; N-(2-methoxyethyl)-N-(2-thienylmethyl)thiophene-2-sulfonamide; N,N-bis(3-methoxybenzyl)benzenesulfonamide; N,N-bis(4-methoxybenzyl)thiophene-2-sulfonamide; 2-chloro-N,N-bis(2-thienylmethyl)benzenesulfonamide; 3-chloro-N,N-bis(2-thienylmethyl)benzenesulfonamide; 4-chloro-N,N-bis(2-thienylmethyl)benzenesulfonamide; 3-methoxy-N,N-bis(2-thienylmethyl)benzenesulfonamide; 4-methoxy-N,N-bis(2-thienylmethyl)benzenesulfonamide; N,N-bis(pyridin-4-ylmethyl)benzenesulfonamide; N,N-bis(pyridin-3-ylmethyl)benzenesulfonamide; N-(2-furylmethyl)-N-(2-thienylmethyl)benzenesulfonamide; N,N-bis(2-furylmethyl)benzenesulfonamide; N,N-bis(3-methoxybenzyl)thiophene-2-sulfonamide; methyl 3-[bis(3-methoxybenzyl)sulfamoyl]thiophene-2-carboxylate; 2-(hydroxymethyl)-N,N-bis(3-methoxybenzyl)thiophene-3-sulfonamide; N,N-bis(4-methoxybenzyl)-3-methylbenzenesulfonamide; N-phenyl-N-(2-thienylmethyl)benzenesulfonamide; N-phenyl-N-(2-thienylmethyl)thiophene-2-sulfonamide; N-(3-methoxybenzyl)-N-phenylthiophene-2-sulfonamide; N-(3-methoxybenzyl)-N-phenylbenzenesulfonamide; 3-(4-methoxyphenoxy)-N,N-bis(2-thienylmethyl)propane-1-sulfonamide; 4-methyl-N,N-bis(2-thienylmethyl)benzenesulfonamide; 2-methyl-N,N-bis(2-thienylmethyl)benzenesulfonamide; and 3-methyl-N,N-bis(2-thienylmethyl)benzenesulfonamide.

In other embodiments a method of enhancing binding of cells to an integrin-binding ligand is provided, wherein said agonist of integrin is a compound selected from the group consisting of methyl(6S,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl(6S,10S)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; tert-butyl[(2S)-1-{[bis(2-thienylmethyl)carbamoyl]oxy}hexan-2-yl]carbamate; (2S)-2-{[(1,3-benzodioxol-5-ylmethyl)carbamoyl]amino}hexyl bis(2-thienylmethyl)carbamate; methyl(6S,10S)-6-butyl-3,8-dioxo-10-phenyl-1-(2-thienyl)-2-(2-thienylmethyl)-4-oxa-2,7,9-triazadodecan-12-oate; (2S)-2-[(benzylcarbamoyl)amino]hexyl bis(2-thienylmethyl)carbamate; (2S)-2-({[(1S)-1-(1,3-benzodioxol-5-yl)-3-hydroxypropyl]carbamoyl}amino)hexyl bis(2-thienylmethyl)carbamate; methyl(6S,10R)-10-(1,3-benzodioxol-5-yl)-6-butyl-3,8-dioxo-1-(2-thienyl)-2-(2-thienylmethyl)-4-oxa-2,7,9-triazadodecan-12-oate; benzyl{(5S)-6-{[bis(2-thienylmethyl)carbamoyl]oxy}-5-[(tert-butoxycarbonyl)amino]hexyl}carbamate; methyl(9S,13S)-13-(1,3-benzodioxol-5-yl)-9-({[bis(2-thienylmethyl)carbamoyl]oxy}methyl)-3,11-dioxo-1-phenyl-2-oxa-4,10,12-triazapentadecan-15-oate; tert-butyl[(2R)-1-{[bis(2-thienylmethyl)carbamoyl]oxy}hexan-2-yl]carbamate; tert-butyl{[bis(2-thienylmethyl)carbamoyl](butyl)amino}acetate; benzyl{(5S)-6-{[bis(4-methoxybenzyl)carbamoyl]oxy}-5-[(tert-butoxycarbonyl)amino]hexyl}carbamate; tert-butyl[(2S)-1-{[bis(4-methoxybenzyl)carbamoyl]oxy}hexan-2-yl]carbamate; methyl(6S,10S)-10-(1,3-benzodioxol-5-yl)-6-butyl-2-(4-methoxybenzyl)-1-(4-methoxyphenyl)-3,8-dioxo-4-oxa-2,7,9-triazadodecan-12-oate; (2S)-2-({[(1S)-1-(1,3-benzodioxol-5-yl)-3-hydroxypropyl]carbamoyl}amino)hexyl bis(4-methoxybenzyl)carbamate; (2S)-2-[(tert-butoxycarbonyl)amino]hexyl dibenzylcarbamate; methyl(6S,10S)-10-(1,3-benzodioxol-5-yl)-2-benzyl-6-butyl-3,8-dioxo-1-phenyl-4-oxa-2,7,9-triazadodecan-12-oate; tert-butyl[(2S)-1-{[bis(4-methylbenzyl)carbamoyl]oxy}hexan-2-yl]carbamate; methyl(6S,10S)-10-(1,3-benzodioxol-5-yl)-6-butyl-2-(4-methylbenzyl)-1-(4-methylphenyl)-3,8-dioxo-4-oxa-2,7,9-triazadodecan-12-oate; tert-butyl[(2S)-1-{[bis(4-chlorobenzyl)carbamoyl]oxy}hexan-2-yl]carbamate; methyl(6S,10S)-10-(1,3-benzodioxol-5-yl)-6-butyl-2-(4-chlorobenzyl)-1-(4-chlorophenyl)-3,8-dioxo-4-oxa-2,7,9-triazadodecan-12-oate; methyl(6S,10S)-10-(1,3-benzodioxol-5-yl)-2-(4-bromobenzyl)-6-butyl-3,8-dioxo-1-(2-thienyl)-4-oxa-2,7,9-triazadodecan-12-oate; methyl(6S,10S)-2-(4-azidoobenzyl)-10-(1,3-benzodioxol-5-yl)-6-butyl-3,8-dioxo-1-(2-thienyl)-4-oxa-2,7,9-triazadodecan-12-oate; (2S)-2-[(tert-butoxycarbonyl)amino]hexyl phenyl(2-thienylmethyl)carbamate; methyl(6S,10S)-10-(1,3-benzodioxol-5-yl)-6-butyl-3,8-dioxo-2-phenyl-1-(2-thienyl)-4-oxa-2,7,9-triazadodecan-12-oate; tert-butyl[(2S)-1-{[bis(3-thienylmethyl)carbamoyl]oxy}hexan-2-yl]carbamate; methyl(6S,10S)-10-(1,3-benzodioxol-5-yl)-6-butyl-3,8-dioxo-1-(3-thienyl)-2-(3-thienylmethyl)-4-oxa-2,7,9-triazadodecan-12-oate; benzyl[(5S)-5-[(tert-butoxycarbonyl)amino]-6-{[butyl(2-thienylmethyl)carbamoyl]oxy}hexyl] carbamate; (2S)-2-[(tert-butoxycarbonyl)amino]hexyl butyl (2-thienylmethyl)carbamate; methyl(3S,7S)-3-(1,3-benzodioxol-5-yl)-7-butyl-5,10-dioxo-11-(2-thienylmethyl)-9-oxa-4,6,11-triazapentadecan-1-oate; benzyl[(5S)-5-[(tert-butoxycarbonyl)amino]-6-{[(2-methoxyethyl)(2-thienylmethyl)carbamoyl]oxy}hexyl]carbamate; (2S)-2-{[(4-bromobenzyl)carbamoyl]amino}hexyl bis(2-thienylmethyl)carbamate; (2S)-2-{[(4-azidobenzyl)carbamoyl]amino}hexyl bis(2-thienylmethyl)carbamate; tert-butyl[(2S)-1-{[bis(2-thienylmethyl)carbamoyl]thio}hexan-2-yl]carbamate; and methyl(6S,10S)-10-(1,3-benzodioxol-5-yl)-6-butyl-3,8-dioxo-1-(2-thienyl)-2-(2-thienylmethyl)-4-thia-2,7,9-triazadodecan-12-oate.

In some embodiments, a method of enhancing binding of cells to an integrin-binding ligand is provided, wherein an agonist of integrin is a compound selected from the group consisting of benzyl{(5R)-5-[(tert-butoxycarbonyl)amino]-6-[(3-methoxybenzyl)(2-thienylmethyl)amino]-6-oxohexyl}carbamate; benzyl{(5R)-6-[bis(3-methoxybenzyl)amino]-5-[(tert-butoxycarbonyl)amino]-6-oxohexyl}carbamate; benzyl{(5S)-6-[bis(4-methoxybenzyl)amino]-5-[(tert-butoxycarbonyl)amino]-6-oxohexyl}carbamate; benzyl{(5S)-5-[(tert-butoxycarbonyl)

amino]-6-oxo-6-[(pyridin-3-ylmethyl)(2-thienylmethyl) amino]hexyl}carbamate; benzyl{(5S)-5-[(tert-butoxycarbonyl)amino]-6-oxo-6-[(pyridin-4-ylmethyl)(2-thienylmethyl)amino]hexyl}carbamate; (2S)-2-[methyl (phenylsulfonyl)amino]-N,N-bis(2-thienylmethyl) hexanamide; (2S)-2-({[3-(4-methoxyphenoxy)propyl] sulfonyl}amino)-N,N-bis(2-thienylmethyl)hexanamide; benzyl{(5R)-6-[bis(2-thienylmethyl)amino]-5-[(tert-butoxycarbonyl)amino]-6-oxohexyl}carbamate; benzyl{(5S)-6-[bis(2-thienylmethyl)amino]-5-[(tert-butoxycarbonyl) amino]-6-oxohexyl}carbamate; benzyl{(5S)-6-[bis(2-thienylmethyl)amino]-6-oxo-5-[(2-thienylsulfonyl)amino] hexyl}carbamate; tert-butyl{(2S)-1-[bis(2-thienylmethyl) amino]-1-oxo-6-[(2-thienylsulfonyl)amino]hexan-2-yl}carbamate; 6-[methyl(2-thienylsulfonyl)amino]-N,N-bis (2-thienylmethyl)hexanamide; 6-[(2-thienylacetyl)amino]-N,N-bis(2-thienylmethyl)hexanamide; benzyl{(4S)-5-[bis (2-thienylmethyl)amino]-4-[(tert-butoxycarbonyl)amino]-5-oxopentyl}carbamate; benzyl[(5S)-5-[(tert-butoxycarbonyl) amino]-6-oxo-6-{(2-thienylmethyl) [2-(trifluoromethyl) benzyl]amino}hexyl]carbamate; benzyl[(5S)-5-[(tert-butoxycarbonyl)amino]-6-oxo-6-{(2-thienylmethyl) [2-(trifluoromethoxy)benzyl]amino}hexyl]carbamate; benzyl [(5S)-5-[(tert-butoxycarbonyl)amino]-6-{[2-(difluoromethoxy)benzyl](2-thienylmethyl)amino}-6-oxohexyl]carbamate; tert-butyl{6-[bis(4-methoxybenzyl) amino]-6-oxohexyl}carbamate; N-{6-[bis(4-methoxybenzyl)amino]-6-oxohexyl}-4-methoxy-N-(4-methoxybenzyl)benzamide; N-{6-[bis(2-thienylmethyl) amino]-6-oxohexyl}-N-methylthiophene-2-carboxamide; 6-[(3-methoxybenzyl)(2-thienylacetyl)amino]-N,N-bis(2-thienylmethyl)hexanamide; methyl(3S)-3-(1,3-benzodioxol-5-yl)-3-[({4-[bis(2-thienylmethyl)amino]-4-oxobutyl}carbamoyl)amino]propanoate; 6-{[(3-chloropropyl)sulfonyl]amino}-N,N-bis(4-methoxybenzyl) hexanamide; 3-{[bis(2-thienylmethyl)carbamoyl]amino}-N,N-bis(2-thienylmethyl)propanamide; 3-{butyl[(2-thienylmethyl)carbamoyl]amino}-N,N-bis(2-thienylmethyl) propanamide; benzyl{(5S)-6-[bis(2-thienylmethyl)amino]-5-cyano-6-oxohexyl}carbamate; benzyl{(5R)-5-azido-6-[bis(2-thienylmethyl)amino]-6-oxohexyl}carbamate; and benzyl{(5S)-6-[bis(3-thienylmethyl)amino]-5-[(tert-butoxycarbonyl)amino]-6-oxohexyl}carbamate.

In other embodiments, a method of enhancing binding of cells to an integrin-binding ligand is provided, wherein an agonist of integrin is a compound selected from the group consisting of N-(3-methoxybenzyl)-N,N',N'-tris(2-thienylmethyl)pentanediamide; N-[2-(2-thienyl)ethyl]-N,N',N'-tris (2-thienylmethyl)pentanediamide; N,N-bis(3-methoxybenzyl)-N',N'-bis(2-thienylmethyl)pentanediamide; N,N-bis (pyridin-4-ylmethyl)-N',N'-bis(2-thienylmethyl) pentanediamide; N,N,N',N'-tetrakis(2-thienylmethyl) hexanediamide; N,N,N',N'-tetrakis(3-methoxybenzyl) hexanediamide; N,N,N',N'-tetrakis(4-methoxybenzyl) hexanediamide; (3E)-N,N,N',N'-tetrakis(2-thienylmethyl) hex-3-enediamide; N,N,N',N'-tetrakis(2-thienylmethyl) pentanediamide; N,N,N',N'-tetrakis(4-methoxybenzyl) pentanediamide; 2,2'-oxybis[N,N-bis(2-thienylmethyl) acetamide]; N,N,N',N'-tetrakis(2-thienylmethyl) octanediamide; N,N,N',N'-tetrakis(2-thienylmethyl) heptanediamide; 3-oxo-1-(2-thienyl)-2-(2-thienylmethyl)-4, 7,10-trioxa-2-azadodecan-12-yl bis(2-thienylmethyl) carbamate; 2,2'-(1,3-phenylene)bis[N,N-bis(2-thienylmethyl)acetamide]; N,N,N',N'-tetrakis(4-methoxybenzyl)heptanediamide; N,N,N',N'-tetrakis(4-methoxybenzyl)succinamideethane-1,2-diyl bis[bis(2-thienylmethyl)carbamate]; N,N,N',N'-tetrakis(4-methoxybenzyl)octanediamide; N,N,N',N'-tetrakis(2-thienylmethyl)pyridine-3,5-dicarboxamide; N,N,N',N'-tetrakis(2-thienylmethyl)pyridine-2,6-dicarboxamide; N,N, N',N'-tetrakis(2-thienylmethyl)pyridine-2,4-dicarboxamide; 2,2'-(1,4-phenylene)bis[N,N-bis(2-thienylmethyl)acetamide]; and N,N'-bis(4-methoxybenzyl)-N,N'-bis(2-thienylmethyl)hexanediamide.

In another embodiment, a method of enhanced binding of integrin-expressing cells to an integrin-binding ligand utilizes an integrin agonist compound selected from the group consisting of methyl(2S)-6-{[(benzyloxy)carbonyl]amino}-2-[benzyl(phenylsulfonyl)amino]hexanoate; methyl(2S)-6-{[(benzyloxy)carbonyl]amino}-2-[benzyl(2-thienylsulfonyl)amino]hexanoate; methyl(2S)-6-{[(benzyloxy) carbonyl]amino}-2-[(2-thienylacetyl)(2-thienylmethyl) amino]hexanoate; methyl(2S)-6-{[(benzyloxy)carbonyl] amino}-2-[(2-thienylcarbonyl)(2-thienylmethyl)amino] hexanoate; benzyl{(5S)-5-[(tert-butoxycarbonyl)amino]-6-[(2-thienylmethyl)(2-thienylsulfonyl)amino] hexyl}carbamate; benzyl{(5S)-5-[(tert-butoxycarbonyl) amino]-6-[(phenylsulfonyl)(2-thienylmethyl)amino] hexyl}carbamate; benzyl{(5S)-5-[(tert-butoxycarbonyl) amino]-6-[(2-thienylacetyl)(2-thienylmethyl)amino] hexyl}carbamate; benzyl{(5S)-5-[(tert-butoxycarbonyl) amino]-6-[(methylsulfonyl)(2-thienylmethyl)amino] hexyl}carbamate; benzyl{(5S)-5-[(tert-butoxycarbonyl) amino]-6-[(2-thienylcarbonyl)(2-thienylmethyl)amino] hexyl}carbamate; benzyl[(5S)-5-[(tert-butoxycarbonyl) amino]-6-{[(4-methoxyphenyl)sulfonyl](2-thienylmethyl) amino}hexyl]carbamate; benzyl{(5S)-5-[(tert-butoxycarbonyl)amino]-6-[(4-methoxybenzoyl)(2-thienylmethyl)amino]hexyl}carbamate; N,N'-heptane-1,7-diylbis[N-(2-thienylmethyl)thiophene-2-carboxamide]; N,N'-heptane-1,7-diylbis[N-(2-thienylmethyl)benzamide; N,N'-hexane-1,6-diylbis[N-(2-thienylmethyl)thiophene-2-carboxamide]; N,N'-hexane-1,6-diylbis[N-(3-methoxybenzyl)thiophene-2-carboxamide]; tert-butyl{5-[(4-methoxybenzyl)(2-thienylsulfonyl)amino]pentyl}carbamate; N-(3-methoxybenzyl)-N-{5-[(2-thienylsulfonyl)amino] pentyl}thiophene-2-sulfonamide; tert-butyl{(2S)-1,6-bis [bis(2-thienylmethyl)amino]-1,6-dioxohexan-2-yl}carbamate; tert-butyl{5-[(2-thienylcarbonyl)(2-thienylmethyl)amino]pentyl}carbamate; N-(3-methoxybenzyl)-N-{5-[(2-thienylcarbonyl)amino] pentyl}thiophene-2-carboxamide; and N,N'-pentane-1,5-diylbis[N-(3-methoxybenzyl)thiophene-2-carboxamide].

In a further embodiment, a method of enhanced binding of integrin-expressing cells to an integrin-binding ligand utilizes an integrin agonist compound selected from the group consisting of N-{2-[bis(2-thienylmethyl)sulfamoyl] ethyl}-N-(2-thienylmethyl)thiophene-2-carboxamide; 2-{butyl[(2-thienylmethyl)carbamoyl]amino}-N,N-bis(2-thienylmethyl)ethanesulfonamide; 2-[(methylsulfonyl)(2-thienylmethyl)amino]-N,N-bis(2-thienylmethyl)ethanesulfonamide; 2-{[bis(2-thienylmethyl)carbamoyl]amino}-N, N-bis(2-thienylmethyl)ethanesulfonamide; N-{2-[bis(2-thienylmethyl)sulfamoyl]ethyl}thiophene-2-sulfonamide; N-{2-[bis(2-thienylmethyl)sulfamoyl]ethyl}-2-(2-thienyl) acetamide; N-{2-[bis(2-thienylmethyl)sulfamoyl] ethyl}thiophene-2-carboxamide; N,N-bis(2-thienylmethyl)-2-{[(2-thienylmethyl)carbamoyl] amino}ethanesulfonamide; 2-({2-[bis(2-thienylmethyl) sulfamoyl]ethyl}amino)-N,N-bis(2-thienylmethyl) acetamide; 3-[{2-[bis(2-thienylmethyl)amino]-2-oxoethyl} (butyl)amino]-N,N-bis(2-thienylmethyl)propanamide; 2-[{2-[bis(2-thienylmethyl)sulfamoyl]ethyl}(methyl) amino]-N,N-bis(2-thienylmethyl)acetamide; 3-({2-[bis(2- thienylmethyl)sulfamoyl]ethyl}amino)-N,N-bis(2-thienylmethyl)propanamide; 3-({2-[bis(2-thienylmethyl)sulfamoyl]ethyl}amino)-N,N-bis(4-methoxybenzyl)propanamide; 2-(acetyl{2-[bis(2-thienylmethyl)sulfamoyl]ethyl}amino)-N,N-bis(2-thienylmethyl)acetamide; and 2-(acetyl{2-[bis(4-methoxybenzyl)sulfamoyl]ethyl}amino)-N,N-bis(2-thienylmethyl)acetamide.

In some embodiments, a method of enhancing binding of cells to an integrin-binding ligand is provided, wherein said agonist of integrin is a compound selected from the group consisting of tert-butyl[(2S)-1-{[bis(cyclopropylmethyl)carbamoyl]oxy}hexan-2-yl]carbamate; (2S)-2-[(tert-butoxycarbonyl)amino]hexyl diisobutylcarbamate; methyl(8S,12S)-12-(1,3-benzodioxol-5-yl)-8-butyl-4-isobutyl-2-methyl-5,10-dioxo-6-oxa-4,9,11-triazatetradecan-14-oate; and benzyl{(5S)-6-[bis(cyclopropylmethyl)amino]-5-[(tert-butoxycarbonyl)amino]-6-oxohexyl}carbamate.

In accordance with some embodiments, a method of enhancing binding of cells to an integrin-binding ligand is provided, which comprises treating integrin-expressing cells in vitro with an agonist of integrin, wherein said integrin-expressing cells are selected from the group consisting of adult stem cells, embryonic stem cells, progenitor cells, and induced pluripotent stem cells.

In some further embodiments of the above described method of enhancing binding of cells to an integrin-binding ligand, contacting the treated cells with an integrin-binding ligand includes contacting a surface comprising an integrin-binding ligand with the agonist-treated cells, to bind the agonist-treated cells to said surface, wherein binding of said agonist-treated cells is enhanced relative to binding of integrin-expressing cells not treated by this method.

In some embodiments of an above-described method, at least 3 fold more agonist-treated cells are bound to said surface than integrin-expressing cells not treated with said agonist. In some embodiments, the ligand-bearing surface is on a tissue comprising an integrin binding protein selected from the group consisting of vascular cell adhesion molecule-1 (VCAM-1), fibronectin, mucosal addressin cellular adhesion molecule-1 (MAdCAM-1), inter-cellular adhesion molecule-1 (ICAM-1), inter-cellular adhesion molecule-2 (ICAM-2) and vitronectin.

In some further embodiments, a method of enhancing retention of exogenously-introduced cells at an in vivo target site in a mammal, is provided, which comprises: (a) treating integrin-expressing cells in vitro with an agonist of integrin, wherein said agonist is an above identified compound; (b) introducing the agonist-treated cells to an in vivo target site in the mammal; and (c) causing a greater number of said introduced agonist-treated cells to remain at said target site relative to the number of cells retained if integrin-expressing cells not treated with said agonist were introduced to said target site.

In accordance with certain embodiments a method of treating damaged or diseased vascular tissue of a mammal is provided, which comprises: (a) administering to a damaged or diseased vascular site, including bone marrow, in a vessel of the mammal a plurality of agonist-treated integrin-expressing stem cells or progenitor cells treated according to the method described above, wherein said integrin selected from the group consisting of α4β1, α5β1, α4β7, αvβ3 and αLβ2; (b) causing a greater number of said administered agonist-treated cells to remain at said vascular site relative to the number of cells retained if integrin-expressing cells not treated with said agonist were administered to said damaged or diseased vascular site, wherein said site comprises cells bearing an integrin-binding ligand on a cell surface; and (c) allowing said cells at said vascular site to proliferate/differentiate and/or release paracrine factors.

These and other embodiments, features and advantages of the present invention will become apparent with reference to the following description.

DETAILED DESCRIPTION

Definitions

In addition to having their customary and usual meaning, the following definitions apply where the context permits in the specification and claims:

"Pharmaceutical composition" refers to a mixture of one or more chemicals, or pharmaceutically acceptable salts thereof, with a suitable carrier, for administration to a mammal as a medicine.

"Therapeutically effective amount" refers to that amount of the compound being administered that will relieve at least to some extent one or more of the symptoms of the disorder being treated. For example, an amount of the compound effective to prevent, alleviate or ameliorate symptoms of disease or prolong the survival of the subject being treated.

With respect to a disease or disorder, the term "treatment" refers to preventing, deterring the occurrence of the disease or disorder, arresting, regressing, or providing relief from symptoms or side effects of the disease or disorder and/or prolonging the survival of the subject being treated.

The term "alkyl" as used herein alone or in combination refers to $C_1$-$C_{12}$ straight or branched, substituted or unsubstituted saturated chain radicals derived from saturated hydrocarbons by the removal of one hydrogen atom. Representative examples of alkyl groups include methyl, ethyl, n-propyl, iso-propyl, n-butyl, sec-butyl, iso-butyl, and tert-butyl among others.

The term "alkenyl", alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl", alone or in combination, refers to a substituted or unsubstituted straight or substituted or unsubstituted branched chain alkynyl radical containing from 2 to 10 carbon atoms. Examples of such radicals include, but are not limited to ethynyl, propynyl, propargyl, butynyl, hexynyl, decynyl and the like.

The term "lower" modifying "alkyl", "alkenyl", "alkynyl" or "alkoxy" refers to a $C_1$-$C_6$ unit for a particular functionality. For example lower alkyl means $C_1$-$C_6$ alkyl.

The term "cycloalkyl" as used herein alone or in combination refers to a substituted or unsubstituted aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. This term is meant to encompass cycloalkenyl and cycloalkynyl groups. "Cycloalkyl" includes cis or trans forms. Furthermore, the substituents may either be in endo or exo positions in the bridged bicyclic systems.

The term "cycloalkenyl" as used herein alone or in combination refers to a cyclic carbocycle containing from 4 to 8 carbon atoms and one or more double bonds. Examples of such cycloalkenyl radicals include, but are not limited to, cyclopentenyl, cyclohexenyl, cyclopentadienyl and the like.

The term "cycloalkylalkyl" as used herein refers to a cycloalkyl group appended to a lower alkyl radical, including, but not limited to cyclohexyl methyl.

The term "halo" or "halogen" as used herein refers to I, Br, Cl or F.

The term "haloalkyl" as used herein refers to a lower alkyl radical, to which is appended at least one halogen substituent, for example chloromethyl, fluoroethyl, trifluoromethyl and pentafluoroethyl among others.

The term "alkoxy", alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy", alone or in combination, refers to a radical of formula alkenyl-O—, provided that the radical is not an enol ether, wherein the term "alkenyl" is as defined above. Examples of suitable alkenoxy radicals include, but are not limited to, allyloxy, E- and Z-3-methyl-2-propenoxy and the like.

The term "alkynoxy", alone or in combination, refers to a radical of formula alkynyl-O—, provided that the radical is not an -ynol ether. Examples of suitable alkynoxy radicals include, but are not limited to, propargyloxy, 2-butynyloxy and the like.

The term "carboxyl" as used herein refers to —$CO_2H$.

The term "thioalkoxy", refers to a thioether radical of formula alkyl-S—, wherein "alkyl" is as defined above.

The term "carboxaldehyde" as used herein refers to —C(O)R wherein R is hydrogen.

The term "carboxamide" as used herein refers to —C(O)$NR_2$ wherein R is hydrogen, alkyl or any other suitable substituent.

The term "alkoxyalkoxy" as used herein refers to $R_b$O—$R_c$O— wherein $R_b$ is lower alkyl as defined above and $R_c$ is alkylene wherein alkylene is —$(CH_2)_{n'}$— wherein n' is an integer from 1 to 6. Representative examples of alkoxyalkoxy groups include methoxymethoxy, ethoxymethoxy, and t-butoxymethoxy among others.

The term "alkylamino" as used herein refers to $R_d$ NH— wherein $R_d$ is a lower alkyl group, for example, ethylamino, butylamino, among others.

The term "alkenylamino" alone or in combination, refers to a radical of formula alkenyl-NH— or (alkenyl)$_2$ N—, wherein the term "alkenyl" is as defined above, provided that the radical is not an enamine. An example of such alkenylamino radicals is the allylamino radical.

The term "alkynylamino", alone or in combination, refers to a radical of formula alkynyl-NH— or (alkynyl)$_2$ N— wherein the term "alkynyl" is as defined above, provided that the radical is not an amine. An example of such alkynylamino radicals is the propargyl amino radical.

The term "dialkylamino" as used herein refers to $R_e$ $R_f$ N— wherein $R_e$ and $R_f$ are independently selected from lower alkyl, for example diethylamino, and methyl propylamino, among others.

The term "amino" as used herein refers to $H_2N$—.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, and isopropoxycarbonyl among others.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group selected from the group consisting of furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Arylalkyl" and "alkylaryl" employ the term "alkyl" as defined above. Rings may be multiply substituted. Aromatic rings may be fused with other aromatic or non-aromatic rings to form multicyclic rings, and are also encompassed by the term "aromatic," as used herein.

The term "aralkyl", alone or in combination, refers to an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "aralkenyl", alone or in combination, refers to an aryl substituted alkenyl radical, wherein the terms "aryl" and "alkenyl" are as defined above.

The term "arylamino", alone or in combination, refers to a radical of formula aryl-NRg-, wherein "aryl" is as defined above. Rg may be selected from the group consisting of H, lower alkyl, aryl and aralkyl among others. Examples of arylamino radicals include, but are not limited to, phenylamino(anilido), naphthlamino, 2-, 3-, and 4-pyridylamino and the like.

The term "biaryl", alone or in combination, refers to a radical of formula aryl-aryl, wherein the term "aryl" is as defined above.

The term "thioaryl", alone or in combination, refers to a radical of formula aryl-S—, wherein the term "aryl" is as defined above. An example of a thioaryl radical is the thiophenyl radical.

The term "aroyl", alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The term "heterocyclyl", alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxyl, alkoxycarbonyl, carboxyalkyl, oxo, arylsulfonyl and aralkylaminocarbonyl among others.

The term "alkylheterocyclyl" as used herein refers to an alkyl group as previously defined appended to the parent molecular moiety through a heterocyclyl group.

The term "heterocyclylalkyl" as used herein refers to a heterocyclyl group as previously defined appended to the parent molecular moiety through an alkyl group.

The term "aminal" as used herein refers to a hemi-acetal of the structure RCH($NH_2$)(OH).

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in ADVANCED ORGANIC CHEMISTRY by J. March, 1985, pp. 16-18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio and alkyldithio.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1-3 atoms containing any combination of —C—, —C(O)—, —NH—, —S—, —S(O)—, —O—, —C(O)O— or —S(O)O—. Rings may be substituted multiple times.

The term "mammals" includes humans and other animals.

The term "heteroatom" as used herein encompasses nitrogen, sulfur and oxygen.

The term "alpha" as used herein indicates the position immediately adjacent to the position described.

ABBREVIATIONS

The following abbreviations are used herein:
Ac acetyl
AcOH acetic acid
6-Ahx-OH 6-aminohexanoic acid
Bn benzyl
Boc tert-butyloxycarbonyl
nBu n-butyl
nBuLi n-butyllithium, 1.6M in hexanes (unless other concentration noted)
Cbz benzyloxycarbonyl
CDI N,N'-carbonyldiimidazole
COMU (1-cyano-2-ethoxy-2-oxoethylidenaminooxy)dimethylamino-morpholino-carbenium hexafluorophosphate
Dab 2,4-diaminobutyryl
DBU 1,8-diazabicyclo[5.4.0]undec-7-ene
DCE 1,2-dichloroethane
DCHA dicyclohexylamine
DCM dichloromethane (methlyene chloride)
dioxane 1,4-dioxane
DIPEA N,N-diisopropylethylamine
DMED N,N'-dimethylethylene diamine
DMF N,N-dimethylformamide
DMSO dimethylsulfoxide
Et ethyl
EtOH ethanol
Fmoc 9H-fluoren-9-ylmethyloxycarbonyl
Glu glutamic acid
Gly glycine
HBTU O-(Benzotriazol-1-yl)-N,N,N',N'-tetramethyluronium hexafluorophosphate
HMDS hexamethyldisilazane
iPr isopropyl
KHMDS potassium bis(trimethylsilyl)amide
Lys lysine
LHMDS lithium bis(trimethylsilyl)amide
Me methyl
MeOH methanol
Nle norleucine
NMM 4-methylmorpholine
NSMC N-succinimidyl-N-methylcarbamate
OAc acetate
Orn Ornithine
pTsOH para-toluenesulfonic acid
Ph phenyl
RT room temperature
tBu tert-butyl
TEA triethylamine
Tfa trifluoroacetyl
THF tetrahydrofuran
Tol toluene
Tyr tyrosine
Z benzyloxycarbonyl The inventors hypothesized that small molecule compounds which enhance integrin-mediated adhesion may be beneficial as therapeutic agents, and that some of those compounds may prove useful in many diseases or conditions that are amenable to cell-based therapy. Non-limiting examples of such diseases or conditions are myocardial infarction, heart failure, peripheral arterial disease, diabetes, renal failure, systemic lupus erythematosus, multiple sclerosis, pulmonary fibrosis, pulmonary hypertension, acute respiratory distress syndrome, Alzheimer's disease, Huntington's disease, Parkinson's disease, spinal cord injury, infertility, and bone marrow transplant. Accordingly, a group of chemical compounds have been synthesized which enhance the integrin-mediated binding of cells to their respective ligands. Integrins targeted by these compounds include, but are not limited to, $\alpha 4\beta 1$, $\alpha 4\beta 7$, $\alpha 5\beta 1$, $\alpha L\beta 2$ and $\alpha V\beta 3$. Corresponding ligands include, but are not limited to, VCAM-1, fibronectin, MAdCAM-1, ICAM-1, ICAM-2 and vitronectin.

Agonist compounds, the ability of representative compounds to enhance binding of integrin-expressing cells, and therapeutic applications of agonist-treated cells are further described as follows.

Agonist Pre-Treated Cells

One or more integrin-expressing cells are first treated (pre-treated) with an agonist compound having the general formula I, as described herein, to form agonist-bound integrin molecules on the cell's surface. The integrin-expressing cells may be embryonic stem cells, adult stem/progenitor cells, or induced pluripotent stem cells, for example. In some cases, the cells express one or more of the integrins $\alpha 4\beta 1$, $\alpha 5\beta 1$, $\alpha 4\beta 7$, $\alpha v\beta 3$ and $\alpha L\beta 2$. The treatment of the cells generally includes contacting the integrin-expressing cells in vitro with the agonist. In most applications the agonist compound in present in the treatment media at a concentration in the range of about 100 nM to about 30 µM. In some cases the agonist concentration is in the range of about 1 µM to about 10 µM. After exposure to the agonist, the resulting agonist-treated cells have an enhanced ability to bind to a cognate ligand. The integrin is expressed on the surface of the cells, and may be either naturally occurring or transgenically expressed by a cell that has been transformed to express an exogenous integrin gene. The protein or other cognate ligand to which the integrin binds is expressed either on a cell surface or is part of the extracellular matrix.

Enhanced Binding of Pre-Treated Cells to Integrin-Binding Ligands

The agonist, as described herein, dissolved in a pharmaceutically acceptable diluent, is added to cell culture media or cell suspension and mixed. The resulting agonist-treated cells are introduced to an integrin-binding ligand or binding site, whereupon the treated cells bind, attach or adhere to the cognate ligands in solution, or on a surface or target tissue. In some cases an integrin binding protein is vascular cell adhesion molecule-1 (VCAM 1), fibronectin, mucosal addressin cellular adhesion molecule-1 (MAdCAM-1), intercellular adhesion molecule-1 (ICAM-1), intercellular adhesion molecule-2 (ICAM-2) or vitronectin. As a result of the agonist treatment, the binding of the agonist-treated cells to the ligand is enhanced or increased compared to binding of integrin-expressing cells not treated with the agonist. In some cases, at least 3 fold more agonist-treated cells are bound to a ligand-coated surface than untreated integrin-expressing cells. In some cases, up to 3 fold more agonist-treated cells than untreated cells are bound to an integrin binding protein.

Enhanced Retention of Pre-Treated Cells to Tissues Expressing Integrin-Binding Ligands Regardless of the cell type, mechanism of action, or how they are delivered, for many applications it is critical that the cells home to, and are retained in, a relevant injured tissue. Low levels of cell retention observed in animal models and clinical trials are considered one of the major impediments to the progress of cell-based therapies. Even when cells are injected locally, less than 10% of injected cells are typically retained after one hour and this number decreases over time in conventional cell-based therapies. The retention rates are even lower when delivered systemically. By comparison, many embodiments of the presently disclosed methods increase the rate of retention of exogenously delivered cells and will potentially greatly further efforts in regenerative medicine.

A method of enhancing retention of exogenously-introduced cells at an in vivo target site in a mammal generally includes (a) treating integrin-expressing cells in vitro with an agonist of integrin, wherein the agonist is a compound having the general formula I, as described herein; (b) introducing the agonist-treated cells to an in vivo target site in the mammal; and (c) causing a greater number of said introduced agonist-treated cells to remain at said target site relative to the number of cells retained if integrin-expressing cells not treated with said agonist were introduced to said target site. The target site includes an integrin binding protein such as vascular cell adhesion molecule-1 (VCAM 1), fibronectin, mucosal addressin cellular adhesion molecule-1 (MAdCAM-1), inter-cellular adhesion molecule-1 (ICAM-1), inter-cellular adhesion molecule-2 (ICAM-2) or vitronectin, for example.

Therapeutic Treatment of Damaged or Diseased Vascular Tissue

Agonist-treated cells prepared as described above are administered to a damaged or diseased vascular site in a vessel of a mammal. The cells are injected directly into, or around a site of damaged or diseased vascular tissue, as often occurs in tissue due to ischemia following a heart attack or in peripheral arterial disease. Alternatively, in some cases the agonist-treated cells are injected intravenously for homing to a damaged or diseased site where treatment is desired. The damaged or diseased tissue contains cells (e.g., endothelial cells) that express VCAM-1, and in which VCAM-1 exists on the cell surface. Expression of VCAM-1 is induced in many cases by inflammatory cytokines such as tumor necrosis factor-$\alpha$, interleukin-4 and interleukin-1$\beta$. In some instances, cells or extracellular matrix at or adjacent to a treatment site express and bear on their surface one or more other integrin-binding protein such as fibronectin, mucosal addressin cellular adhesion molecule-1 (MAdCAM-1), intercellular adhesion molecule-1 (ICAM-1), intercellular adhesion molecule-2 (ICAM-2) or vitronectin. In those instances, the injected agonist-treated cells adhere to the cognate ligands at the damaged or diseased tissue site, causing a greater number of the administered agonist-treated cells to remain at the treatment site compared to the number of untreated integrin-expressing cells that would be retained if administered instead. The agonist-treated cells retained at the treatment site are allowed to grow and/or release paracrine factors, to regenerate vascular tissue at the damaged or diseased site, e.g., damage due to ischemia, autoimmune reactions, or mechanical injury. Paracrine factors are substances released from a cell that have effects on a neighboring cell, such as growth factors or cytokines.

Cell-Based Therapies for Treatment of Other Diseases and Conditions

Use of the above-described agonist-treated cells for treatment of a number of diseases or conditions that are amenable to cell-based therapy is also contemplated in various embodiments. For example, myocardial infarction, peripheral artery disease, diabetes, renal failure, systemic lupus erythematosus, multiple sclerosis, pulmonary fibrosis, pulmonary hypertension, acute respiratory distress syndrome, Alzheimer's disease, Huntington's disease, Parkinson's disease, spinal cord injury, infertility and bone marrow transplant are treated in some embodiments by injecting an above-described cell suspension intravenously, intraarterially, or directly in or around the injured area. New tissue is generated either by proliferation and differentiation of the injected cells and/or release of paracrine factors by the injected cells which induce proliferation and differentiation of neighboring host cells.

The compounds and processes described herein will be better understood in connection with the following synthetic schemes which illustrate the methods by which the disclosed compounds may be prepared. A detailed description of the preparation of representative agonist compounds is set forth in the Examples. It should be understood that the same or similar synthetic methods may also be used to synthesize other agonist compounds disclosed herein. These Examples are presented to describe preferred embodiments and uses of the compounds and agonist-treated cells, and are not meant to limit the invention unless otherwise stated in the claims appended hereto.

EXAMPLES

Materials

Reagents and Cell Lines

CS1 conjugated BSA (CS1-BSA) was purchased from New England Peptide (Gardner, Mass.). Serum fibronectin and vitronectin were purchased from Sigma-Aldrich (St. Louis, Mo.). Human MAdCAM-1 Fc chimera, ICAM-1 Fc chimera, and VCAM-1 were purchased from R&D Systems (Minneapolis, Minn.). K562, HUVEC, HSB and Jurkat cell lines were obtained from ATCC (Manassus, Va.) and maintained in recommended culture media. The K562 $\alpha4\beta1$ cell line was developed by electroporation of full length integrin $\alpha4$ cDNA (1) into wild-type K562 cells. After drug selection in geneticin (1 mg/ml), cells were sorted by FACS for $\alpha4$ integrin expression using the mAb HP2/1 then single cell cloned by limiting dilution. One clone (K562-$\alpha4\beta1$) was picked for high expression of integrin $\alpha4$, and specific cell adhesion to VCAM-1 was verified with function blocking $\alpha4$ and $\beta1$ mAb HP2/1 and 33B6 (2) respectively (data not shown). K562-$\alpha4\beta7$ was generated by co-transfecting K562 cells with $\alpha4$ cDNA and full length $\beta7$ cDNA (purchased from Origene Technologies and sequence verified) in pIRES2-EGFP (Clontech). After drug selection in kanamycin (30 ug/ml), cells were sorted based on EGFP expression by FACS, followed by sorting based on $\alpha4$ and $\beta7$ expression using conjugated mAb 9F10 and FIB504 (BD Biosciences, San Jose, Calif.), respectively. Clonal lines were developed as described for the K562-$\alpha4\beta1$ line. All reagents used in the synthesis of compounds were commercially available from common vendors. Compound names were generated with ACD Labs ACD/Name Chemist Version Release 12.00, Product Version 12.01.

Example 1

Preparation of 1-(2-thienyl)-N-(2-thienylmethyl)methanamine hydrochloride (1-1)

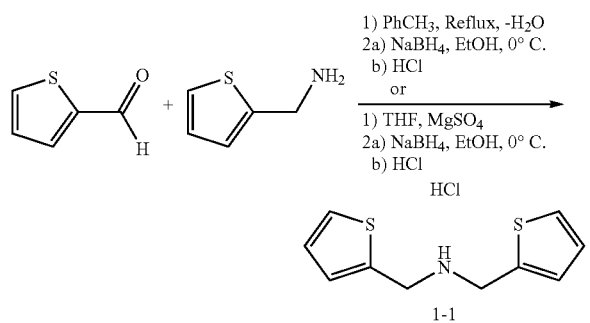

I. Method A

To a solution of 2-thiophenemethylamine (3.87 g, 34.5 mmol) in toluene (69 mL), 2-thiophenecarboxaldehyde (3.90 g, 34.5 mmol) was added. The resulting solution was heated at vigorous reflux for 1.75 hours while removing the water formed by means of a Dean-Stark trap. The resulting mixture was cooled to room temperature and concentrated under reduced pressure. The residue was dissolved in anhydrous ethanol (69 mL), the mixture was cooled to 0° C., and sodium borohydride (2.71 g, 69 mmol) was added in portions over the course of 30 minutes. The mixture was allowed to warm to room temperature overnight, was poured over ice, and acidified slowly with aqueous hydrochloric acid (2N). The precipitate was filtered and dried under vacuum to give the title compound 1-1 as an off-white to tan solid (5.35 g).

Alternately, the starting free amine could be generated from the amine hydrochloride by extracting with three portions of ethyl acetate from aqueous sodium bicarbonate with methanol added for solubility. The organic layers were combined, dried, filtered and concentrated. This variation was used to prepare 1-(4-nitrophenyl)-N-(2-thienylmethyl)methanamine hydrochloride (1-27) from 4-nitrobenzylamine hydrochloride.

II. Method B

To a solution of 2-thiophenemethylamine (4.10 g, 36.6 mmol) and 2-thiophenecarboxaldehyde (4.12 g, 36.7 mmol) in tetrahydrofuran (20 mL), anhydrous magnesium sulfate (6.9 g) was added. The mixture was heated to 50° C. for 3 hours. The mixture was cooled to room temperature and filtered, washing with ethanol (40 mL) and diethyl ether (40 mL). Sodium borohydride (2.00 g, 52.9 mmol) was added in three portions at room temperature and the mixture was stirred for 2 hours. The mixture was acidified with aqueous hydrochloric acid (2N) and the resulting precipitate was collected (three crops) by filtration and dried under vacuum to give the title compound 1-1 as a white solid (7.78 g).

This procedure was also used to prepare: 1-(4-bromophenyl)-N-(2-thienylmethyl)methanamine hydrochloride (1-45) from 4-bromobenzylamine and 2-thiophenecarboxaldehyde; 1-(3-thienyl)-N-(3-thienylmethyl)methanamine hydrochloride (1-50) from 3-thiophenemethylamine and 3-thiophenecarboxaldehyde; and tert-butyl{5-[(2-thienylmethyl)amino]pentyl}carbamate (5-34) from N-Boc-cadaverine and 2-thiophenecarboxaldehyde.

Alternately, an isolated hydrochloride salt could be converted to the freebase by partitioning between ethyl acetate or dichloromethane and saturated sodium bicarbonate, washing the organic layer with water and brine, drying over magnesium sulfate, filtering and concentrating. This variation was used to prepare: 1-(3-thienyl)-N-(3-thienylmethyl)methanamine (1-47) from 1-50; N-(4-methylbenzyl)-1-(4-methylphenyl)methanamine (1-43) from 4-methylbenzylamine and p-tolualdehyde; N-(4-chlorobenzyl)-1-(4-chlorophenyl)methanamine (1-44) from 4-chlorobenzylamine and 4-chlorobenzaldehyde; 1-(4-bromophenyl)-N-(2-thienylmethyl)methanamine (1-46) from 1-45; 1-cyclopropyl-N-(cyclopropylmethyl)methanamine (1-48) from cyclopropanecarboxaldehyde and cyclopropylmethylamine; and 1-cyclopropyl-N-(2-thienylmethyl)methanamine (1-49) from cyclopropanemethylamine and 2-thiophenecarboxaldehyde.

Example 2

Preparation of 1-(3-methoxyphenyl)-N-(2-thienylmethyl)methanamine hydrochloride (1-2)

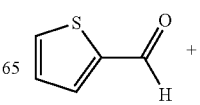

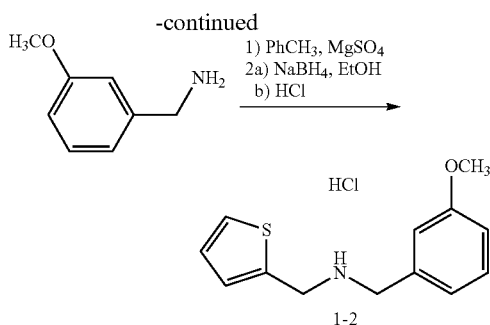

To a solution of 3-methoxybenzylamine (1.37 g, 9.99 mmol) and 2-thiophenecarboxaldehyde (1.12 g, 10.0 mmol) in toluene (10 mL), anhydrous magnesium sulfate (2 g) was added. The mixture was allowed to stand overnight at room temperature and sodium borohydride (0.5 g, 13 mmol) was added followed by ethanol (10 mL). The resulting mixture was stirred for 3 hours and acidified with aqueous hydrochloric acid (2N). The resulting precipitate was filtered and dried under vacuum to give the title compound 1-2 as a white solid (1.19 g).

This procedure was also used to prepare: N-(3-methoxybenzyl)-1-(3-methoxyphenyl)methanamine hydrochloride (1-3) from 3-methoxybenzylamine and 3-methoxybenzaldehyde; and 2-(2-thienyl)-N-(2-thienylmethyl)ethanamine hydrochloride (1-5) from 2-thiopheneethylamine and 2-thiophenecarboxaldehyde.

Alternately, tetrahydrofuran could be used in place of toluene. This variation was used to prepare N-(4-methoxybenzyl)-1-(4-methoxyphenyl)methanamine hydrochloride (1-6) from 4-methoxybenzylamine and 4-methoxybenzaldehyde. This variation was further modified by not adding ethanol to the reaction after adding the sodium borohydride. This modification was used to prepare: N-[4-(trifluoromethoxy)benzyl]-1-[4-(trifluoromethoxy)phenyl]methanamine hydrochloride (1-41) from 4-(trifluoromethoxy)benzylamine and 4-(trifluoromethoxy)benzaldehyde; and 1-(4-methoxyphenyl)-N-(2-thienylmethyl)methanamine hydrochloride (1-42) from 4-methoxybenzylamine and 2-thiophenecarboxaldehyde (solid sodium chloride added to acidified mixture to aid precipitation).

In another variation, when no precipitate formed upon acidifying, the aqueous layer was made basic with aqueous sodium hydroxide and extracted with dichloromethane or diethyl ether. The extract was washed with brine, dried, filtered, and concentrated, to give the free amine. This variation was used to prepare: N-(2-thienylmethyl)butan-1-amine (1-9) from 2-thiophenemethylamine and butyraldehyde; 1-(2-furyl)-N-(2-thienylmethyl)methanamine (1-10) from 2-aminomethylfuran and 2-thiophenecarboxaldehyde; 1-(2-furyl)-N-(2-furylmethyl)methanamine (1-11) from 2-aminomethylfuran and 2-furaldehyde; 2-methoxy-N-(2-thienylmethyl)ethanamine (1-12) from 2-methoxyethylamine and 2-thiophenecarboxaldehyde; and 3-[(2-thienylmethyl)amino]propan-1-ol (1-13) from 3-amino-1-propanol and 2-thiophenecarboxaldehyde. This variation was further modified by not adding ethanol to the reaction in tetrahydrofuran after adding the sodium borohydride. This modification was used to prepare: 1-(2-thienyl)-N-[2-(trifluoromethyl)benzyl]methanamine (1-38) from 2-thiophenemethylamine and 2-(trifluoromethyl)benzaldehyde; 1-(2-thienyl)-N-[2-(trifluoromethoxy)benzyl]methanamine (1-39) from 2-thiophenemethylamine and 2-(trifluoromethoxy)benzaldehyde; and 1-[2-(difluoromethoxy)phenyl]-N-(2-thienylmethyl)methanamine (1-40) from 2-thiophenemethylamine and 2-(difluoromethoxy)benzaldehyde.

The free amines prepared according to the procedure of the previous variation could also be taken up in aqueous hydrochloric acid and concentrated to give the hydrochloride salts. This method was used to isolate: 1-(pyridin-3-yl)-N-(2-thienylmethyl)methanamine dihydrochloride (1-4) from 3-aminomethylpyridine and 2-thiophenecarboxaldehyde in toluene; 1-(pyridin-3-yl)-N-(pyridin-3-ylmethyl)methanamine trihydrochloride (1-7) from 3-(aminomethyl)pyridine and 3-pyridinecarboxaldehyde in tetrahydrofuran; 1-(pyridin-4-yl)-N-(pyridin-4-ylmethyl)methanamine trihydrochloride (1-8) from 4-(aminomethyl)pyridine and 4-pyridinecarboxaldehyde in tetrahydrofuran; and 1-(pyridin-4-yl)-N-(2-thienylmethyl)methanamine dihydrochloride (1-15) from 4-aminomethylpyridine and 2-thiophenecarboxaldehyde in toluene.

In yet another variation, a diamine was used in place of the amine, reacting with 2.25 equivalents aldehyde and excess sodium borohydride in tetrahydrofuran. Upon acidifying, sodium chloride was added to the aqueous mixture to help precipitate the product. This procedure was used to prepare: N,N'-bis(2-thienylmethyl)heptane-1,7-diamine dihydrochloride (5-19) from 1,7-heptanediamine and 2-thiophenecarboxaldehyde; N,N'-bis(2-thienylmethyl)hexane-1,6-diamine dihydrochloride (5-25) from hexamethylenediamine and 2-thiophenecarboxaldehyde; and N,N'-bis(3-methoxybenzyl)hexane-1,6-diamine dihydrochloride (5-27) from hexamethylenediamine and 3-methoxybenzaldehyde.

Example 3

Preparation of
4-{[(2-thienylmethyl)amino]methyl}phenol
hydrochloride (1-14)

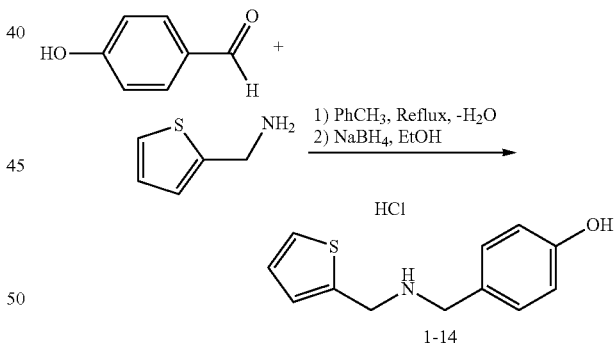

A solution of 4-hydroxybenzaldehyde (0.65 g, 5.2 mmol) and 2-thiophenemethylamine (0.59 g, 5.3 mmol) in toluene (25 mL) was heated at vigorous reflux for 4 hours while removing the water formed by means of a Dean-Stark trap. The resulting mixture was cooled to room temperature, sodium borohydride (excess) and ethanol (excess) were added, and the mixture was stirred overnight. The mixture was acidified with aqueous hydrochloric acid (2N) and warmed gently until gas evolution ceased. The solution was adjusted to pH 6-7 and extracted with dichloromethane (3 times). The organic layers were combined, washed with brine, dried, filtered and concentrated under reduced pressure to give the title compound 1-14 as an orange oil (0.44 g).

Example 14

Preparation of methyl(3S)-3-(1,3-benzodioxol-5-yl)-3-{[(4-nitrophenoxy)carbonyl]amino}propanoate (1-19)

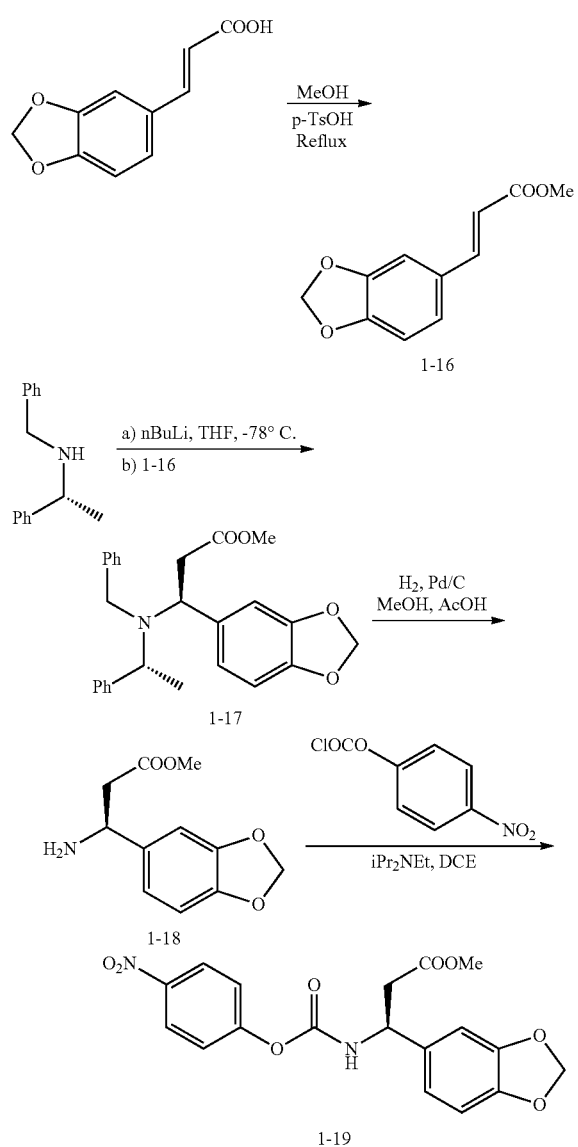

I. Methyl(2E)-3-(1,3-benzodioxol-5-yl)acrylate (1-16)

To a solution of 3,4-(methylenedioxy)cinnamic acid (6.2 g, 32 mmol) in methanol (0.4 L), p-toluenesulfonic acid hydrate (0.28 g, 1.5 mmol) was added. The reaction was heated to reflux overnight, concentrated under reduced pressure (to approximately 0.1 L), diluted with hot ethyl acetate, and washed with water (3 times) and saturated brine. The organic layer was dried over magnesium sulfate, filtered, and concentrated under reduced pressure. The residue was recrystallized from tert-butyl methyl ether/methanol to give the title compound 1-16 as a colorless powder (5.35 g).

Alternately, the ethyl ester could be prepared by using ethanol instead of methanol. This variation was used to prepare ethyl(2E)-3-(1,3-benzodioxol-5-yl)acrylate (1-35).

II. Methyl(3S)-3-(1,3-benzodioxol-5-yl)-3-{benzyl[(1R)-1-phenylethyl]amino}propanoate (1-17)

To a solution of (R)-(+)-N-benzyl-α-methylbenzylamine (6.14 g, 29.1 mmol) in tetrahydrofuran (78 mL) cooled to −78° C. under a nitrogen atmosphere, n-butyllithium (1.6 M in hexanes, 15.7 mL, 25.2 mmol) was added dropwise over 30 minutes. Upon completion of the butyl lithium addition, a solution of 1-16 (3.43 g, 16.6 mmol) in tetrahydrofuran (70 mL) was added dropwise over 30 minutes. The resulting solution was stirred at −78° C. for 4 hours, methanol (8 mL) was added and the mixture was poured onto saturated aqueous ammonium chloride. The resulting mixture was extracted with ethyl acetate (3 times), and the organic layers were combined, washed with brine, dried over magnesium sulfate (anhydrous), filtered and concentrated under reduced pressure. The residue was purified by chromatography on silica gel, eluting with hexanes:ethyl acetate (30:1 to 19:1) to give the title compound 1-17 (5.71 g).

Alternately, (S)-(−)-N-benzyl-α-methylbenzylamine could be used in place of (R)-(+)-N-benzyl-α-methylbenzylamine in step 11 to give the opposite configuration of the chiral centers. This procedure was used to prepare: ethyl (3R)-3-(1,3-benzodioxol-5-yl)-3-{benzyl[(1S)-1-phenylethyl]amino}propanoate (1-36) from 1-35; and methyl(3R)-3-(1,3-benzodioxol-5-yl)-3-{benzyl[(1S)-1-phenylethyl]amino}propanoate (1-28) from 1-16.

III. Methyl(3S)-3-amino-3-(1,3-benzodioxol-5-yl)propanoate (1-18)

To a solution of 1-17 (4.73 g, 11.3 mmol) in methanol (75 mL), glacial acetic acid (0.4 mL), palladium metal on carbon (Degussa type E101 NE/W, 50% $H_2O$, 10% Pd dry weight basis, 1.8 g, 0.83 mmol Pd). The atmosphere was replaced with hydrogen (toggling between vacuum and hydrogen from a balloon several times) and the reaction was stirred overnight. The mixture was filtered through Celite® and the filtrate was concentrated under reduced pressure. The residue was brought up in ethyl acetate, washed with saturated aqueous sodium carbonate, and the organic layer was dried over magnesium sulfate, filtered, and concentrated under reduced pressure to give the title compound 1-18 as a pale yellow oil (2.1 g).

This procedure was also used to prepare: ethyl(3R)-3-amino-3-(1,3-benzodioxol-5-yl)propanoate (1-20) from 1-36; and methyl(3R)-3-amino-3-(1,3-benzodioxol-5-yl)propanoate (1-29) from 1-28.

IV. Methyl(3S)-3-(1,3-benzodioxol-5-yl)-3-{[(4-nitrophenoxy)carbonyl]amino}propanoate (1-19)

To a solution of the 4-nitrophenylchloroformate (1.28 g, 6.35 mmol) and N,N-diisopropylethylamine (1.46 mL, 8.4 mmol) in dichloroethane (50 mL) cooled to 0° C., a solution of 1-18 (1.3 g, 5.6 mmol) in dichloroethane (11 mL) was added by syringe. The ice bath was removed and the reaction was stirred overnight and concentrated under reduced pressure. The residue was taken up in ethyl acetate and washed with water and saturated aqueous sodium bicarbonate. The organic layer was dried over magnesium sulfate, filtered and concentrated under reduced pressure. The residue was purified by chromatography on silica gel, eluting with hexanes: ethyl acetate (9:1 to 2:1) to give the title compound 1-19 as a yellow oil (0.92 g).

For this procedure or any of the following variations, an amine hydrochloride with additional equivalent of tertiary amine base may be used in place of the amine.

This procedure was used to prepare: ethyl(3R)-3-(1,3-benzodioxol-5-yl)-3-{[(4-nitrophenoxy)carbonyl]amino}propanoate (1-21) from 1-20; benzyl{(2S)-1-[bis(2-thienylmethyl)amino]-1-oxohexan-2-yl}carbamate (3-54) from 3-13 and benzylchloroformate; benzyl{(5S)-6-[bis(2-thienylmethyl)amino]-5-[(ethoxycarbonyl)amino]-6-oxohexyl}carbamate (3-76) from 3-66.HCl and ethyl chloroformate; and benzyl{(2S)-6-{[(benzyloxy)carbonyl]amino}-1-[bis(2-thienylmethyl)amino]-1-oxohexan-2-yl}carbamate (3-77) from 3-66 and benzylchloroformate.

Alternately, dichoromethane or tetrahydrofuran can be used in place of dichloroethane. This variation was used to prepare: 4-nitrophenyl bis(2-thienylmethyl)carbamate (1-33) from 1-1 in tetrahydrofuran; 4-nitrophenyl[(2S)-1-{[bis(2-thienylmethyl)carbamoyl]oxy}hexan-2-yl]carbamate (2-10) from 2-4 in dichloromethane; and benzyl{6-[bis(2-thienylmethyl)amino]-6-oxohexyl}carbamate (3-113) from 3-103 and benzyl chloroformate in dichloromethane.

In another variation, pyridine was used in place of N,N-diisopropylethylamine. This variation was used to prepare: methyl(3R)-3-(1,3-benzodioxol-5-yl)-3-{[(4-nitrophenoxy)carbonyl]amino}propanoate (1-32) from 1-29; 4-nitrophenyl{(2S)-1-[bis(2-thienylmethyl)amino]-1-oxohexan-2-yl}carbamate (3-44) from 3-13 in dichloromethane; benzyl [(5S)-6-[bis(2-thienylmethyl)amino]-5-{[(4-nitrophenoxy)carbonyl]amino}-6-oxohexyl]carbamate (3-67) from 3-66 in dichloroethane; and (2S)-2-{[(4-nitrophenoxy)carbonyl]amino}hexyl(2-methoxyethyl)(2-thienylmethyl)carbamate (2-106) from 2-104 in dichloroethane;

In yet another variation, a bischloroformate was used in place of the chloroformate, reacting with 2 equivalents 1-1 and 6 equivalents of N,N-diisopropylethylamine in dichloromethane. This method was used to prepare: 3-oxo-1-(2-thienyl)-2-(2-thienylmethyl)-4,7,10-trioxa-2-azadodecan-12-yl bis(2-thienylmethyl)carbamate (6-20) from triethyleneglycol bischloroformate; and ethane-1,2-diyl bis[bis(2-thienylmethyl)carbamate](6-25) from ethylene(bischlorformate).

Example 5

Preparation of N-[3-(aminomethyl)phenyl]methanesulfonamide hydrochloride (1-25)

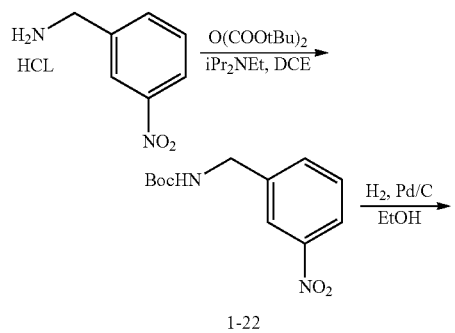

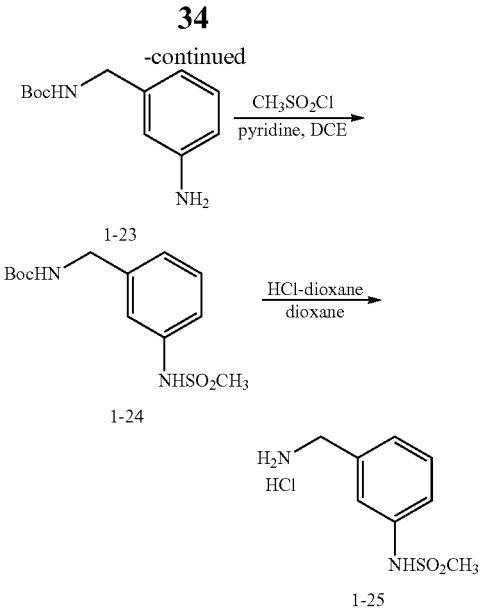

I. tert-Butyl(3-nitrobenzyl)carbamate (1-22)

To a solution of 3-nitrobenzylamine hydrochloride (0.847 g, 4.5 mmol) and N,N-diisopropylethylamine (4.0 mL, 23 mmol), in 1,2-dichloroethane (15 mL) at 0° C. and under a dry nitrogen atmosphere, a solution of di-tert-butyl dicarbonate (1.24 g, 5.7 mmol) in 1,2-dichloroethane (5 mL) was added. The reaction was allowed to warm to room temperature slowly, stirred overnight, diluted with 1:1 ethyl acetate:hexanes and washed with water, aqueous hydrochloric acid (1N), saturated aqueous sodium bicarbonate, water, and saturated brine. The organic layer was dried over magnesium sulfate, filtered, and concentrated under reduced pressure. The residue was purified by column chromatography on silica gel, eluting with hexanes:ethyl acetate (19:1 to 1:1) to give the title compound 1-22 as an off-white solid (1.1 g).

Alternately, a free amine can be used instead of the amine hydrochloride and the tertiary amine base, and tetrahydrofuran can be used instead of dichloroethane. This variation of this procedure was used to prepare tert-butyl(2-thienylmethyl)carbamate (2-30) from 2-thienylmethylamine.

In another variation, triethylamine and dichloromethane were used instead of N,N-diisopropylethylamine and dichloroethane. This variation was used to prepare methyl 4-[(tert-butoxycarbonyl)amino]butanoate (3-143) from 4-aminobutyric acid methyl ester hydrochloride.

II. tert-Butyl(3-aminobenzyl)carbamate (1-23)

To a solution of 1-22 (0.53 g, 2.10 mmol) in absolute ethanol (25 mL) under a dry nitrogen atmosphere, palladium metal on carbon (Degussa type E101 NE/W, 50% $H_2O$, 10% Pd dry weight basis, 0.22 g, 0.10 mmol Pd) was added. The atmosphere was replaced with hydrogen (toggle between vacuum and hydrogen from a balloon several times) and the reaction was stirred overnight, flushed with $N_2$, and filtered through Celite® filter agent, rinsing with ethanol. The filtrate was concentrated under reduced pressure to give the title compound 1-23 as dark brown syrup (0.38 g).

III. tert-Butyl{3-[(methylsulfonyl)amino]benzyl}carbamate (1-24)

To a solution of 1-23 (71 mg, 0.32 mmol) in pyridine (0.13 mL, 1.61 mmol) and 1,2-dichloroethane (0.4 mL), methanesulfonyl chloride (0.028 mL, 0.36 mmol) was added. The reaction was sealed and stirred at room temperature for 2 days, diluted with ethyl acetate, washed sequentially with water (3 times) and saturated brine. The organic layer was dried over magnesium sulfate, filtered, and concentrated under reduced pressure. The residue was purified by automated chromatography on silica gel, eluting with an ethyl acetate/hexanes gradient (10 to 100%) to give the title compound 1-24 as light yellow solid (72 mg).

IV. N-[3-(Aminomethyl)phenyl]methanesulfonamide hydrochloride (1-25)

To a solution of 1-24 (55 mg, 0.18 mmol) in 1,4-dioxane (0.5 mL), hydrogen chloride (4 M in 1,4-dioxane, 0.5 mL, 2 mmol) was added. The resulting mixture was stirred for 2 days and concentrated under reduced pressure to give the title compound 1-25 as an off-white solid (52 mg).

This procedure was also used to prepare: N-methyl-1-(2-thienyl)methanamine hydrochloride (2-32) from 2-31; (2S)-2-amino-6-{[(benzyloxy)carbonyl]amino}hexyl bis(2-thienylmethyl)carbamate hydrochloride (2-57) from 2-56; (2R)-2-aminohexyl bis(2-thienylmethyl)carbamate hydrochloride (2-61) from 2-60; 2-(methylamino)-N,N-bis(2-thienylmethyl)acetamide hydrochloride (3-17) from 3-9; benzyl {(5R)-5-amino-6-[bis(2-thienylmethyl)amino]-6-oxohexyl}carbamate hydrochloride (3-63) from 3-62; benzyl{(5S)-5-amino-6-[bis(2-thienylmethyl)amino]-6-oxohexyl}carbamate hydrochloride (3-66.HCl) from 3-65; benzyl[(5S)-6-[bis(2-thienylmethyl)amino]-5-(methylamino)-6-oxohexyl]carbamate hydrochloride (3-84) from 3-83; (2S)-2-aminohexyl bis(4-methoxybenzyl)carbamate hydrochloride (2-68) from 2-67; (2S)-2-aminohexyl dibenzylcarbamate hydrochloride (2-73) from 2-72; (2S)-2-aminohexyl bis(4-methylbenzyl)carbamate hydrochloride (2-77) from 2-76; (2S)-2-aminohexyl bis(4-chlorobenzyl)carbamate hydrochloride (2-81) from 2-80; (2S)-2-aminohexyl(4-bromobenzyl)(2-thienylmethyl)carbamate hydrochloride (2-85) from 2-84; 2S)-2-aminohexyl phenyl(2-thienylmethyl)carbamate hydrochloride (2-90) from 2-89; (2S)-2-aminohexyl bis(3-thienylmethyl)carbamate hydrochloride (2-94) from 2-93; (2S)-2-aminohexyl butyl(2-thienylmethyl)carbamate hydrochloride (2-99) from 2-98; (2S)-2-aminohexyl(2-methoxyethyl)(2-thienylmethyl)carbamate hydrochloride (2-104) from 2-103; (2S)-2-aminohexyl diisobutylcarbamate hydrochloride (2-115) from 2-114; and S-[(2S)-2-aminohexyl]bis(2-thienylmethyl)carbamothioate hydrochloride (2-119) from 2-118.

Example 6

Preparation of N-(2-thienylmethyl)aniline (1-30)

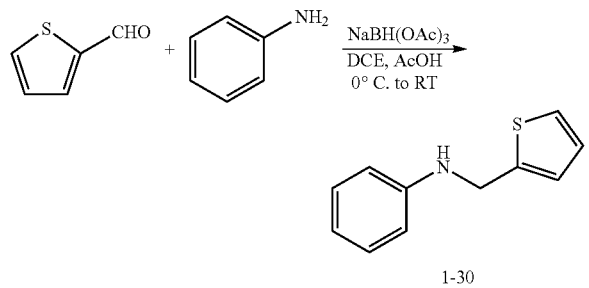

To a solution of aniline (186 mg, 2.0 mmol), 2-thiophenecarboxaldehyde (673 mg, 6.0 mmol), and acetic acid (0.7 mL, 12.0 mmol) in dichloroethane (7 mL) at 0° C., sodium triacetoxyborohydride (1.27 g, 6.0 mmol) was added. The ice bath was removed and the mixture was stirred overnight. The reaction was diluted with saturated aqueous sodium bicarbonate and extracted with ethyl acetate three times. The organic layers were combined, washed with water and brine (twice), dried over magnesium sulfate, filtered, and concentrated under reduced pressure to give the title compound 1-30 as an amber oil (135 mg).

Example 7

Preparation of 1-(6-methoxypyridin-3-yl)methanamine (1-31)

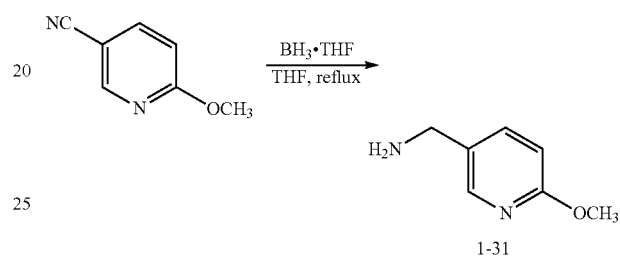

To a stirred solution of 2-methoxypyridine-5-carbonitrile (0.95 g, 7.1 mmol) in tetrahydrofuran (25 mL) under a dry nitrogen atmosphere, borane*THF (1.0 M in THF, 8.0 mL, 8.0 mmol) was added dropwise. The resulting solution was heated to reflux overnight, additional borane*THF (8 mL, 8.0 mmol) was added and the mixture was heated to reflux overnight. Additional borane*THF (18 mL, 18.0 mmol) was added and the mixture was stirred at reflux overnight, then at room temperature for 7 days. The reaction was cooled to 0° C., quenched with water, acidified with aqueous hydrochloric acid (6 N), and heated to reflux for 2 h. The resulting mixture was extracted with dichloromethane (4 times). The aqueous layer was basified with aqueous sodium hydroxide (1 N) and extracted with dichloromethane (5 times). The organic extracts of the basic aqueous layer were combined, washed sequentially with saturated aqueous sodium bicarbonate (twice) and saturated brine, dried over magnesium sulfate, filtered, and concentrated under reduced pressure to give the title compound 1-31 as a dense brown syrup (0.30 g).

Example 8

Preparation of benzyl{(5S)-5-[(tert-butoxycarbonyl)amino]-6-hydroxyhexyl}carbamate (1-34)

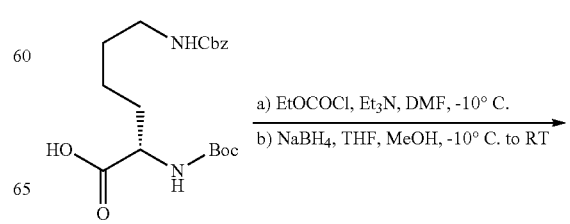

-continued

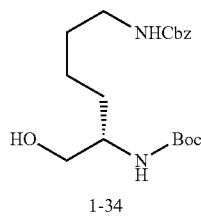

1-34

To a solution of Boc-Lys(Z)—OH (3.00 g, 7.89 mmol) and triethylamine (1.2 mL, 8.7 mmol) in N,N-dimethylformamide (10 mL) at −10° C. under a dry nitrogen atmosphere, ethyl chloroformate (0.83 mL, 8.7 mmol) was added dropwise. The reaction was stirred for 30 minutes and filtered, rinsing with tetrahydrofuran (3 times 2 mL). The filtrate was cooled to 0° C. under a dry nitrogen atmosphere, and sodium borohydride (895 mg, 23.7 mmol) was added. To this mixture, methanol (100 mL) was added dropwise. The reaction was allowed to warm to room temperature, stirred for 1 hour, carefully acidified with aqueous hydrochloric acid (2 N), and concentrated under reduced pressure. The residue was partitioned between water and ethyl acetate and the aqueous layer was extracted with ethyl acetate (twice). The combined organic layers were washed successively with aqueous hydrochloric acid (1 N), water, saturated aqueous sodium bicarbonate, and brine (twice), dried over magnesium sulfate, filtered, and concentrated under reduced pressure to give the title product 1-34 as a colorless oil (2.58 g).

Alternately, N-methylmorpholine could be used in place of triethylamine. This variation of the procedure in this example was used to prepare: tert-butyl[(2S)-1-hydroxyhexan-2-yl]carbamate (2-2) from N-tert-butoxycarbonylnorleucine (Boc-Nle-OH); and tert-butyl[(2R)-1-hydroxyhexan-2-yl]carbamate (2-59) from Boc-D-Nle-OH.

Example 9

Preparation of tert-butyl[(2S)-1-{[bis(2-thienylmethyl)carbamoyl]oxy}hexan-2-yl]carbamate (2-3)

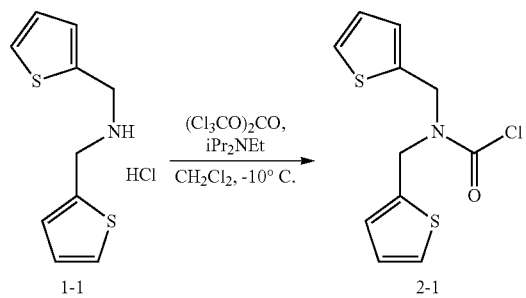

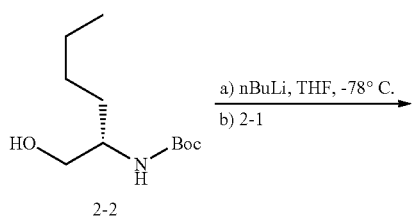

-continued

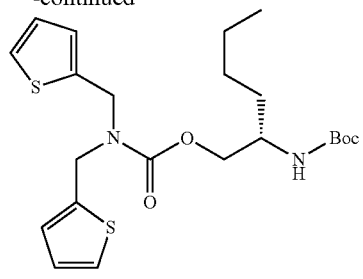

2-3

I. Bis(2-thiophenylmethyl)carbamic chloride (2-1)

To a stirred solution of triphosgene (381 mg, 1.28 mmol) and N,N-diisopropylethylamine (0.60 mL, 3.5 mmol) in dichloromethane (15 mL) at −10° C. under nitrogen, a solution of 1-1 (757 mg, 3.08 mmol) and N,N-diisopropylethylamine (0.60 mL, 3.5 mmol) in dichloromethane (5 mL) was added dropwise. The reaction was allowed to warm to room temperature and stirred for 24 hours. Additional triphosgene (162 mg, 0.54 mmol) was added and the mixture was stirred for 1 hour. The reaction mixture was diluted with ethyl acetate:hexanes (1:1), washed sequentially with water, aqueous hydrochloric acid (1N), saturated aqueous sodium bicarbonate, and saturated brine. The organic layer was dried over magnesium sulfate, filtered, and concentrated under reduced pressure to give the title compound 2-1 as an amber oil (934 mg). This material was used without purification.

This procedure was also used to prepare: methyl(2-thienylmethyl)carbamic chloride (2-33) from 2-32; and {2-[bis(2-thienylmethyl)sulfamoyl]ethyl}butylcarbamic chloride (7-5) from 7-4. Alternately, tetrahydrofuran could be used as solvent. This variation was used to prepare: bis(4-methoxybenzyl)carbamic chloride (2-65) from 1-6; dibenzylcarbamic chloride (2-71) from dibenzylamine; bis(4-methylbenzyl)carbamic chloride (2-75) from 1-43; bis(4-chlorobenzyl)carbamic chloride (2-79) from 1-44; (4-bromobenzyl)(2-thienylmethyl)carbamic chloride (2-83) from 1-46; phenyl(2-thienylmethyl)carbamic chloride (2-88) from 1-30; bis(3-thienylmethyl)carbamic chloride (2-92) from 1-47; butyl(2-thienylmethyl)carbamic chloride (2-96) from 1-9; (2-methoxyethyl)(2-thienylmethyl)carbamic chloride (2-101) from 1-12; bis(cyclopropylmethyl)carbamic chloride (2-109) from 1-48; and diisobutylcarbamic chloride (2-113) from diisobutylamine.

Alternately, a primary amine could be used in place of the secondary amine hydrochloride, giving an isocyanate instead of a carbamic chloride. This variation was used to prepare 2-thienylmethylisocyanate (3-157) from 2-thiophenylmethylamine.

II. tert-Butyl[(2S)-1-{[bis(2-thienylmethyl)carbamoyl]oxy}hexan-2-yl]carbamate (2-3)

To a stirred solution of 2-2 (0.66 g, 3.0 mmol) in tetrahydrofuran (15 mL) at −78° C. under a dry nitrogen atmosphere, n-butyl lithium (1.6 M in hexanes, 2.2 mL, 3.4 mmol) was added dropwise. After 10 minutes, a solution of 2-1 in tetrahydrofuran (1 mL) was added dropwise. The reaction was allowed to warm to room temperature slowly and stirred for 2 days. The reaction was diluted with saturated aqueous sodium bicarbonate and extracted with ethyl acetate (three times). The organic layers were combined and washed with saturated brine. The organic layer was dried over magnesium sulfate, filtered, and concentrated under reduced pressure. The crude product was purified by chromatography on silica gel, eluting with hexanes:ethyl acetate (9:1 to 1:1) to give the title compound as a yellow solid (0.37 g).

This procedure was also used to prepare the following compounds: tert-butyl(2-{[bis(2-thienylmethyl)carbamoyl]oxy}ethyl)carbamate (2-15) from tert-buty 2-hydroxyethylcarbamate and 2-1; and (2S)-2-[(tert-butoxycarbonyl)amino]hexyl methyl(2-thienylmethyl)carbamate (2-34) from 2-2 and 2-33.

Alternately, potassium bis(trimethylsilyl)amide (0.5M in toluene) could be used in place of butyllithium. This variation was used to prepare: benzyl{(5S)-6-{[bis(2-thienylmethyl)carbamoyl]oxy}-5-[(tert-butoxycarbonyl)amino]hexyl}carbamate (2-56) from 1-34 and 2-1; and tert-butyl [(2R)-1-{[bis(2-thienylmethyl)carbamoyl]oxy}hexan-2-yl]carbamate (2-60) from 2-59 and 2-1. This variation was also performed using lithium bis(trimethylsilyl)amide (1.0 M in tetrahydrofuran) as base to prepare: benzyl{(5S)-6-{[bis(4-methoxybenzyl)carbamoyl]oxy}-5-[(tert-butoxycarbonyl)amino]hexyl}carbamate (2-66) from 1-34 and 2-65; tert-butyl[(2S)-1-{[bis(4-methoxybenzyl)carbamoyl]oxy}hexan-2-yl]carbamate (2-67) from 2-2 and 2-65; (2S)-2-[(tert-butoxycarbonyl)amino]hexyl dibenzylcarbamate (2-72) from 2-2 and 2-71; tert-butyl[(2S)-1-{[bis(4-methylbenzyl)carbamoyl]oxy}hexan-2-yl]carbamate (2-76) from 2-2 and 2-75; tert-butyl[(2S)-1-{[bis(4-chlorobenzyl)carbamoyl]oxy}hexan-2-yl]carbamate (2-80) from 2-2 and 2-79; (2S)-2-[(tert-butoxycarbonyl)amino]hexyl(4-bromobenzyl)(2-thienylmethyl)carbamate (2-84) from 2-2 and 2-83; (2S)-2-[(tert-butoxycarbonyl)amino]hexyl phenyl(2-thienylmethyl)carbamate (2-89) from 2-2 and 2-88; tert-butyl[(2S)-1-{[bis(3-thienylmethyl)carbamoyl]oxy}) hexan-2-yl]carbamate (2-93) from 2-2 and 2-92; benzyl [(5S)-5-[(tert-butoxycarbonyl)amino]-6-{[butyl(2-thienylmethyl)carbamoyl]oxy}hexyl]carbamate (2-97) from 1-34 and 2-96; (2S)-2-[(tert-butoxycarbonyl)amino]hexyl butyl(2-thienylmethyl)carbamate (2-98) from 2-2 and 2-96; benzyl[(5S)-5-[(tert-butoxycarbonyl)amino]-6-{[(2-methoxyethyl)(2-thienylmethyl)carbamoyl]oxy}hexyl]carbamate (2-102) from 1-34 and 2-101; (2S)-2-[(tert-butoxycarbonyl)amino]hexyl(2-methoxyethyl)(2-thienylmethyl)carbamate (2-103) from 2-2 and 2-101; and tert-butyl[(2S)-1-{[bis(cyclopropylmethyl)carbamoyl]oxy}hexan-2-yl]carbamate (2-110) from 2-2 and 2-109; and (2S)-2-[(tert-butoxycarbonyl)amino]hexyl diisobutylcarbamate (2-114) from 2-2 and 2-113.

Example 10

Preparation of methyl(6S,10S)-10-(1,3-benzodioxol-5-yl)-6-butyl-3,8-dioxo-1-(2-thienyl)-2-(2-thienylmethyl)-4-oxa-2,7,9-triazadodecan-12-oate (2-5)

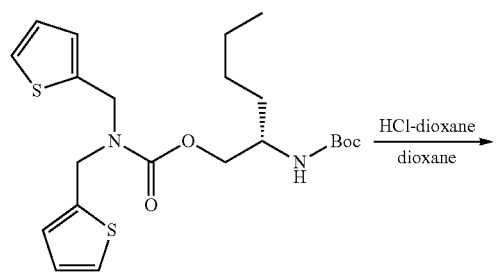

2-3

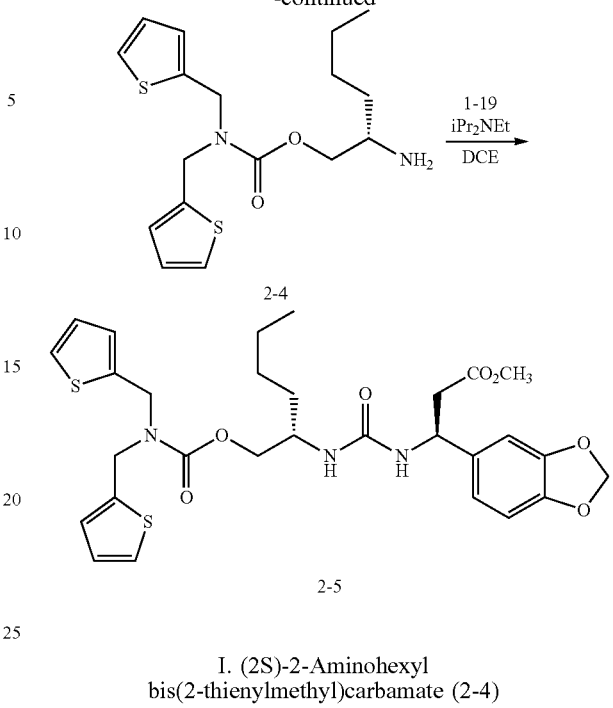

2-4

2-5

I. (2S)-2-Aminohexyl bis(2-thienylmethyl)carbamate (2-4)

To a solution of 2-3 (0.49 g, 1.0 mmol) in 1,4-dioxane (3 mL), hydrogen chloride (4 M in dioxane, 2.7 mL, 11 mmol) was added. The reaction was sealed with a rubber septum and stirred overnight. The mixture was then cooled to 0° C. and basified with saturated aqueous sodium bicarbonate and extracted with ethyl acetate. The organic layer was washed with saturated aqueous sodium bicarbonate and saturated brine, dried over magnesium sulfate, filtered, and concentrated under reduced pressure to give the title compound 2-4 as a dark brown oil (0.40 g). This material was used without further purification.

The following compounds were prepared according to this procedure: (S)-2-(methylamino)hexyl bis(2-thienylmethyl)carbamate (2-7) from 2-6; 2-aminoethyl bis(2-thienylmethyl)carbamate (2-16) from 2-15; (2S)-2-aminohexyl methyl(2-thienylmethyl)carbamate (2-35) from 2-34; (2S)-2-amino-N,N-bis(2-thienylmethyl)hexanamide (3-13) from 3-12; (2R)-2-amino-N,N-bis(2-thienylmethyl)hexanamide (3-57) from 3-10; and benzyl{(5S)-5-amino-6-[bis(2-thienylmethyl)amino]-6-oxohexyl}carbamate (3-66) from 3-65.

In another variation, trifluoroacetic acid could be used in place of hydrogen chloride. The following compounds were prepared according to this variation of the procedure: 2-amino-N,N-bis(thiophen-2-ylmethyl)acetamide (3-2) from 3-1; and 3-amino-N,N-bis(thiophen-2-ylmethyl)propanamide (3-5) from 3-4. This variation was also further modified by using dichloromethane as solvent to prepare: 6-amino-N,N-bis(2-thienylmethyl)hexanamide (3-103) from 3-102; 6-amino-N,N-bis(4-methoxybenzyl)hexanamide (3-135) from 3-134; 4-amino-N,N-bis(2-thienylmethyl)butanamide (3-146) from 3-145; and 3-(butylamino)-N,N-bis(2-thienylmethyl)propanamide (3-155) from 3-154; and 3-(methylamino)-N,N-bis(2-thienylmethyl)propanamide (7-33) from 7-32.

II. Methyl(6S,10S)-10-(1,3-benzodioxol-5-yl)-6-butyl-3,8-dioxo-1-(2-thienyl)-2-(2-thienylmethyl)-4-oxa-2,7,9-triazadodecan-12-oate (2-5)

To a solution of 1-19 (86 mg, 0.22 mmol) in 1,2-dichloroethane (1.5 mL), a solution of 2-4 (87 mg, 0.25 mmol) and N,N-diisopropylethylamine (0.080 mL, 0.46 mmol) in 1,2-dichloroethane (0.5 mL) was added. The resulting bright yellow reaction mixture was sealed and stirred for 2 days, diluted with ethyl acetate/hexanes (1:1), washed with saturated aqueous sodium bicarbonate (8-9 times) and saturated brine. The organic layer was dried over magnesium sulfate, filtered, and concentrated under reduced pressure. The residue was purified by column on silica gel chromatography, eluting with hexanes:ethyl acetate (13:7 to 11:9) to give the title compound 2-5 as a pale yellow to tan syrup (107 mg).

This procedure was also used to prepare: methyl(6S,10S)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate (2-8) from 2-7 and 1-19; ethyl(6S,10R)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate (2-9) from 2-7 and 1-21; (2S)-2-{[(1,3-benzodioxol-5-ylmethyl)carbamoyl]amino}hexyl bis(2-thienylmethyl)carbamate (2-11) from piperonylamine and 2-10; methyl(6S,10S)-10-(1,3-benzodioxol-5-yl)-6-butyl-9-methyl-3,8-dioxo-1-(2-thienyl)-2-(2-thienylmethyl)-4-oxa-2,7,9-triazadodecan-12-oate (2-38) from 2-10 and 2-37; (2S)-2-{[(1,3-benzodioxol-5-ylmethyl)carbamoyl]amino}-N,N-bis(2-thienylmethyl)hexanamide (3-46) from 3-44 and piperonylamine; (2S)-2-{[(4-hydroxybenzyl)carbamoyl]amino}-N,N-bis(2-thienylmethyl)hexanamide (3-47) from 3-44 and 4-hydroxybenzylamine; (2S)-2-({[3-(morpholin-4-yl)benzyl]carbamoyl}amino)-N,N-bis(2-thienylmethyl)hexanamide (3-50) from 3-44 and (3-morpholinophenyl)methylamine; (2S)-2-{[(pyridin-3-ylmethyl)carbamoyl]amino}-N,N-bis(2-thienylmethyl)hexanamide (3-51) from 3-44 and 3-(aminomethyl)pyridine; (2S)-2-({[(6-methoxypyridin-3-yl)methyl]carbamoyl}amino)-N,N-bis(2-thienylmethyl)hexanamide (3-52) from 3-44 and 1-31; methyl(3S)-3-(1,3-benzodioxol-5-yl)-3-[({(2R)-1-[bis(thiophen-2-ylmethyl)amino]-1-oxohexan-2-yl}carbamoyl)amino]propanoate (3-58) from 3-57 and 1-19; benzyl[(5S)-6-[bis(2-thienylmethyl)amino]-6-oxo-5-{[(pyridin-3-ylmethyl)carbamoyl]amino}hexyl]carbamate (3-79) from 3-(aminomethyl)pyridine and 3-67; benzyl[(5S)-6-[bis(2-thienylmethyl)amino]-5-({[3-(morpholin-4-yl)benzyl]carbamoyl}amino)-6-oxohexyl]carbamate (3-80) from (3-morpholinophenyl)methylamine and 3-67; ethyl(3R)-3-(1,3-benzodioxol-5-yl)-3-[({(2S)-1-[bis(2-thienylmethyl)amino]-1-oxohexan-2-yl}carbamoyl)amino]propanoate (3-120) from 3-13 and 1-21; and ethyl(3R)-3-(1,3-benzodioxol-5-yl)-3-[({(2R)-1-[bis(2-thienylmethyl)amino]-1-oxohexan-2-yl}carbamoyl)amino]propanoate (3-126) from 3-57 and 1-21.

Alternately, the hydrochloride salt of the amine may be used by increasing the amount of base. This variation was used to prepare: methyl(6S)-6-butyl-3,8-dioxo-1-(2-thienyl)-2-(2-thienylmethyl)-4-oxa-2,7,9-triazadodecan-12-oate (2-14) from -alanine methyl ester hydrochloride and 2-10; methyl(9S,13S)-13-(1,3-benzodioxol-5-yl)-9-({[bis(2-thienylmethyl)carbamoyl]oxy}methyl)-3,11-dioxo-1-phenyl-2-oxa-4,10,12-triazapentadecan-15-oate (2-58) from 2-57 and 1-19; methyl(6R,10S)-10-(1,3-benzodioxol-5-yl)-6-butyl-3,8-dioxo-1-(2-thienyl)-2-(2-thienyl)-2-(2-thienylmethyl)-4-oxa-2,7,9-triazadodecan-12-oate (2-62) from 2-61 and 1-19; methyl(6R,10R)-10-(1,3-benzodioxol-5-yl)-6-butyl-3,8-dioxo-1-(2-thienyl)-2-(2-thienylmethyl)-4-oxa-2,7,9-triazadodecan-12-oate (2-63) from 2-61 and 1-32; (2S)-2-({[4-(dimethylamino)benzyl]carbamoyl}amino)-N,N-bis(2-thienylmethyl)hexanamide (3-48) from 3-44 and 4-dimethylaminobenzylamine dihydrochloride; methyl 3-[({(2S)-1-[bis(2-thienylmethyl)amino]-1-oxohexan-2-yl}carbamoyl)amino]propanoate (3-49) from 3-44 and beta-alanine methyl ester hydrochloride; methyl(3S)-3-(1,3-benzodioxol-5-yl)-3-[({(2R)-6-{[(benzyloxy)carbonyl]amino}-1-[bis(thiophen-2-ylmethyl)amino]-1-oxohexan-2-yl}carbamoyl)amino]propanoate (3-64) from 3-63 and 1-19; benzyl{(5S)-6-[bis(2-thienylmethyl)amino]-5-[({3-[(methylsulfonyl)amino]benzyl}carbamoyl)amino]-6-oxohexyl}carbamate (3-68) from 3-67 and 1-25; methyl(6S,10S)-10-(1,3-benzodioxol-5-yl)-6-butyl-2-(4-methoxybenzyl)-1-(4-methoxyphenyl)-3,8-dioxo-4-oxa-2,7,9-triazadodecan-12-oate (2-69) from 2-68 and 1-19; methyl(6S,10S)-10-(1,3-benzodioxol-5-yl)-2-benzyl-6-butyl-3,8-dioxo-1-phenyl-4-oxa-2,7,9-triazadodecan-12-oate (2-74) from 2-73 and 1-19; methyl(6S,10S)-10-(1,3-benzodioxol-5-yl)-6-butyl-2-(4-methylbenzyl)-1-(4-methylphenyl)-3,8-dioxo-4-oxa-2,7,9-triazadodecan-12-oate (2-78) from 2-77 and 1-19; methyl(6S,10S)-10-(1,3-benzodioxol-5-yl)-6-butyl-2-(4-chlorobenzyl)-1-(4-chlorophenyl)-3,8-dioxo-4-oxa-2,7,9-triazadodecan-12-oate (2-82) from 2-81 and 1-19; methyl(6S,10S)-10-(1,3-benzodioxol-5-yl)-2-(4-bromobenzyl)-6-butyl-3,8-dioxo-1-(2-thienyl)-4-oxa-2,7,9-triazadodecan-12-oate (2-86) from 2-85 and 1-19; methyl (6S,10S)-10-(1,3-benzodioxol-5-yl)-6-butyl-3,8-dioxo-2-phenyl-1-(2-thienyl)-4-oxa-2,7,9-triazadodecan-12-oate (2-91) from 2-90 and 1-19; methyl(3S,7S)-3-(1,3-benzodioxol-5-yl)-7-butyl-5,10-dioxo-11-(2-thienylmethyl)-9-oxa-4,6,11-triazapentadecan-1-oate (2-100) from 2-99 and 1-19; methyl(9S,13S)-13-(1,3-benzodioxol-5-yl)-9-butyl-6,11-dioxo-5-(2-thienylmethyl)-2,7-dioxa-5,10,12-triazapentadecan-15-oate (2-105) from 2-104 and 1-19; (2S)-2-[({3-[(methylsulfonyl)amino]benzyl}carbamoyl)amino]hexyl(2-methoxyethyl)(2-thienylmethyl)carbamate (2-107) from 1-25 and 2-106; (2S)-2-{[(4-bromobenzyl)carbamoyl]amino}hexyl bis(2-thienylmethyl)carbamate (2-111) from 4-bromobenzylamine and 2-10; methyl(8S,12S)-12-(1,3-benzodioxol-5-yl)-8-butyl-4-isobutyl-2-methyl-5,10-dioxo-6-oxa-4,9,11-triazatetradecan-14-oate (2-116) from 2-115 and 1-19; and methyl(6S,10S)-10-(1,3-benzodioxol-5-yl)-6-butyl-3,8-dioxo-1-(2-thienyl)-2-(2-thienylmethyl)-4-thia-2,7,9-triazadodecan-12-oate (2-120) from 2-119 and 1-19.

In another variation, tetrahydrofuran could be used in place of dichloroethane. This procedure was used to prepare: ethyl(6S,10R)-10-(1,3-benzodioxol-5-yl)-6-butyl-3,8-dioxo-1-(2-thienyl)-2-(2-thienylmethyl)-4-oxa-2,7,9-triazadodecan-12-oate (2-28) from 2-4 and 1-21; methyl(6S,10S)-10-(1,3-benzodioxol-5-yl)S,1-benzodioxol-5-yl)-6-butyl-2-methyl-3,8-dioxo-1-(2-thienyl)-4-oxa-2,7,9-triazadodecan-12-oate (2-36) from 1-19 and 2-35; methyl(3S)-3-(1,3-benzodioxol-5-yl)-3-[({2-[bis(2-thienylmethyl)amino]-2-oxoethyl}carbamoyl)amino]propanoate (3-3) from 3-2 and 1-19; and methyl(3S)-3-(1,3-benzodioxol-5-yl)-3-[({3-[bis(2-thienylmethyl)amino]-3-oxopropyl}carbamoyl)amino]propanoate (3-6) from 3-5 and 1-19.

Dichloromethane was used as solvent to prepare: methyl (6S,10S)-6-butyl-3,8-dioxo-10-phenyl-1-(2-thienyl)-2-(2-thienylmethyl)-4-oxa-2,7,9-triazadodecan-12-oate (2-13) from 2-10 and 2-12; methyl{[bis(2-thienylmethyl)carbamoyl](methyl)amino}acetate (2-50) from sarcosine methyl ester hydrochloride and 1-33; and methyl(2R)-[({(2S)-1-[bis(thiophen-2-ylmethyl)amino]-1-oxohexan-2-yl}carbamoyl)

amino](phenyl)ethanoate (3-45) from 3-44 and (R)-(−)-2-phenylglycine methyl ester hydrochloride.

Example 11

Preparation of tert-butyl[(2S)-1-{[bis(2-thienylmethyl)carbamoyl]oxy}hexan-2-yl]methylcarbamate (2-6)

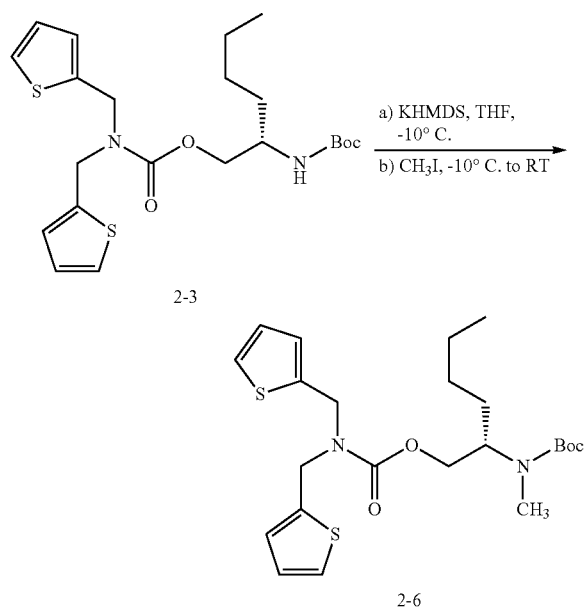

To a stirred solution of 2-3 (153 mg, 0.34 mmol) in tetrahydrofuran (1.3 mL) at −10° C. under a dry nitrogen atmosphere, potassium bis(trimethylsilyl)amide (KHMDS, 0.5 M in toluene, 0.7 mL, 0.35 mmol) was added dropwise. After 15 minutes, iodomethane (0.028 mL, 0.45 mmol) was added. The reaction was allowed to warm to room temperature and stirred for 2 days. Additional KHMDS (0.2 mL, 0.10 mmol) and iodomethane (0.02 mL, 0.32 mmol) were added sequentially and the mixture was stirred 2 days. More KHMDS (0.4 mL, 0.20 mmol) and iodomethane (0.02 mL, 0.32 mmol) were added sequentially and the mixture was stirred overnight. The reaction was diluted with saturated aqueous sodium bicarbonate and extracted with ethyl acetate. The organic layer was washed sequentially with saturated aqueous sodium bicarbonate and saturated brine, dried over magnesium sulfate, filtered, and concentrated under reduced pressure. The residue was purified by column on silica gel chromatography, eluting with hexanes:ethyl acetate (23:2 to 17:3) to give the title compound 2-6 as a colorless syrup (80 mg).

This procedure was also used to prepare tert-butyl methyl (2-thienylmethyl)carbamate (2-31) from 2-30.

Alternately, dioxane could be used in place of tetrahydrofuran. This variation was used to prepare (2S)-2-[acetyl(methyl)amino]-N,N-bis(2-thienylmethyl)hexanamide (3-55) from 3-37.

In another variation, sodium hydride (60% dispersion in mineral oil) and N,N-dimethylformamide at room temperature could be used in place of KHMDS and tetrahydrofuran. In some cases, the reaction was heated after mixing all reagents. This variation was used to prepare: tert-butyl{[bis(2-thienylmethyl)carbamoyl](butyl)amino}acetate (2-52) from 2-51 and n-butyliodide; methyl{[bis(2-thienylmethyl)carbamoyl](butyl)amino}acetate (2-54) from 2-53 and n-butyliodide; N-{6-[bis(2-thienylmethyl)amino]-6-oxohexyl}-N-(3-methoxybenzyl)thiophene-2-carboxamide (3-115) from 3-107 and 3-methoxybenzyl bromide; tert-butyl{(2S)-6-[benzyl(trifluoroacetyl)amino]-1-[bis(2-thienylmethyl)amino]-1-oxohexan-2-yl}carbamate (3-123) from 3-90 and benzyl chloride; N-{6-[bis(2-thienylmethyl)amino]-6-oxohexyl}-N-methylthiophene-2-carboxamide (3-139) from 3-107 and iodomethane at 50° C.; 6-[(3-methoxybenzyl)(2-thienylacetyl)amino]-N,N-bis(2-thienylmethyl)hexanamide (3-140) from 3-112 and 3-methoxybenzyl bromide; tert-butyl{3-[bis(2-thienylmethyl)amino]-3-oxopropyl}butylcarbamate (3-154) from 3-4 and butyl iodide at 50° C.; and tert-butyl{3-[bis(2-thienylmethyl)amino]-3-oxopropyl}methylcarbamate (7-32) from 3-4 and iodomethane at 50° C. This variation was also used to alkylate sulfonamide 7-8 with alkyl chloride 7-9 at 50° C. to give N-{3-[bis(2-thienylmethyl)sulfamoyl]propyl}-N-(2-thienylmethyl)thiophene-2-sulfonamide (7-10).

In yet another variation disulfonamide 5-32 was treated with 0.5 equivalents sodium hydride in tetrahydrofuran followed by 0.75 equivalents 3-methoxybenzyl bromide to give N-(3-methoxybenzyl)-N-{5-[(2-thienylsulfonyl)amino]pentyl}thiophene-2-sulfonamide (5-33).

In another variation, symmetrical diamide, 5-36, was treated 1.1 equivalents lithium bis(trimethylsilyl)amide in tetrahydrofuran followed by 1.1 equivalents of 3-methoxybenzylbromide to give predominantly N-(3-methoxybenzyl)-N-{5-[(2-thienylcarbonyl)amino]pentyl}thiophene-2-carboxamide (5-37). N,N'-Pentane-1,5-diylbis[N-(3-methoxybenzyl)thiophene-2-carboxamide](5-38) was prepared by this variation by increasing to 2.2 equivalents each of lithium bis(trimethylsilyl)amide and 3-methoxybenzylbromide.

Example 12

Preparation of methyl(3S)-3-amino-3-phenylpropanoate (2-12)

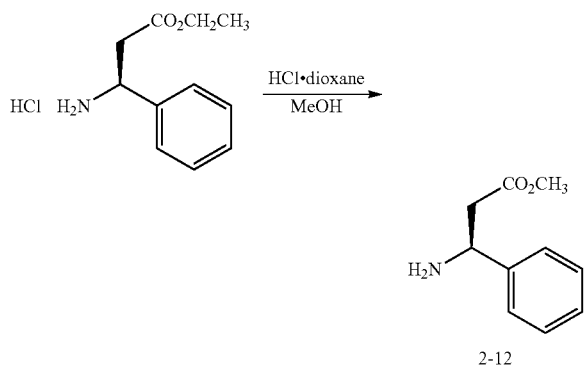

To a stirred solution of ethyl(S)-3-amino-3-phenylpropanoate (102 mg, 0.44 mmol) in methanol (10 mL), hydrogen chloride (4 M in anhydrous 1,4-dioxane, 0.2 mL, 0.8 mmol) was added. The reaction was heated to reflux overnight, cooled to room temperature, poured into saturated aqueous sodium bicarbonate, and extracted twice with ethyl acetate. The combined organic layers were washed twice with saturated brine, dried over magnesium sulfate, filtered, and concentrated under reduced pressure to give the title compound 2-12 as a yellow oil (36 mg). This material was used without further purification.

Example 13

Preparation of methyl(10S)-10-(1,3-benzodioxol-5-yl)-3,8-dioxo-1-(2-thienyl)-2-(2-thienylmethyl)-4-oxa-2,7,9-triazadodecan-12-oate (2-18)

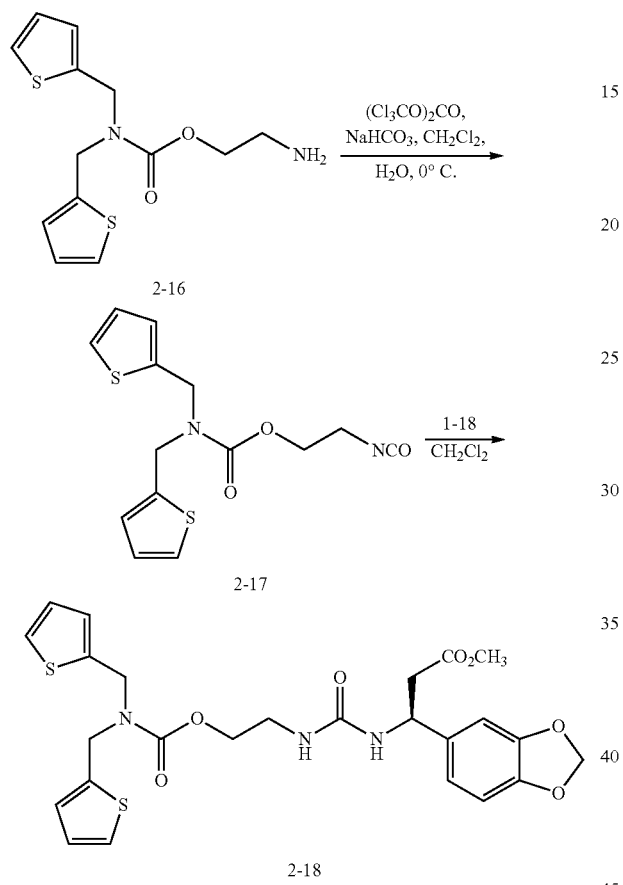

I. 2-Isocyanatoethyl bis(2-thienylmethyl)carbamate (2-17)

To a stirred mixture of 2-16 (90 mg, 0.30 mmol) in dichloromethane (1 mL) and saturated aqueous sodium bicarbonate (1 mL) at 0° C., a solution of triphosgene (38 mg, 0.13 mmol) in dichloromethane (0.2 mL) was added. After 2.5 h, the reaction was diluted with dichloromethane and aqueous saturated sodium bicarbonate and the aqueous phase was washed with dichloromethane. The combined organic phases were washed with saturated brine, dried over magnesium sulfate, filtered, and concentrated under reduced pressure to give the title compound 2-17 as a yellow-brown oil (75 mg). This material was used without purification.

II. Methyl(10S)-10-(1,3-benzodioxol-5-yl)-3,8-dioxo-1-(2-thienyl)-2-(2-thienylmethyl)-4-oxa-2,7,9-triazadodecan-12-oate (2-18)

To a solution of 2-17 (75 mg, 0.23 mmol) in dichloromethane (0.50 mL), a solution of 1-18 (66 mg, 0.30 mmol) in dichloromethane (0.25 mL) was added followed by two dichloromethane (0.25 mL) rinses. After 2 days, the reaction was directly purified by column chromatography on silica gel, eluting with hexanes:ethyl acetate/hexanes (2:3 to 1:4) to give the title compound 2-18 as a colorless solid (72 mg).

This procedure was also used to prepare: (2S)-2-[(benzylcarbamoyl)amino]hexyl bis(2-thienylmethyl)carbamate (2-20) from 2-4 and benzyl isocyanate; (2S)-2-[(tert-butylcarbamoyl)amino]hexyl bis(2-thienylmethyl)carbamate (2-21) from 2-4 and tert-butyl isocyanate; (2S)-2-[(isopropylcarbamoyl)amino]hexyl bis(2-thienylmethyl)carbamate (2-22) from 2-4 and isopropyl isocyanate; (2S)-2-[(tert-butylcarbamoyl)amino]-N,N-bis(2-thienylmethyl)hexanamide (3-38) from 3-13 and tert-butylisocyanate; (2S)-2-[(isopropylcarbamoyl)amino]-N,N-bis(2-thienylmethyl) hexanamide (3-39) from 3-13 and isopropylisocyanate in dichloroethane; (2S)-2-[(benzylcarbamoyl)amino]-N,N-bis(2-thienylmethyl)hexanamide (3-53) from 3-13 and benzyl isocyanate; and (2R)-2-[(benzylcarbamoyl)amino]-N,N-bis(2-thienylmethyl)hexanamide (3-61) from 3-57 and benzyl isocyanate.

Alternately, the isocyanate could be reacted with an amine or amine hydrochloride in the presence of a tertiary amine base, such as N,N-diisopropylethylamine or pyridine, and the crude reaction mixture was subjected to a standard aqueous workup. This variation was used to prepare: methyl 3,8-dioxo-1-(2-thienyl)-2-(2-thienylmethyl)-4-oxa-2,7,9-triazadodecan-12-oate (2-19) from 2-17 and beta-alanine methyl ester hydrochloride with N,N-diisopropylethylamine; benzyl{(5S)-5-[(benzylcarbamoyl)amino]-6-[bis(2-thienylmethyl)amino]-6-oxohexyl}carbamate (3-78) from benzyl isocyanate and 3-66.HCl with pyridine; and 3-{butyl [(2-thienylmethyl)carbamoyl]amino}-N,N-bis(2-thienylmethyl)propanamide (3-158) from 3-157 and 3-155 with N,N-diisopropylethylamine.

Example 14

Preparation of (2S)-2-[(methylcarbamoyl)amino] hexyl bis(2-thienylmethyl)carbamate (2-23)

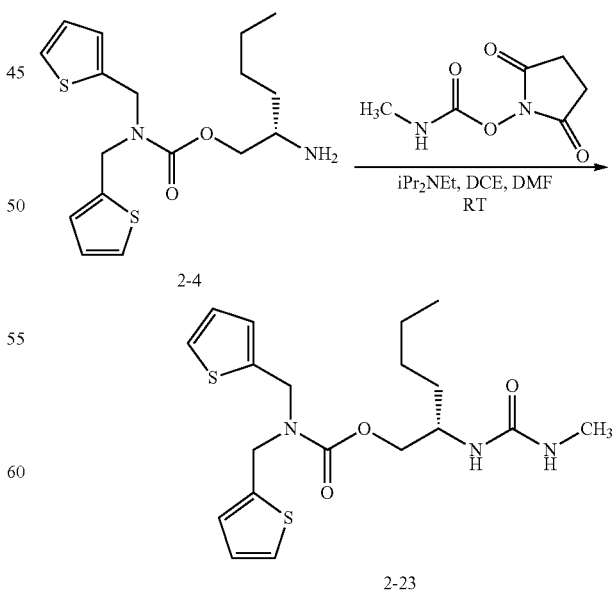

To a suspension of 2-4 (39 mg, 0.11 mol) in 1,2-dichloroethane (0.25 mL), a solution of N-succinimidyl-N-methylcarbamate (NSMC, 29 mg, 0.17 mmol) in 1,2-dichloroethane (0.5 mL) was added. The reaction was stirred at room temperature for 1 day and N,N-dimethylformamide (0.50 mL) was added to improve the solubility. The mixture was stirred 2 days and additional NSMC (38 mg, 0.22 mmol) was added. The mixture was stirred for 2 additional days and NSMC (98 mg, 0.57 mmol) and N,N-diisopropylethylamine (0.20 mL, 1.2 mmol) were added. The reaction was stirred for 3 hours, diluted with saturated aqueous sodium bicarbonate, and extracted with ethyl acetate:hexanes (1:1). The organic layer was washed sequentially with saturated aqueous sodium bicarbonate, hydrochloric acid (0.1 N), water (3 times), and saturated brine. The organic layer was dried over magnesium sulfate, filtered, and concentrated under reduced pressure. The residue was purified by chromatography on silica gel, eluting with methanol (1 to 1.5%) in ethyl acetate:hexanes (3:2) to give the title compound 2-23 as a colorless solid (22 mg).

This procedure was also used to prepare (2S)-2-[(methylcarbamoyl)amino]-N,N-bis(2-thienylmethyl)hexanamide (3-40) from 3-13.

Example 15

Preparation of (2S)-2-({[(1S)-1-(1,3-benzodioxol-5-yl)-3-hydroxypropyl]carbamoyl}amino)hexyl bis(2-thienylmethyl)carbamate (2-24)

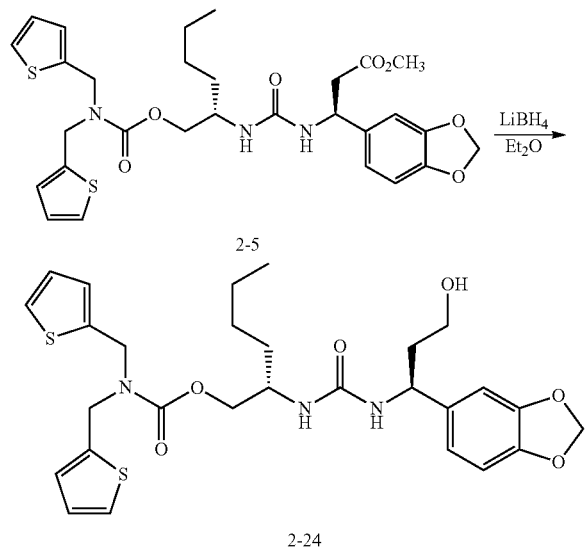

To a solution of 2-5 (90 mg, 0.15 mmol) in diethyl ether (1.5 mL), lithium borohydride (7 mg, 0.32 mmol) was added. The mixture was stirred for 90 minutes and diluted with ethyl acetate, water, and HCl (2N). The organic layer was washed with brine, dried over magnesium sulfate (anhydrous), filtered and concentrated under reduced pressure to give the title compound 2-24 as a white solid (44 mg).

This procedure was also used to prepare: 3-[(2S)-1-hydroxyhexan-2-yl]-1,1-bis(2-thienylmethyl)urea (2-45) from 2-40; and 3-[(2R)-1-hydroxyhexan-2-yl]-1,1-bis(2-thienylmethyl)urea (2-46) from 2-39.

Alternately, tetrahydrofuran could be used in place of diethyl ether. This variation was used to prepare: (2R)-2-({[(1S)-1-(1,3-benzodioxol-5-yl)-3-hydroxypropyl]carbamoyl}amino)-N,N-bis(2-thienylmethyl)hexanamide (3-59) from 3-58; 2-(hydroxymethyl)-N,N-bis(3-methoxybenzyl)thiophene-3-sulfonamide (4-40) from 4-16; and (2S)-2-({[(1S)-1-(1,3-benzodioxol-5-yl)-3-hydroxypropyl]carbamoyl}amino)hexyl bis(4-methoxybenzyl)carbamate (2-70) from 2-69.

Example 16

Preparation of (2S)-2-[(morpholin-4-ylcarbonyl)amino]hexyl bis(2-thienylmethyl)carbamate (2-25)

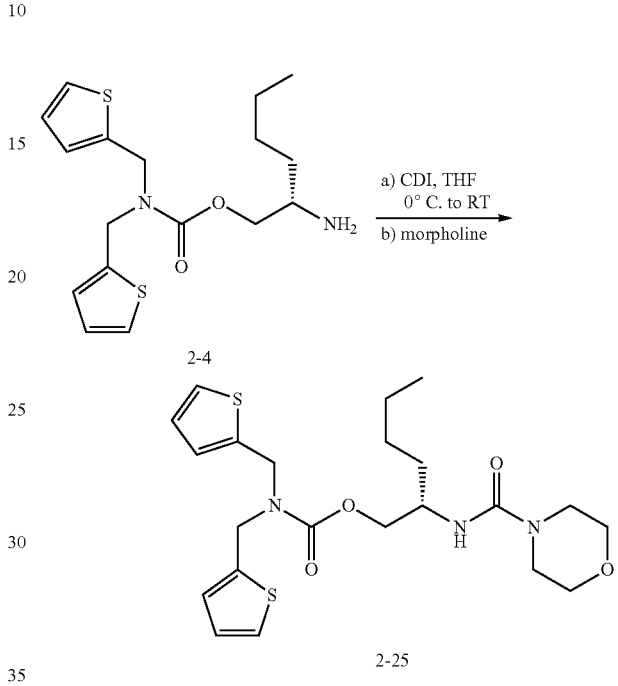

To a solution of 2-4 (39.6 mg, 0.113 mmol) in THF at 0° C., carbonyldiimidazole (24.3 mg, 0.150 mmol) was added, and the ice bath was removed to allow the solution come to room temperature. A solution of morpholine (15.5 mg, 0.180 mmol) in THF (0.5 mL) was added at room temperature by syringe. The resulting mixture was stirred for 60 hours and purified directly by chromatography on silica gel, eluting hexanes:ethyl acetate (1:1 to 1:3) to give the title compound. The reaction mixture was directly purified by chromatography on silica gel, eluting with hexanes:ethyl acetate 2-25 (50.4 mg).

This procedure was also used to prepare: (2S)-2-{[(3-methoxypropyl)carbamoyl]amino}hexyl bis(2-thienylmethyl)carbamate (2-26) from 2-4 and 3-methoxypropylamine; (2S)-2-{[(2-methoxyethyl)carbamoyl]amino}hexyl bis(2-thienylmethyl)carbamate (2-27) from 2-4 and 2-methoxyethylamine; and methyl(3R)-3-(1,3-benzodioxol-5-yl)-3-[({2-[bis(2-thienylmethyl)amino]-2-oxoethyl}carbamoyl)amino]propanoate (3-7) from 1-29 and 3-2. This procedure could also be done with N-methylmorpholine added to the reaction mixture. This modification was used to prepare: methyl(3S)-3-(1,3-benzodioxol-5-yl)-3-[({4-[bis(2-thienylmethyl)amino]-4-oxobutyl}carbamoyl)amino]propanoate (3-147) from 3-146 and 1-18 with N,N-diisopropylethylamine (1.3 equivalents); N,N-bis(2-thienylmethyl)-3-{[(2-thienylmethyl)carbamoyl]amino}propanamide (3-164) from 3-5 and 2-thiophenemethylamine with N-methylmorpholine (0.8 equivalents); and N,N-bis(2-thienylmethyl)-2-{[(2-thienylmethyl)carbamoyl]amino}ethanesulfonamide (7-18) from 7-13 and 2-thiophenemethylamine with N-methylmorpholine (0.8 equivalents).

Alternately, an amine hydrochloride may be used along with N,N-diisopropylethylamine for either or both of the reacting amines. This variation was used to prepare methyl (3R)-3-(1,3-benzodioxol-5-yl)-3-{[{2-[bis(2-thienylmethyl)amino]-2-oxoethyl}(methyl)carbamoyl]amino}propanoate (3-19) from 1-29 and 3-17. This variation was further modified by using N-methylmorpholine as base and adding N,N-dimethylformamide after combining all reactants to improve solubility. This method was used to prepare: methyl (2S)-6-{[(benzyloxy)carbonyl]amino}-2-{[bis(2-thienylmethyl)carbamoyl]amino}hexanoate (2-47) from H-Lys(Z)—OMe.HCl and 1-1; and methyl(2R)-{[bis(2-thienylmethyl)carbamoyl]amino}(phenyl)acetate (2-48) from (R)-methyl 2-amino-2-phenylacetate and 1-1.

Example 17

Preparation of methyl(6S,10R)-10-(1,3-benzodioxol-5-yl)-6-butyl-3,8-dioxo-1-(2-thienyl)-2-(2-thienylmethyl)-4-oxa-2,7,9-triazadodecan-12-oate (2-29)

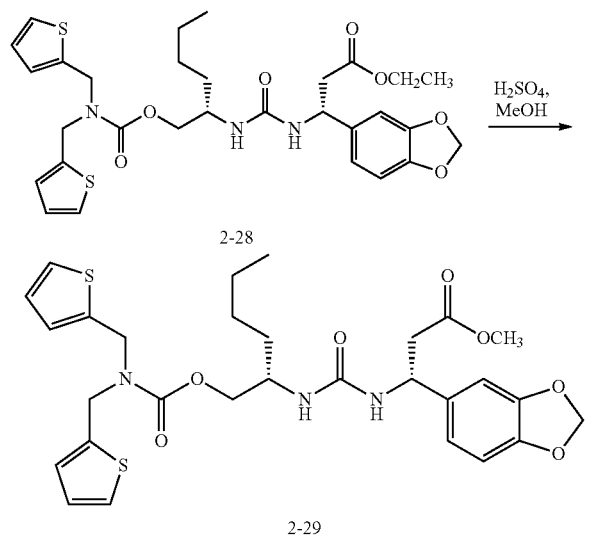

To a solution of 2-28 (0.11 g, 0.18 mmol) in methanol (1.8 mL), sulfuric acid (4 drops) was added. The solution was stirred at room temperature overnight and then briefly heated to reflux. The solution was cooled, diluted with dichloromethane and washed with saturated aqueous sodium bicarbonate. The organic layer was dried over magnesium sulfate (anhydrous), filtered, and concentrated under reduced pressure to give a pale yellow oil that solidified on standing. This material was purified by recrystallization from hexanes and ethyl acetate to give the title compound 2-29 as a white solid (40.6 mg).

Example 18

Preparation of methyl(3S)-3-(1,3-benzodioxol-5-yl)-3-(methylamino)propanoate (2-37)

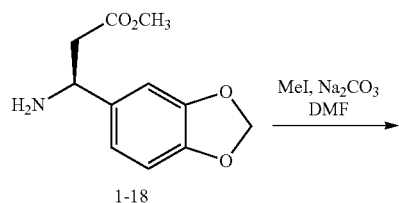

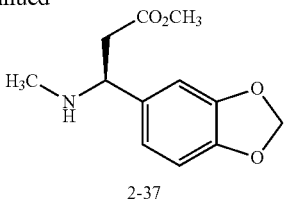

To a solution of 1-18 (275 mg, 1.23 mmol) in N,N-dimethylformamide (4.1 mL) at room temperature, iodomethane (0.084 mL, 1.36 mmol) was added. The resulting mixture was stirred at room temperature for 40 hours and then was heated to 50° C. for 2 hours. An additional portion of iodomethane (0.084 mL, 1.36 mmol) was added and the mixture was heated to 50° C. for 1 hour. The mixture was cooled to room temperature, $Na_2CO_3$ (260 mg, 2.46 mmol) was added, and the mixture was stirred for 20 hours. An additional portion of iodomethane (0.084 mL, 1.36 mmol) was added and the mixture was stirred at room temperature overnight. The mixture was diluted with ethyl acetate and washed with water (4 times) and brine. The organic layer was dried over magnesium sulfate, filtered, and concentrated under reduced pressure. The residue was filtered through a short pad of silica gel, eluting hexanes:ethyl acetate (3:2) followed by ethyl acetate:methanol (9:1). The ethyl acetate:methanol wash was concentrated under reduced pressure to give a pale yellow oil (103 mg) which contained the title compound 2-37 along with starting material and other impurities. This material was used without further purification.

Example 19

Preparation of methyl(2R)-2-{[bis(2-thienylmethyl)carbamoyl]amino}hexanoate (2-39)

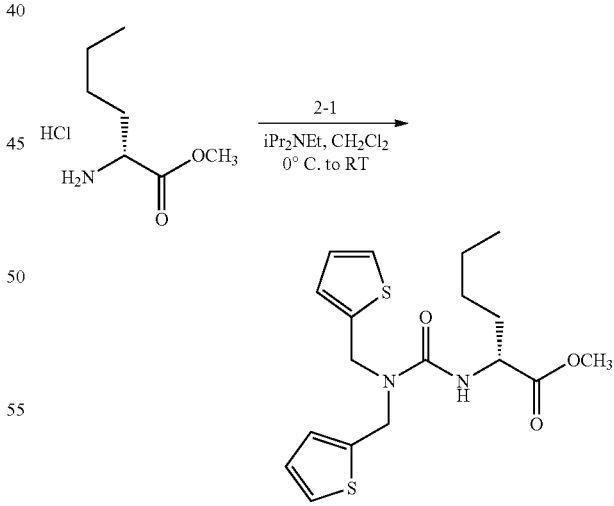

To a solution of D-norleucine methyl ester hydrochloride (134 mg, 0.74 mmol) in dichloromethane (3 mL) and N,N-diisopropylethylamine (0.30 mL, 1.6 mmols) at 0° C., 2-1 (0.07 g/mL in dichloromethane, 3.0 mL, 0.78 mmole) was added. The ice bath was removed and the mixture was stirred for 3 days, and applied directly to silica gel, eluting with hexanes:ethyl acetate (3:1) to yield the title compound 2-39 as a colorless oil (169 mg).

This procedure was also used to prepare: methyl(2S)-2-{[bis(2-thienylmethyl)-carbamoyl]amino}hexanoate (2-40) from D-norleucine methyl ester hydrochloride; tert-butyl {[bis(2-thienylmethyl)carbamoyl]amino}acetate (2-51) from tert-butyl glycine hydrochloride; methyl{[bis(2-thienylmethyl)carbamoyl]amino}acetate (2-53) from glycine methyl ester hydrochloride; 2-{butyl[(2-thienylmethyl)carbamoyl]amino}-N,N-bis(2-thienylmethyl)ethanesulfonamide (7-6) from 7-5 and 2-thiophenemethylamine; 2-{[bis(2-thienylmethyl)carbamoyl](butyl)amino}-N,N-bis(2-thienylmethyl)ethanesulfonamide (7-7) from 7-5 and 1-1; and 2-{[bis(2-thienylmethyl)carbamoyl]amino}-N,N-bis(2-thienylmethyl)ethanesulfonamide (7-14) from 7-13 and 2-1; 3-{[bis(2-thienylmethyl)carbamoyl]amino}-N,N-bis(2-thienylmethyl)propanamide (3-153) from 3-5 and 2-1; and 3-{[bis(2-thienylmethyl)carbamoyl](butyl)amino}-N,N-bis(2-thienylmethyl)propanamide (3-156) from 3-155 and 2-1; and 3-butyl-1,1-bis(2-thienylmethyl)urea (3-159) from butylamine and 2-1.

Example 20

Preparation of methyl(3R)-3-(1,3-benzodioxol-5-yl)-3-{[(2R)-2-{[bis(2-thienylmethyl)carbamoyl]amino}hexanoyl]amino}propanoate (2-41)

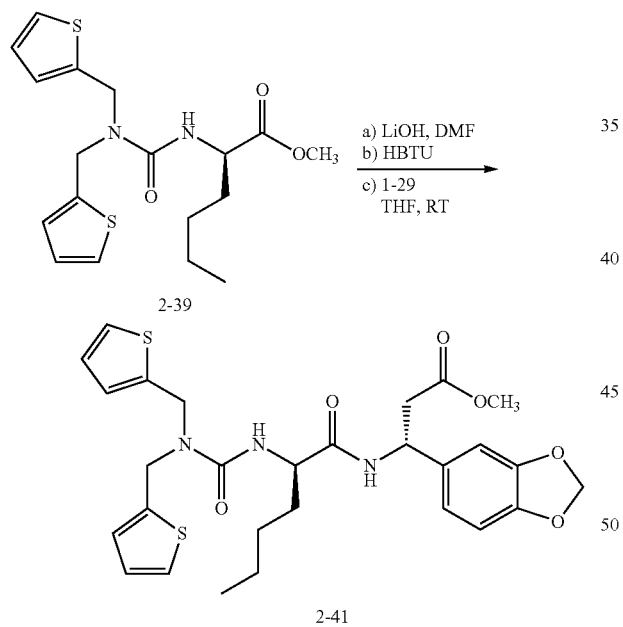

To a solution of 2-39 (103 mg, 0.272 mmol) in dimethylformamide (1.0 mL) at room temperature, powdered lithium hydroxide (9.0 mg, 0.380 mmole) was added. The solution was stirred for 1 hour, warmed to 65° C. and stirred overnight. The resulting mixture was cooled to room temperature and HBTU (103 mg, 0.22 mmol) was added to make a stock solution of the activated carboxylic acid of 2-39. To a solution of 1-29 (34 mg, 0.148 mmol) in THF (0.5 mL), the stock solution of the activated carboxylic acid (0.5 mL, 0.136 mmol) was added. The resulting mixture was stirred overnight at room temperature, diluted with hexanes:dichloromethane (2:1) and washed with aqueous HCl (2N, twice), and brine. The organic layer was dried over sodium sulfate and filtered through silica gel. The filtrate was concentrated under reduced pressure and the residue was brought up in diethyl ether and hexanes. The resulting precipitate was filtered and dried under vacuum to give the title compound 2-41 as a white solid (20.6 mg).

This procedure was also used to prepare: methyl(3S)-3-(1,3-benzodioxol-5-yl)-3-{[(2R)-2-{[bis(2-thienylmethyl)carbamoyl]amino}hexanoyl]amino}propanoate (2-42) from 2-39 and 1-18; methyl(3S)-3-(1,3-benzodioxol-5-yl)-3-{[(2S)-2-{[bis(2-thienylmethyl)carbamoyl]amino}hexanoyl]amino}propanoate (2-43) from 2-40 and 1-18, and methyl(3R)-3-(1,3-benzodioxol-5-yl)-3-{[(2S)-2-{[bis(2-thienylmethyl)carbamoyl]amino}hexanoyl]amino}propanoate (2-44) from 2-40 and 1-19.

Example 21

Preparation of 3-(3-hydroxypropyl)-1,1-bis(2-thienylmethyl)urea (2-49)

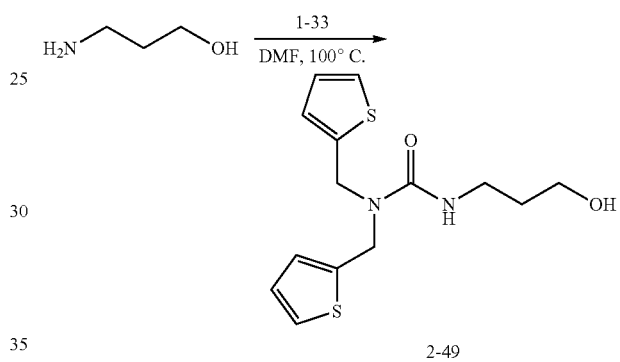

To a solution of 1-33 (0.100 g, 0.258 mmol) in N,N-dimethylformamide (0.25 mL), 3-amino-1-propanol (0.080 mL, 1.1 mmol) was added. and heated at 100° C. for 1 hour. The reaction mixture was heated to 100° C. for 1 hour, diluted with ethyl acetate, and washed with aqueous HCl (2N) and brine. The organic layer was dried over sodium sulfate, decanted and concentrated. The residue was purified by chromatography on silica gel, eluting with hexanes:ethyl acetate (1:1) to give the title compound 2-49 as a yellow oil (36.8 mg).

Example 22

Preparation of (2S)-2-acetamidohexyl bis(2-thienylmethyl)carbamate (2-64)

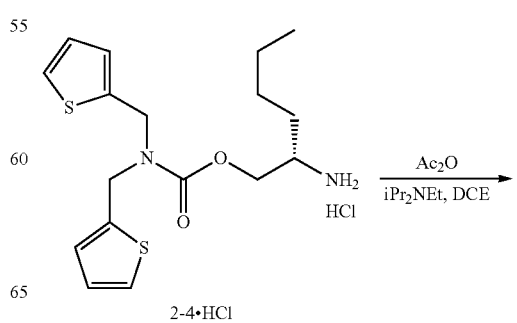

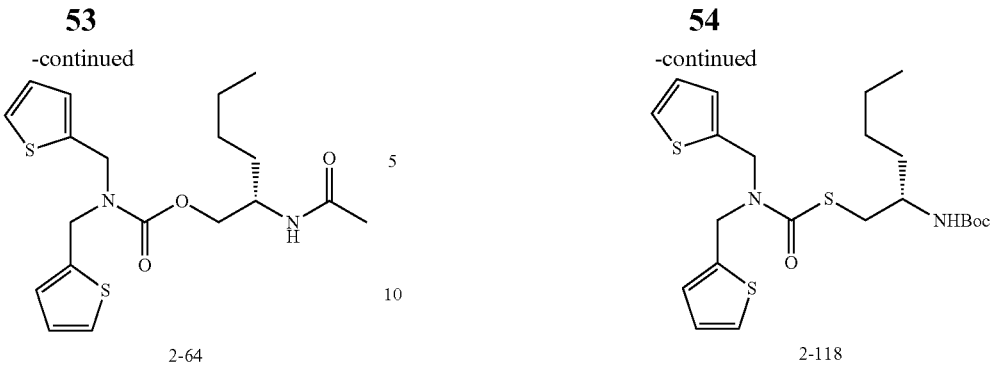

2-64

2-118

To a solution of 2-4.HCl (22 mg, 0.057 mmol) in 1,2-dichloroethane (0.4 mL) at room temperature, N,N-diisopropylethylamine (0.040 mL, 0.23 mmol) and acetic anhydride (0.0065 mL, 0.069 mmol) were added. The mixture was stirred overnight, diluted with 1:1 hexanes:ethyl acetate, and washed with saturated aqueous sodium bicarbonate and brine, dried over magnesium sulfate, filtered, and concentrated under reduced pressure. The organic layer was dried over magnesium sulfate, filtered, and concentrated under reduced pressure. The residue was purified by silica gel chromatography, eluting with hexanes:ethyl acetate (3:1 to 1:1) to give the title compound 2-64 as a white solid (17 mg).

This procedure was also used to prepare: (2R)-2-acetamido-N,N-bis(2-thienylmethyl)hexanamide (3-60) from 3-57; benzyl{(5S)-5-acetamido-6-[bis(2-thienylmethyl)amino]-6-oxohexyl}carbamate (3-73) from 3-66.HCl; and benzyl{(5S)-5-[acetyl(methyl)amino]-6-[bis(2-thienylmethyl)amino]-6-oxohexyl}carbamate (3-85) from 3-84.

Alternately, triethylamine could be used in place of N,N-diisopropylethylamine and/or dichloromethane could be used in place of dichloroethane. This variation was used to prepare (2S)-2-acetamido-N,N-bis(2-thienylmethyl)hexanamide (3-37) from 3-13.

Example 23

Preparation of tert-butyl[(2S)-1-{[bis(2-thienylmethyl)carbamoyl]thio}hexan-2-yl]carbamate (2-118)

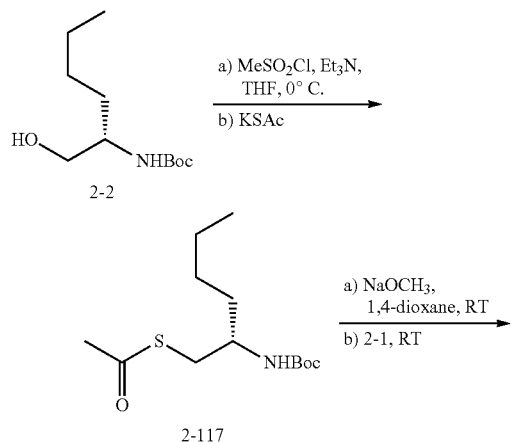

I. S-{(2S)-2-[(tert-Butoxycarbonyl)amino]hexyl}ethanethioate (2-117)

To a stirred solution of 2-2 (0.192 g, 0.88 mmol) and triethylamine (0.37 mL, 2.6 mmol) in dichloromethane (3 mL) at 0° C. under a dry nitrogen atmosphere, methanesulfonyl chloride (0.10 mL, 1.3 mmol) was added dropwise. After 50 minutes, potassium thioacetate (132 mg, 1.2 mmol) was added and the reaction was allowed to warm to room temperature slowly and stirred overnight. The reaction was diluted with saturated aqueous sodium bicarbonate and extracted with hexanes:ethyl acetate (1:1, three times). The organic layers were combined and washed with aqueous hydrochloric acid (0.1 N), saturated aqueous sodium bicarbonate, water, and saturated brine, dried over magnesium sulfate, filtered, and concentrated under reduced pressure. The residue was purified by automated silica gel chromatography (Biotage®), eluting with a hexanes:ethyl acetate gradient to give the title compound 2-117 as a low-melting solid (34 mg).

II. tert-Butyl[(2S)-1-{[bis(2-thienylmethyl)carbamoyl]thio}hexan-2-yl]carbamate (2-118)

To a solution of 2-117 (29 mg, 0.10 mmol) in 1,4-dioxane (1 mL) under a dry nitrogen atmosphere, sodium methoxide (7.2 mg, 0.13 mmol) was added. The reaction was stirred at room temperature for 2 hours, additional sodium methoxide (2 mg, 0.037 mmol) was added and the reaction was stirred for 1.5 hours. To the resulting mixture, 2-2 (0.050 g, 0.18 mmol) was added dropwise, and the reaction was stirred for 75 minutes and diluted with hexanes:ethyl acetate (1:1). The mixture was washed with water (3 rimes) and brine, dried over sodium sulfate, filtered, and concentrated under reduced pressure. The residue was purified by automated silica gel chromatography (Biotage®), eluting with a hexanes:ethyl acetate gradient to give the title compound 2-118 as a colorless crystalline solid (25 mg).

Example 24

Preparation of tert-butyl{2-[bis(2-thienylmethyl)amino]-2-oxoethyl}carbamate (3-1)

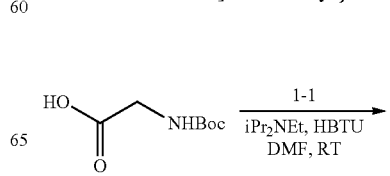

-continued

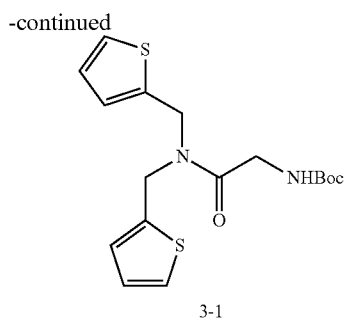
3-1

To a solution of Boc-Gly-OH (200 mg, 1.14 mmol) in N,N-dimethylformamide (4.5 mL), diisopropylethylamine (0.44 mL, 2.5 mmol), and HBTU (500 mg, 1.25 mmol) were added sequentially. The mixture was stirred at room temperature for 30 minutes and 1-1 (278 mg, 1.14 mmol) was added. The resulting mixture was stirred for 48 hours, diluted with hexanes:ethyl acetate (1:1), and washed with aqueous HCl (2N), water, saturated aqueous sodium chloride. The organic layer was dried over sodium sulfate, filtered and concentrated under reduced pressure. The residue was purified on silica gel with hexanes:ethyl acetate (3:1) to give the title compound 3-1 as a clear oil (0.30 g).

The amine/amine hydrochloride and the carboxylic acid were typically premixed prior to adding N,N-diisopropylethylamine and HBTU. This procedure was also used to prepare: tert-butyl{3-[bis(2-thienylmethyl)amino]-3-oxopropyl}carbamate (3-4) from Boc-alanine and 1-1; tert-butyl{2-[bis(2-thienylmethyl)amino]-2-oxoethyl}(methyl)carbamate (3-9) from 3-8 and 1-1; tert-butyl{(2R)-1-[bis(2-thienylmethyl)amino]-1-oxohexan-2-yl}carbamate (3-10) from Boc-D-Nle-OH and 1-1; tert-butyl{(2S)-1-[bis(2-thienylmethyl)amino]-1-oxohexan-2-yl}carbamate (3-12) from Boc-Nle-OH and 1-1; benzyl{(5S)-5-[(tert-butoxycarbonyl)amino]-6-[(4-nitrobenzyl)(2-thienylmethyl)amino]-6-oxohexyl}carbamate (3-21) from Boc-Lys(Z)—OH and 1-27; benzyl{(5R)-5-[(tert-butoxycarbonyl)amino]-6-[(4-nitrobenzyl)(2-thienylmethyl)amino]-6-oxohexyl}carbamate (3-23) from Boc-D-Lys(Z)—OH and 1-27; benzyl{(5R)-5-[(tert-butoxycarbonyl)amino]-6-[(3-methoxybenzyl)(2-thienylmethyl)amino]-6-oxohexyl}carbamate (3-25) from Boc-D-Lys(Z)—OH and 1-2; benzyl{(5S)-5-[(tert-butoxycarbonyl)amino]-6-[(3-methoxybenzyl)(2-thienylmethyl)amino]-6-oxohexyl}carbamate (3-26) from Boc-Lys(Z)—OH and 1-2; benzyl{(5R)-6-[bis(3-methoxybenzyl)amino]-5-[(tert-butoxycarbonyl)amino]-6-oxohexyl}carbamate (3-27) from Boc-D-Lys(Z)—OH and 1-3; benzyl{(5S)-6-[bis(3-methoxybenzyl)amino]-5-[(tert-butoxycarbonyl)amino]-6-oxohexyl}carbamate (3-28) from Boc-Lys(Z)—OH and 1-3; benzyl[(5R)-5-[(tert-butoxycarbonyl)amino]-6-oxo-6-{[2-(2-thienyl)ethyl](2-thienylmethyl)amino}hexyl]carbamate (3-29) Boc-D-Lys(Z)—OH and 1-5; -benzyl[(5S)-5-[(tert-butoxycarbonyl)amino]-6-oxo-6-{[2-(2-thienyl)ethyl](2-thienylmethyl)amino}hexyl]carbamate (3-30) from Boc-Lys(Z)—OH and 1-5; benzyl{(5S)-5-[(tert-butoxycarbonyl)amino]-6-[butyl(2-thienylmethyl)amino]-6-oxohexyl}carbamate (3-31) from Boc-Lys(Z)—OH and 1-9; benzyl{(5S)-6-[bis(4-methoxybenzyl)amino]-5-[(tert-butoxycarbonyl)amino]-6-oxohexyl}carbamate (3-32) from Boc-Lys(Z)—OH and 1-6; benzyl{(5S)-5-[(tert-butoxycarbonyl)amino]-6-oxo-6-[(pyridin-3-ylmethyl)(2-thienylmethyl)amino]hexyl}carbamate (3-33) from Boc-Lys(Z)—OH and 1-4; benzyl{(5S)-6-[bis(pyridin-4-ylmethyl)amino]-5-[(tert-butoxycarbonyl)amino]-6-oxohexyl}carbamate (3-34) from Boc-Lys(Z)—OH and 1-8; benzyl{(5S)-5-[(tert-butoxycarbonyl)amino]-6-oxo-6-[(pyridin-4-ylmethyl)(2-thienylmethyl)amino]hexyl}carbamate (3-36) from Boc-Lys(Z)—OH and 1-15; tert-butyl{(2S)-1-[bis(2-thienylmethyl)amino]-6-hydroxy-1-oxohexan-2-yl}carbamate (3-41) from (S)-2-(tert-butoxycarbonylamino)-6-hydroxyhexanoic acid and 1-1; methyl(5S)-6-[bis(2-thienylmethyl)amino]-5-[(tert-butoxycarbonyl)amino]-6-oxohexanoate (3-43) from 3-42 and 1-1; benzyl{(5R)-6-[bis(2-thienylmethyl)amino]-5-[(tert-butoxycarbonyl)amino]-6-oxohexyl}carbamate (3-62) from Boc-(D)-Lys(Z)—OH and 1-1; benzyl{(5S)-6-[bis(2-thienylmethyl)amino]-5-[(tert-butoxycarbonyl)amino]-6-oxohexyl}carbamate (3-65) from Boc-Lys(Z)—OH and 1-1; and N,N,N'-tris(2-thienylmethyl)pentanediamide (6-2) from 6-1 and 2-thiophenemethylamine; N-(3-methoxybenzyl)-N,N',N'-tris(2-thienylmethyl)pentanediamide (6-3) from 6-1 and 1-2; N'-[2-(2-thienyl)ethyl]-N,N-bis(2-thienylmethyl)pentanediamide (6-4) from 6-1 and 2-(2-thienyl)ethylamine; N-[2-(2-thienyl)ethyl]-N,N',N'-tris(2-thienylmethyl)pentanediamide (6-5) from 6-1 and 1-5; N,N-bis(3-methoxybenzyl)-N',N'-bis(2-thienylmethyl)pentanediamide (6-6) from 6-1 and 1-3; N,N-bis(pyridin-4-ylmethyl)-N',N'-bis(2-thienylmethyl)pentanediamide (6-7) from 6-1 and 1-8; N,N-bis(pyridin-3-ylmethyl)-N',N'-bis(2-thienylmethyl)pentanediamide (6-8) from 6-1 and 1-7; benzyl{(5S)-6-{bis[4-(trifluoromethoxy)benzyl]amino}-5-[(tert-butoxycarbonyl)amino]-6-oxohexyl}carbamate (3-130) from Boc-Lys(Z)—OH and 1-41; benzyl[(5S)-5-[(tert-butoxycarbonyl)amino]-6-oxo-6-{(2-thienylmethyl)[2-(trifluoromethyl)benzyl]amino}hexyl]carbamate (3-131) from Boc-Lys(Z)—OH and 1-38; benzyl[(5S)-5-[(tert-butoxycarbonyl)amino]-6-oxo-6-{(2-thienylmethyl)[2-(trifluoromethoxy)benzyl]amino}hexyl]carbamate (1-132) from Boc-Lys(Z)—OH and 1-39; benzyl[(5S)-5-[(tert-butoxycarbonyl)amino]-6-{[2-(difluoromethoxy)benzyl](2-thienylmethyl)amino}-6-oxohexyl]carbamate (1-133) from Boc-Lys(Z)—OH and 1-40; tert-butyl{6-[bis(4-methoxybenzyl)amino]-6-oxohexyl}carbamate (3-134) from Boc-6-Ahx-OH and 1-6; 8-hydroxy-N,N-bis(2-thienylmethyl)quinoline-2-carboxamide (4-45) from 8-hydroxyquinoline-2-carboxylic acid and 1-1; 6-bromo-N,N-bis(2-thienylmethyl)nicotinamide (4-46) from 6-bromonicotinic acid and 1-1; methyl 3-[bis(2-thienylmethyl)carbamoyl]benzoate (4-47) from mono-methyl isophthalate and 1-1; tert-butyl{4-[bis(2-thienylmethyl)amino]-4-oxobutyl}carbamate (3-145) from 3-144 and 1-1; 4-(1,1-dioxido-1,2-thiazolidin-2-yl)-N,N-bis(2-thienylmethyl)butanamide (3-163) from 3-162 and 1-1; benzyl{(5S)-6-[bis(cyclopropylmethyl)amino]-5-[(tert-butoxycarbonyl)amino]-6-oxohexyl}carbamate (3-176) from Boc-Lys(Z)—OH and 1-48; benzyl{(5S)-5-[(tert-butoxycarbonyl)amino]-6-[(cyclopropylmethyl)(2-thienylmethyl)amino]-6-oxohexyl}carbamate (3-177) from Boc-Lys(Z)—OH and 1-49; tert-butyl{(2S)-1,6-bis[bis(2-thienylmethyl)amino]-1,6-dioxohexan-2-yl}carbamate (6-34) from 6-33 and 1-1; 2-({2-[bis(2-thienylmethyl)sulfamoyl]ethyl}amino)-N,N-bis(2-thienylmethyl)acetamide (7-21) from 7-20 and 1-1 (3 equivalents); 3-({2-[bis(2-thienylmethyl)sulfamoyl]ethyl}amino)-N,N-bis(2-thienylmethyl)propanamide (7-28) from 7-27 and 1-1 (3 equivalents); 3-({2-[bis(2-thienylmethyl)sulfamoyl]ethyl}amino)-N,N-bis(4-methoxybenzyl)propanamide (7-29) from 7-27 and 1-6 (3 equivalents); 2-(acetyl{2-[bis(2-thienylmethyl)sulfamoyl]ethyl}amino)-N,N-bis(2-thienylmethyl)acetamide (7-40) from 7-39 and 1-1; and 2-(acetyl{2-[bis(4-methoxybenzyl)sulfamoyl]ethyl}amino)-N,N-bis(2-thienylmethyl)acetamide (7-44) from 7-43 and 1-1.

Alternately, a dicarboxylic acid could be reacted with 2 equivalents each of an amine hydrochloride and HBTU in the presence of 8 equivalents N,N-diisopropylethylamine. This variation was used to prepare: N,N,N',N'-tetrakis(2-thienylmethyl)pyridine-3,5-dicarboxamide (6-27) from 3,5-pyridinedicarboxylic acid and 1-1; N,N,N',N'-tetrakis(2-thienylmethyl)pyridine-2,6-dicarboxamide (6-28) from 2,6-pyridinedicarboxylic acid and 1-1; N,N,N',N'-tetrakis(2-thienylmethyl)pyridine-2,4-dicarboxamide (6-29) from 2,4-pyridinedicarboxylic acid and 1-1; and 2,2'-(1,4-phenylene)bis[N,N-bis(2-thienylmethyl)acetamide](6-30) from 1,4-phenylenediacetic acid and 1-1.

In another variation, COMU® could be used in place of HBTU. This variation was used to prepare: benzyl {(3S)-4-[bis(thiophen-2-ylmethyl)amino]-3-[(tert-butoxycarbonyl)amino]-4-oxobutyl}carbamate (3-69) from Boc-Dab(Z)—OH (prepared from Boc-Dab(Z)—OH.DCHA according to the procedure described in technical notes at www.bachem.com (conversion of a DCHA salt to the free acid)) and 1-1; benzyl {(4S)-5-[bis(2-thienylmethyl)amino]-4-[(tert-butoxycarbonyl)amino]-5-oxopentyl}carbamate (3-70) from Boc-Orn(Z)—OH and 1-1; benzyl {(5S)-5-[(tertbutoxycarbonyl)amino]-6-[methyl(2-thienylmethyl)amino]-6-oxohexyl}carbamate (3-72) from Boc-Lys(Z)—OH and 2-32; benzyl {(5S)-6-[bis(2-thienylmethyl)amino]-6-oxo-5-[(3-phenoxypropanoyl)amino]hexyl}carbamate (3-75) from 3-66 and 3-phenoxyproprionic acid; methyl (4S)-5-[bis(2-thienylmethyl)amino]-4-[(tert-butoxycarbonyl)amino]-5-oxopentanoate (3-81) from Boc-Glu(OMe)-OH (prepared from Boc-Glu(OMe)-OH.DCHA) and 1-1; tert-butyl [(2S)—I-[bis(2-thienylmethyl)amino]-3-(4-hydroxyphenyl)-I-oxopropan-2-yl]carbamate (3-82) from Boc-Tyr-OH and 1-1; benzyl {(5S)-6-[bis(2-thienylmethyl)amino]-5-[(tertbutoxycarbonyl)(methyl)amino]-6-oxohexyl}carbamate (3-83) from Boc-N-Me-Lys(Z)—OH (prepared from Boc-N-Me-Lys(Z)—OHeDCHA) and 1-1; tert-butyl {(2S)-6-acetamido-I-[bis(2-thienylmethyl)amino]-I-oxohexan-2-yl}carbamate (3-89) from H-Lys(Ac)-OH and 1-1; tert-butyl {(2S)—I-[bis(2-thienylmethyl)amino]-I-oxo-6-[(trifluoroacetyl)amino]hexan-2-yl}carbamate (3-90) from Boc-Lys(Tfa)-OH and 1-1; 9H-fluoren-9-ylmethyl {(SS)-6-[bis(2-thienylmethyl)amino]-S-[(tert-butoxycarbonyl)amino]-6-oxohexyl}carbamate (3-91) from BocLys(Fmoc)-OH and 1-1; tert-butyl {(2S)—I-[bis(2-thienylmethyl)amino]-I-oxo-6-[(2-thienylcarbonyl)amino]hexan-2-yl}carbamate (3-9S) from 2-thiophenecarboxylic acid and 3-92; tert-butyl {(2S)—I-[bis(2-thienylmethyl)amino]-I-oxo-6-[(pyridin-3-ylcarbonyl)amino]hexan-2-yl}carbamate (3-97) from Boc-Lys(nicotinoyl)-OH and 1-1; tert-butyl {6-[bis(thiophen-2-ylmethyl)amino]-6-oxohexyl}carbamate (3-102) from Boc-6-Ahx-OH and 1-1; N-{6-[bis(2-thienylmethyl)amino]-6-oxohexyl}-N-(2-thienylmethyl)thiophene-2-carboxamide (3-106) from 3-10S and 2-thiophenecarboxylic acid; N-{6-[bis(2-thienylmethyl)amino]-6-oxohexyl}thiophene-2-carboxamide (3-107) from 3-103 and 2-thiophenecarboxylic acid; benzyl [(SS)—S-[(tert-butoxycarbonyl)amino]-6-(dibenzylamino)-6-oxohexyl]carbamate (3-117) from Boc-Lys(Z)—OH and dibenzylamine; tert-butyl [(IR)-2-[bis(2-thienylmethyl)amino]-1-(4-hydroxyphenyl)-2-oxoethyl]carbamate (3-119) from 3-118 and 1-1; benzyl {(SS)-6-[(4-bromobenzyl)(2-thienylmethyl)amino]-S-[(tert-butoxycarbonyl)amino]-6-oxohexyl}carbamate (3-172) from Boc-Lys(Z)—OH and 1-4S, tert-butyl {(2S)—I-[(4-bromobenzyl)(2-thienylmethyl)amino]-I-oxohexan-2-yl}carbamate (3-174) from Boc-Nle-OH and 1-4S; and benzyl {(SS)-6-[bis(3-thienylmethyl)amino]-S-[(tert-butoxycarbonyl)amino]-6-oxohexyl}carbamate (3-17S) from Boc-Lys(Z)—OH and 1-50.

Example 25

Preparation of [(tert-butoxycarbonyl)(methyl)amino]acetic acid (3-8)

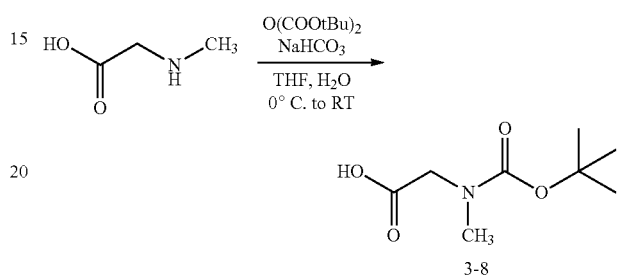

To a suspension of sarcosine (223 mg, 2.5 mmol) in tetrahydrofuran (4 mL) and water (4 mL), sodium bicarbonate (0.28 g, 3.3 mmol) and di-tert-butyl dicarbonate (0.55 g, 2.5 mmol) were added. The mixture was stirred at room temperature overnight, diluted with hexanes:ethyl acetate (3:1). The aqueous layer was acidified with aqueous HCl (2N) and extracted with ethyl acetate (twice). The two ethyl acetate extracts were combined, washed with brine, dried over sodium sulfate, filtered and concentrated to give the title compound 3-8 as a clear oil (0.53 g).

This procedure was also used to prepare (2S)-2-[(tert-butoxycarbonyl)amino]-6-methoxy-6-oxohexanoic acid (3-42) from (S)-2-amino-6-methoxy-6-oxohexanoic acid hydrochloride (H-Aad(OMe)-OH.HCl).

Alternately, sodium hydroxide and dioxane could be used in place of sodium bicarbonate and tetrahydrofuran. This variation was used to prepare (2R)-[(tert-butoxycarbonyl)amino](4-hydroxyphenyl)acetic acid (3-118) from D-(−)-4-hydroxyphenylglycine.

Example 26

Preparation of (2S)-2-[(methylsulfonyl)amino]-N,N-bis(2-thienylmethyl)hexanamide (3-14)

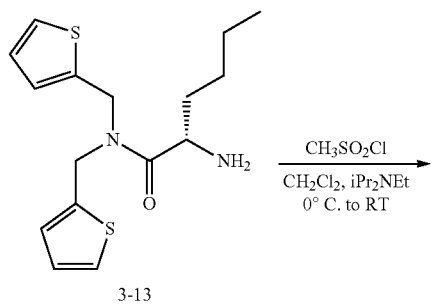

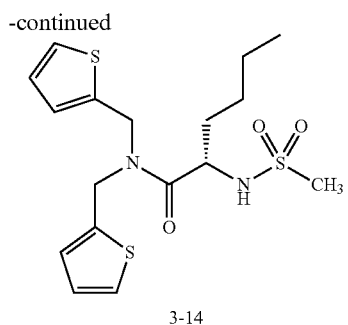

3-14

To a solution of 3-13 (50 mg, 0.15 mmol) and N,N-diisopropylethylamine (0.028 mL, 0.16 mmol) in dichloromethane (0.750 mL) at 0° C., methanesulfonyl chloride (0.013 mL, 0.16 mmol) was added. The ice bath has been removed, and the reaction was stirred at room temperature for 1 hour. The mixture was diluted with dichloromethane, washed with aqueous HCl (2N) and brine, dried over sodium sulfate, and concentrated under reduced pressure to give the title compound 3-14 as a tan solid (46.2 mg).

For this procedure, or any of the following variations, and amine hydrochloride may be used in place of the amine by increasing the amount of tertiary amine base. Also, dichloroethane or tetrahydrofuran could be used interchangeably with dichloromethane.

This procedure was also used to prepare: (2S)-2-[(phenylsulfonyl)amino]-N,N-bis(2-thienylmethyl)hexanamide (3-15) from 3-13 and benzenesulfonyl chloride; 2-[methyl(phenylsulfonyl)amino]-N,N-bis(2-thienylmethyl)acetamide (3-18) from 3-17 and benzenesulfonyl chloride; and (2S)-2-({[3-(4-methoxyphenoxy)propyl]sulfonyl}amino)-N,N-bis(2-thienylmethyl)hexanamide (3-56) from 3-13 and 3-(4-methoxyphenoxy)-1-propanesulfonyl chloride.

Alternately, triethylamine may be used in place of N,N-diisopropylethylamine. This variation was used to prepare: benzyl{(5S)-6-[bis(2-thienylmethyl)amino]-6-oxo-5-[(2-thienylsulfonyl)amino]hexyl}carbamate (3-88) from 3-66 and 2-thiophenesulfonyl chloride; tert-butyl{(2S)-1-[bis(2-thienylmethyl)amino]-1-oxo-6-[(phenylsulfonyl)amino]hexan-2-yl}carbamate (3-96) from 3-92 and benzenesulfonyl chloride; tert-butyl{(2S)-6-[(benzylsulfonyl)amino]-1-[bis(2-thienylmethyl)amino]-1-oxohexan-2-yl}carbamate (3-99) from 3-92 and phenylmethanesulfonyl chloride; tert-butyl[(2S)-1-[bis(2-thienylmethyl)amino]-1-oxo-6-{[(trifluoromethyl)sulfonyl]amino}hexan-2-yl]carbamate (3-101) from 3-92 and trifluoromethanesulfonyl chloride; N,N-bis(2-thienylmethyl)-6-[(2-thienylsulfonyl)amino]hexanamide (3-104) from 3-103 and 2-thiophenesulfonyl chloride; 6-[(benzylsulfonyl)amino]-N,N-bis(2-thienylmethyl)hexanamide (3-111) from 3-103 and phenylmethanesulfonyl chloride; 2-[(phenylsulfonyl)amino]-N,N-bis(2-thienylmethyl)acetamide (3-125) from 3-2.HCl and benzenesulfonyl chloride; N,N-bis(2-thienylmethyl)methanesulfonamide (4-3) from 1-1 and methanesulfonyl chloride; N,N-bis(2-thienylmethyl)benzenesulfonamide (4-4) from 1-1 and benzenesulfonyl chloride; 2-chloro-N,N-bis(2-thienylmethyl)benzenesulfonamide (4-5) from 1-1 and 2-chlorobenzenesulfonyl chloride; 3-chloro-N,N-bis(2-thienylmethyl)benzenesulfonamide (4-6) from 1-1 and 3-chlorobenzenesulfonyl chloride; 4-chloro-N,N-bis(2-thienylmethyl)benzenesulfonamide (4-7) from 1-1 and 4-chlorobenzenesulfonyl chloride; 4-methoxy-N,N-bis(2-thienylmethyl)benzenesulfonamide (4-8) from 1-1 and 4-methoxybenzenesulfonyl chloride; 3-methoxy-N,N-bis(2-thienylmethyl)benzenesulfonamide (4-9) from 1-1 and 3-methoxybenzenesulfonyl chloride; 4-methyl-N,N-bis(2-thienylmethyl)benzenesulfonamide (4-10) from 1-1 and 4-methylbenzenesulfonyl chloride; 2-methyl-N,N-bis(2-thienylmethyl)benzenesulfonamide (4-11) from 1-1 and 2-methylbenzenesulfonyl chloride; 3-methyl-N,N-bis(2-thienylmethyl)benzenesulfonamide (4-12) from 1-1 and 3-methylbenzenesulfonyl chloride; N,N-bis(4-methoxybenzyl)benzenesulfonamide (4-13) from 1-6 and benzenesulfonyl chloride in tetrahydrofuran; N,N-bis(4-methoxybenzyl)thiophene-2-sulfonamide (4-14) from 1-6 and 2-thiophenesulfonyl chloride; N,N-bis(3-methoxybenzyl)thiophene-2-sulfonamide (4-15) from 1-3 and 2-thiophenesulfonyl chloride; methyl 3-[bis(3-methoxybenzyl)sulfamoyl]thiophene-2-carboxylate (4-16) from 1-3 and 2-carbomethoxy-3-thiophenesulfonyl chloride; N-(2-methoxyethyl)-N-(2-thienylmethyl)thiophene-2-sulfonamide (4-17) from 1-12 and 2-thiophenesulfonyl chloride; N-butyl-N-(2-thienylmethyl)benzenesulfonamide (4-18) from 1-9 and benzenesulfonyl chloride in tetrahydrofuran; N-(3-hydroxypropyl)-N-(2-thienylmethyl)benzenesulfonamide (4-19) from 1-13 and benzenesulfonyl chloride; N,N-bis(pyridin-3-ylmethyl)benzenesulfonamide (4-20) from 1-7 and benzenesulfonyl chloride; N,N-bis(pyridin-4-ylmethyl)benzenesulfonamide (4-21) from 1-8 and benzenesulfonyl chloride; N-(pyridin-3-ylmethyl)-N-(2-thienylmethyl)benzenesulfonamide (4-22) from 1-4 and benzenesulfonyl chloride in tetrahydrofuran; N-(2-furylmethyl)-N-(2-thienylmethyl)benzenesulfonamide (4-23) from 1-10 and benzenesulfonyl chloride; N,N-bis(2-furylmethyl)benzenesulfonamide (4-24) from 1-11 and benzenesulfonyl chloride; N-(3-methoxybenzyl)-N-(2-thienylmethyl)benzenesulfonamide (4-25) from 1-2 and benzenesulfonyl chloride; N,N-bis(3-methoxybenzyl)benzenesulfonamide (4-26) from 1-3 and benzenesulfonyl chloride in dichloroethane; N-[2-(2-thienyl)ethyl]-N-(2-thienylmethyl)benzenesulfonamide (4-27) from 1-5 and benzenesulfonyl chloride in dichloroethane; N,N-dibenzylbenzenesulfonamide (4-28) from dibenzylamine and benzenesulfonyl chloride; 2-methyl-N,N-bis(2-thienylmethyl)propane-1-sulfonamide (4-29) from 1-1 and isobutanesulfonyl chloride; N-phenyl-N-(2-thienylmethyl)benzenesulfonamide (4-30) from 1-30 and benzenesulfonyl chloride; N-(2-thienylmethyl)propane-2-sulfonamide (4-32) from 2-thiophenemethylamine and isopropylsulfonyl chloride; 2-methyl-N-(2-thienylmethyl)propane-1-sulfonamide (4-34) from 2-thiophenemethylamine and isobutanesulfonyl chloride; N-phenylthiophene-2-sulfonamide (4-36) from aniline and 2-thiophenesulfonyl chloride; N-phenylbenzenesulfonamide (4-38) from aniline and benzenesulfonyl chloride; N-(2-methoxyethyl)-N-(2-thienylmethyl)benzenesulfonamide (4-41) from 1-12 and benzenesulfonyl chloride; 1-phenyl-N,N-bis(2-thienylmethyl)methanesulfonamide (4-43) from 1-1 and phenylmethanesulfonyl chloride; methyl(2S)-6-{[(benzyloxy)carbonyl]amino}-2-[(phenylsulfonyl)amino]hexanoate (5-1) from H-Lys(Z)—OMe.HCl and benzenesulfonyl chloride; methyl (2S)-6-{[(benzyloxy)carbonyl]amino}-2-[(2-thienylsulfonyl)amino]hexanoate (5-3) from H-Lys(Z)—OMe.HCl and 2-thiophenesulfonyl chloride; methyl(2S)-6-{[(benzyloxy)carbonyl]amino}-2-[(isobutylsulfonyl)amino]hexanoate (5-7) from H-Lys(Z)—OMe.HCl and isobutanesulfonyl chloride; benzyl{(5S)-5-[(tert-butoxycarbonyl)amino]-6-[(2-thienylmethyl)(2-thienylsulfonyl)amino] hexyl}carbamate (5-12) from 5-11 and 2-thiophenesulfonyl chloride; benzyl{(5S)-5-[(tert-butoxycarbonyl)amino]-6-[(phenylsulfonyl)(2-thienylmethyl)amino]hexyl}carbamate (5-13) from 5-11 and benzenesulfonyl chloride; benzyl {(5S)-5-[(tert-butoxycarbonyl)amino]-6-[(methylsulfonyl) (2-thienylmethyl)amino]hexyl}carbamate (5-15) from 5-11 and methanesulfonyl chloride; benzyl[(5S)-5-[(tert-butoxycarbonyl)amino]-6-{[(4-methoxyphenyl)sulfonyl](2-thienylmethyl)amino}hexyl]carbamate (5-17) from 5-11 and 4-methoxybenzenesulfonyl chloride; 6-{[(3-chloropropyl)sulfonyl]amino}-N,N-bis(4-methoxybenzyl)hexanamide (3-150) from 3-135 and 3-chloropropanesulfonyl chloride; methyl 4-{[(3-chloropropyl)sulfonyl]amino}butanoate (3-160) from 4-aminobutyric acid methyl ester hydrochloride and 3-chloropropanesulfonyl chloride; tert-butyl{5-[(2-thienylsulfonyl)amino]pentyl}carbamate (5-29) from N-1-Boc-1-5-diaminopentane hydrochloride and 2-thiophenesulfonyl chloride; N-{2-[bis(2-thienylmethyl)sulfamoyl]ethyl}-N-(2-thienylmethyl)thiophene-2-sulfonamide (7-2) from 7-1 and 2-thiophenesulfonyl chloride; N-(2-thienylmethyl)thiophene-2-sulfonamide (7-8) from 2-thiophenemethylamine and 2-thiophenesulfonyl chloride; 3-chloro-N,N-bis(2-thienylmethyl)propane-1-sulfonamide (7-9) from 1-1 and 3-chloropropanesulfonyl chloride; 2-[(methylsulfonyl)(2-thienylmethyl)amino]-N,N-bis(2-thienylmethyl)ethanesulfonamide (7-11) from 7-1 and methanesulfonyl chloride; 2-(1,3-dioxo-1,3-dihydro-2H-isoindol-2-yl)-N,N-bis(2-thienylmethyl)ethanesulfonamide (7-12) from 1-1 and 2-(phthalimido)ethanesulfonyl chloride; and N-{2-[bis(2-thienylmethyl)sulfamoyl]ethyl}thiophene-2-sulfonamide (7-15) from 7-13 and 2-thiophenesulfonyl chloride.

When 2-chloroethanesulfonyl chloride was used in this variation, concomitant beta-elimination of HCl accompanied formation of the sulfonamide. This method was used to prepare: N,N-bis(2-thienylmethyl)ethenesulfonamide (4-48) from 1-1; N,N-bis(4-methoxybenzyl)-6-[(vinylsulfonyl)amino]hexanamide (3-149) from 3-135; and N,N-bis(4-methoxybenzyl)ethenesulfonamide (7-30) from 1-6.

Pyridine was also used in place of N,N-diisopropylethylamine. This variation was used to prepare: tert-butyl{(2S)-1-[bis(2-thienylmethyl)amino]-1-oxo-6-[(2-thienylsulfonyl)amino]hexan-2-yl}carbamate (3-93) from 3-92 and 2-thiophenesulfonyl chloride; tert-butyl{(2S)-1-[bis(2-thienylmethyl)amino]-6-[(methylsulfonyl)amino]-1-oxohexan-2-yl}carbamate (3-94) from 3-92 and methanesulfonyl chloride; N-phenyl-N-(2-thienylmethyl)thiophene-2-sulfonamide (4-31) from 1-30 and 2-thiophenesulfonyl chloride; 3-(4-methoxyphenoxy)-N,N-bis(2-thienylmethyl)propane-1-sulfonamide (4-42) from 1-1*freebase (prepared by partitioning 1-1 between ethyl acetate and saturated aqueous sodium bicarbonate and drying, filtering and concentrating under vacuum) and 3-(4-methoxyphenoxy)-1-propanesulfonyl chloride in dichloroethane; and N-(4-hydroxybenzyl)-3-methoxy-N-(2-thienylmethyl)benzenesulfonamide (4-44) from 1-14 and 3-methoxybenzenesulfonyl chloride.

In another variation, a symmetrical diamine or diamine dihydrochloride was used in place of the amine, using 2.2 equivalents each of the sulfonyl chloride and N,N-diisopropylethylamine or triethylamine (4.4 equivalents base for the dihydrochloride) in dichloromethane to give symmetrical disulfonamides. This variation of the procedure was used to prepare: N,N'-heptane-1,7-diylbis[N-(2-thienylmethyl)thiophene-2-sulfonamide](5-22) from 5-19 and 2-thiophenesulfonyl chloride; N,N'-heptane-1,7-diyldithiophene-2-sulfonamide (5-23) from 1,7-heptanediamine and 2-thiophenesulfonyl chloride; and N,N'-pentane-1,5-diyldithiophene-2-sulfonamide (5-31) from cadaverine and 2-thiophenesulfonyl chloride.

Example 27

Preparation of (2S)-2-[methyl(phenylsulfonyl)amino]-N,N-bis(2-thienylmethyl)hexanamide (3-16)

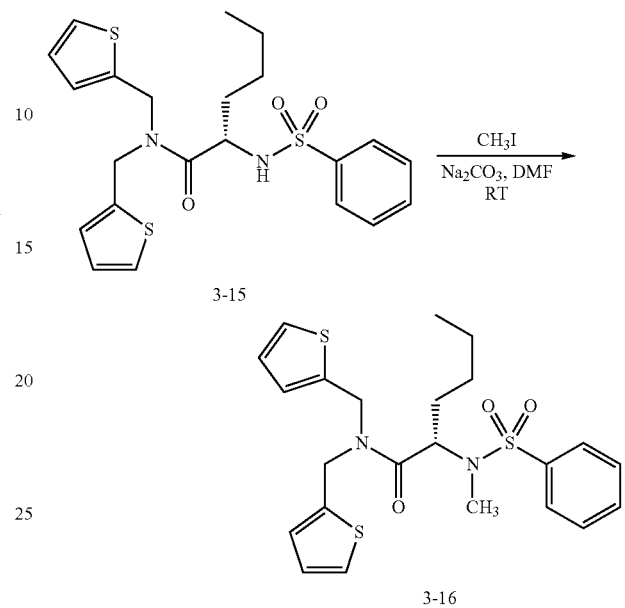

To a solution of 3-15 (0.15 mmol theoretical) in N,N-dimethylformamide (0.7 mL) at room temperature, sodium carbonate (0.25 g) and methyl iodide (0.070 mL) were added. The reaction mixture was heated at 90° C. in a sealed tube then was cooled to room temperature when the starting material was completely consumed. The resulting mixture was diluted with aqueous HCl (2N) and extracted with hexanes:ethyl acetate (2:1). The organic layer was washed with brine, dried over sodium sulfate, filtered, and concentrated under reduced pressure. The residue was purified by chromatography on silica gel using hexanes:ethyl acetate (4:1 to 3:1) to give the title compound give 3-16 as a light yellow semi-solid (27.9 mg).

This procedure was also used to prepare 6-[methyl(2-thienylsulfonyl)amino]-N,N-bis(2-thienylmethyl)hexanamide (3-110) from 3-104 at 50° C.

Alternately, cesium carbonate may be used in place of sodium carbonate and the reaction took place at room temperature. This variation was used to prepare: tert-butyl {(2S)-6-[benzyl(2-thienylsulfonyl)amino]-1-[bis(2-thienylmethyl)amino]-1-oxohexan-2-yl}carbamate (3-100) from 3-93 and benzylchloride; 6-[benzyl(2-thienylsulfonyl)amino]-N,N-bis(2-thienylmethyl)hexanamide (3-109) from 3-104 and benzyl chloride; N-(3-methoxybenzyl)-N-(2-thienylmethyl)propane-2-sulfonamide (4-33) from 4-32 and 3-methoxybenzyl bromide; N-(3-methoxybenzyl)-2-methyl-N-(2-thienylmethyl)propane-1-sulfonamide (4-35) from 4-34 and 3-methoxybenzyl bromide; N-(3-methoxybenzyl)-N-phenylthiophene-2-sulfonamide (4-37) from 4-36 and 3-methoxybenzyl bromide heating to 40° C.; N-(3-methoxybenzyl)-N-phenylbenzenesulfonamide (4-39) from 4-38 and 3-methoxybenzyl bromide; methyl(2S)-6-{[(benzyloxy)carbonyl]amino}-2-[benzyl(phenylsulfonyl)amino]hexanoate (5-2) from 5-1 and benzyl chloride; methyl(2S)-6-{[(benzyloxy)carbonyl]amino}-2-[benzyl(2-thienylsulfonyl)amino]hexanoate (5-4) from 5-3 and benzyl chloride; methyl (2S)-2-[benzyl(isobutylsulfonyl)amino]-6-{[(benzyloxy)carbonyl]amino}hexanoate (5-8) from 5-7 and benzyl chloride; tert-butyl{5-[(4-methoxybenzyl)(2-thienylsulfonyl)amino]pentyl}carbamate (5-30) from 5-29 and 4-methoxybenzyl chloride. This procedure was also used to affect the intramolecular cyclization of 3-160 (1.1 equivalents morpholine added in addition to cesium carbonate) to give methyl 4-(1,1-dioxido-1,2-thiazolidin-2-yl)butanoate (3-161), and the alkylation of 4-45 with alkyl bromide 1-37 to give 8-{2-[bis(2-thienylmethyl)amino]-2-oxoethoxy}-N,N-bis(2-thienylmethyl)quinoline-2-carboxamide (6-31).

In another variation, the reaction was attempted in dichloromethane at room temperature using N,N-diisopropylethylamine as the base. When the reaction failed to proceed, cesium carbonate was added and the reaction was complete after stirring overnight at room temperature. This variation was used to prepare 6-[(3-methoxybenzyl)(2-thienylsulfonyl)amino]-N,N-bis(2-thienylmethyl)hexanamide (3-114) from 3-104 and 3-methoxybenzyl bromide; 6-[(benzylsulfonyl)(3-methoxybenzyl)amino]-N,N-bis(2-thienylmethyl)hexanamide (3-116) from 3-111 and 3-methoxybenzyl bromide;

In yet another variation, a symmetrical disulfonamide, 5-23, was reacted with 4.2 equivalents 3-methoxybenzyl bromide, 3.4 equivalents of sodium carbonate, 2.4 equivalents sodium iodide in DMF at 85° C. to give N,N'-heptane-1,7-diylbis[N-(3-methoxybenzyl)thiophene-2-sulfonamide] (5-24). Another symmetrical disulfonamide, 5-31, was treated with 3-methoxybenzyl bromide and cesium carbonate at room temperature in DMF to give N,N'-pentane-1,5-diylbis[N-(3-methoxybenzyl)thiophene-2-sulfonamide](5-32).

Example 28

Preparation of tert-butyl[(2S)-1-[(4-aminobenzyl)(2-thienylmethyl)amino]-6-{[(benzyloxy)carbonyl]amino}-1-oxohexan-2-yl]carbamate (3-22)

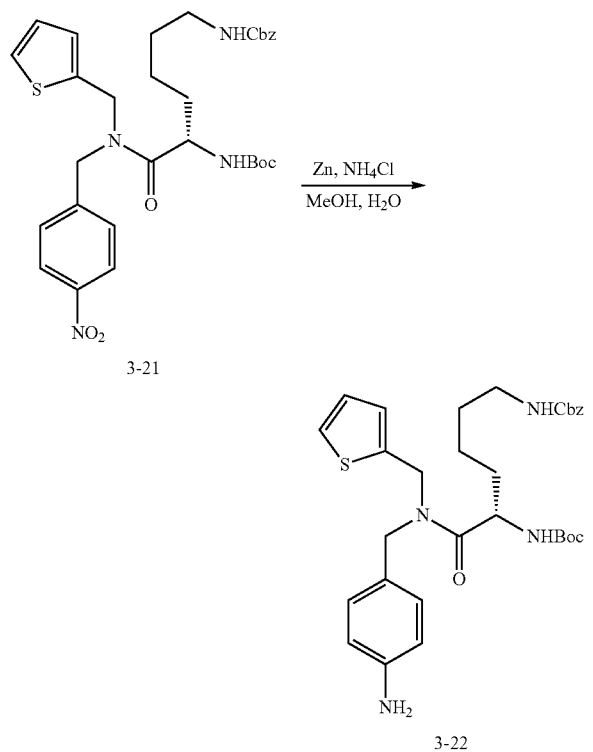

To a solution of 3-21 (105 mg, 0.172 mmol) in methanol (2.5 mL), zinc (45 mg; 0.69 mmol) and saturated aqueous ammonium chloride (2 mL) were added. The reaction mixture was heated at 50° C. for 3 hours, allowed to cool to room temperature, and filtered through Celite®, washing with methanol. The filtrate was concentrated under reduced pressure and the residue was taken up in ethyl acetate and saturated aqueous sodium bicarbonate. The aqueous layer was extracted with ethyl acetate (twice). The organic phases were combined, washed successively with water and brine, dried over magnesium sulfate, filtered, and concentrated under reduced pressure. The crude residue was purified by chromatography on silica gel eluting with hexanes:ethyl acetate (1:1) to give the title compound 3-22 as a yellow solid (45 mg).

This procedure was used to prepare tert-butyl[(2R)-1-[(4-aminobenzyl)(2-thienylmethyl)amino]-6-{[(benzyloxy)carbonyl]amino}-1-oxohexan-2-yl]carbamate (3-24) from 3-23.

Example 29

Preparation of (2S)-6-{[(benzyloxy)carbonyl]amino}-1-[bis(2-thienylmethyl)amino]-1-oxohexan-2-yl acetate (3-87)

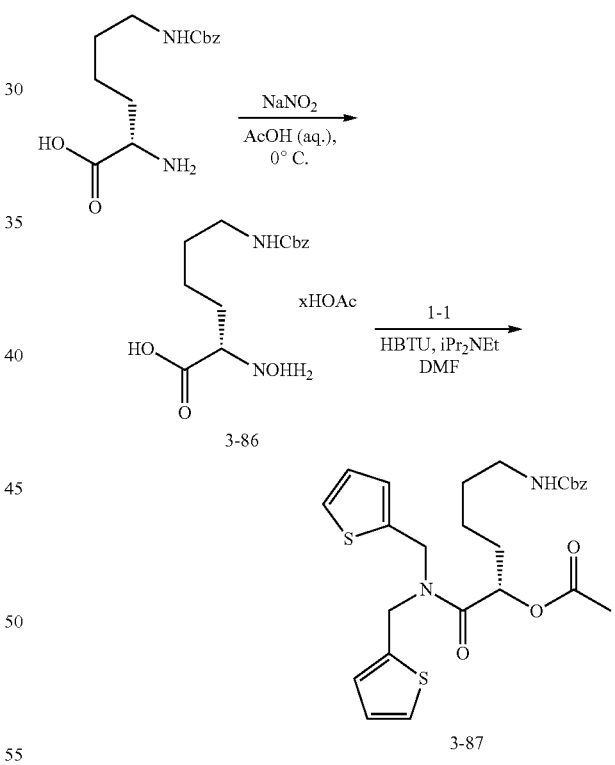

I. (2S)-6-{[(Benzyloxy)carbonyl]amino}-2-hydroxyhexanoic acid (3-86)

To a suspension of H-Lys(Z)—OH (2.0 g, 7.2 mmol) in aqueous acetic acid (50% v/v, 140 mL) at 0° C., a solution of sodium nitrite (3.7 g, 54 mmol) in water (10 mL) cooled to 0° C. was added dropwise. The resulting mixture was stirred 35 minutes, and the cold reaction was extracted with diethyl ether 4 times. The combined organic layers were washed twice with saturated brine, dried over magnesium sulfate, filtered, and concentrated under reduced pressure to give the title compound 3-86. This material contained acetic acid and other impurities in addition to 3-86 but was used in the subsequent reaction without purification.

II (2S)-6-{[(Benzyloxy)carbonyl]amino}-1-[bis(2-thienylmethyl)amino]-1-oxohexan-2-yl acetate (3-87)

To a solution of 3-86 (crude material from Step I, 7 mmol theoretical, contains acetic acid), 1-1 (4.5 g, 18 mmol) in and N,N-dimethylformamide (40 mL), N,N-diisopropylethylamine (6.5 mL, 37 mmol) and HBTU (7.5 g, 20 mmol) were added. The reaction was stirred at room temperature for 3 hours, then was diluted with water and extracted with hexanes:ethyl acetate (3:1, five times). The organic layer was washed with saturated aqueous sodium bicarbonate and brine, dried over magnesium sulfate, filter and concentrated under vacuum. The residue was purified by chromatography on silica gel eluting with a hexanes:ethyl acetate step gradient (20 to 55% in 7 steps of 5%). Fractions containing desired were concentrated and the residue was purified further by automated column chromatography (Biotage®) on silica gel, eluting with an ethyl acetate/hexanes gradient (30 to 50%) with methanol (1% constant) to give 3-87 as a light yellow syrup (0.45 g).

Example 30

Preparation of tert-butyl{(2S)-6-amino-1-[bis(2-thienylmethyl)amino]-1-oxohexan-2-yl}carbamate (3-92)

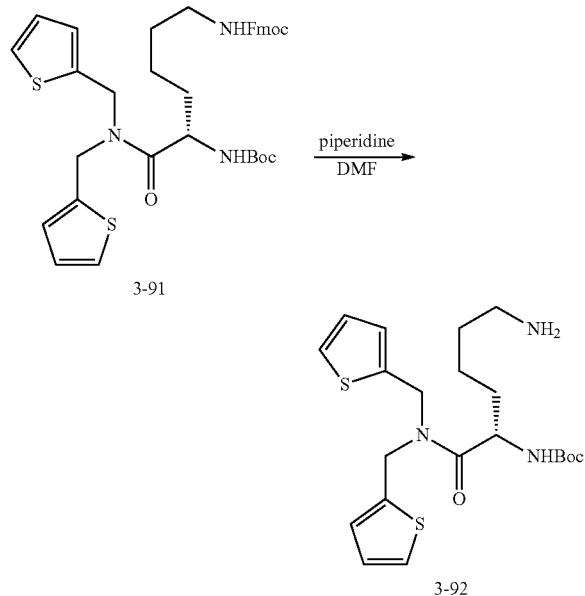

To a solution of 3-91 (382 mg, 0.58 mmol) in N,N-dimethylformamide (6 mL) at room temperature, piperidine (1.0 mL) was added. The reaction was stirred for 2 hours, additional piperidine (1.0 mL) was added. The reaction was stirred overnight, diluted with water, and the precipitate was filtered, washing with water. The filtrate was extracted with ethyl acetate (twice). The organic phases were combined, washed with water (several times) and brine, dried over magnesium sulfate, filtered, and concentrated under reduced pressure to give the title compound 3-92 as a slightly yellow oil (194 mg).

In an alternate preparation, a mixture of 3-90 (500 mg, 0.94 mmol) and anhydrous potassium carbonate (518 mg, 3.75 mmol) in methanol (5 mL) was heated to reflux overnight, and concentrated under reduced pressure. The residue was diluted with water and extracted with dichloromethane (3 times). The organic phases were combined, washed with water and brine, dried over magnesium sulfate, filtered, and concentrated under reduced pressure to give the title compound 3-92 as a slightly yellow oil (291 mg).

Example 31

Preparation of tert-butyl{(2S)-1-[bis(2-thienylmethyl)amino]-1-oxo-6-[(2-thienylacetyl)amino]hexan-2-yl}carbamate (3-98)

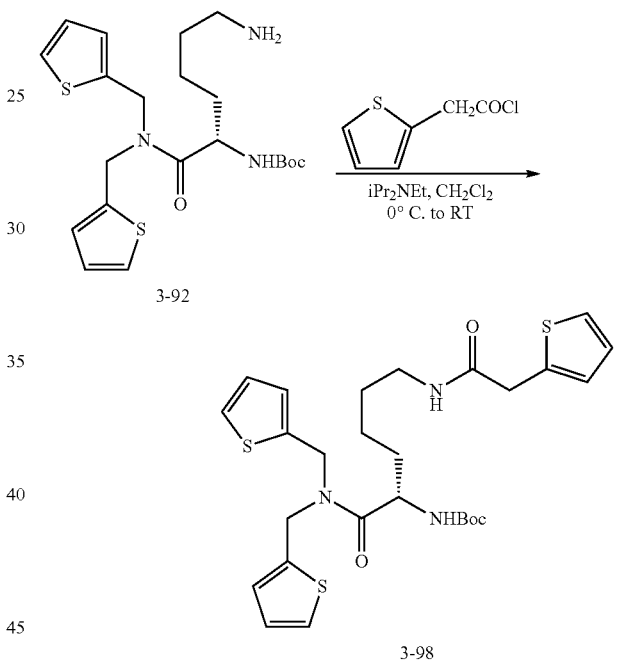

To a solution of 3-92 (40 mg, 0.091 mmol) and N,N-diisopropylethylamine (0.035 mL, 0.2 mmol) in dichloromethane (0.3 mL), 2-thiopheneacetyl chloride (0.012 mL, 0.1 mmol) was added dropwise. The reaction was stirred at 0° C. for 15 minutes, the ice bath was removed, and the mixture was stirred at room temperature overnight. The resulting mixture was diluted with water and extracted twice with ethyl acetate. The organic layers were combined, washed with water, saturated aqueous sodium bicarbonate, and brine, dried, and concentrated under reduced pressure. The residue was purified by automated column chromatography (Biotage®) on silica gel, eluting with hexanes:ethyl acetate to give the title compound 3-98 as a tan solid (34 mg).

Dichloroethane could be used interchangeably with dichloromethane. This procedure was also used to prepare: benzyl{(5S)-5-(benzoylamino)-6-[bis(2-thienylmethyl)amino]-6-oxohexyl}carbamate (3-74) from 3-66.HCl and benzoyl chloride in dichloroethane; 6-[(2-thienylacetyl)

amino]-N,N-bis(2-thienylmethyl)hexanamide (3-112) from 3-103 and 2-thiopheneacetyl chloride; benzyl[(5S)-6-[bis(2-thienylmethyl)amino]-5-(butyrylamino)-6-oxohexyl]carbamate (3-124) from 3-66.HCl and n-butyryl chloride in dichloroethane; N,N-bis(2-thienylmethyl)benzamide (4-2) from 1-1 and benzoyl chloride; methyl(2S)-6-{[(benzyloxy)carbonyl]amino}-2-[(2-thienylacetyl)(2-thienylmethyl)amino]hexanoate (5-6) from 5-5 and 2-thiopheneacetyl chloride; methyl(2S)-6-{[(benzyloxy)carbonyl]amino}-2-[(2-thienylcarbonyl)(2-thienylmethyl)amino]hexanoate (5-9) from 5-5 and 2-thiophenecarbonyl chloride; benzyl {(5S)-5-[(tert-butoxycarbonyl)amino]-6-[(2-thienylacetyl)(2-thienylmethyl)amino]hexyl}carbamate (5-14) from 5-11 and 2-thiopheneacetyl chloride; benzyl{(5S)-5-[(tert-butoxycarbonyl)amino]-6-[(2-thienylcarbonyl)(2-thienylmethyl)amino]hexyl}carbamate (5-16) from 5-11 and 2-thiophenecarbonyl chloride; benzyl{(5S)-5-[(tert-butoxycarbonyl)amino]-6-[(4-methoxybenzoyl)(2-thienylmethyl)amino]hexyl}carbamate (5-18) from 5-11 and 4-methoxybenzoyl chloride; 2-bromo-N,N-bis(2-thienylmethyl)acetamide (1-37) from 1-1 and bromoacetyl chloride; N-{6-[bis(4-methoxybenzyl)amino]-6-oxohexyl}-4-methoxybenzamide (3-136) from 3-135 and 4-methoxybenzoyl chloride; N-{6-[bis(4-methoxybenzyl)amino]-6-oxohexyl}-4-methoxy-N-(4-methoxybenzyl)benzamide (3-138) from 3-137 and 4-methoxybenzoyl chloride; tert-butyl{5-[(2-thienylcarbonyl)(2-thienylmethyl)amino] pentyl}carbamate (5-35) from 5-34 and 2-thiophenecarbonyl chloride; N-{2-[bis(2-thienylmethyl)sulfamoyl]ethyl}-N-(2-thienylmethyl)thiophene-2-carboxamide (7-3) from 7-1 and 2-thiophenecarbonyl chloride; N-{2-[bis(2-thienylmethyl)sulfamoyl]ethyl}-2-(2-thienyl)acetamide (7-16) from 7-13 and 2-thiopheneacetyl chloride; N-{2-[bis(2-thienylmethyl)sulfamoyl]ethyl}thiophene-2-carboxamide (7-17) from 7-13 and 2-thiophenecarbonyl chloride; methyl (acetyl{2-[bis(2-thienylmethyl)sulfamoyl]ethyl}amino)acetate (7-38) from 7-19 and acetyl chloride; and methyl (acetyl {2-[bis(4-methoxybenzyl)sulfamoyl]ethyl}amino) acetate (7-42) from 7-41 and acetyl chloride.

In another variation, a symmetrical diamine/diamine dihydrochloride was used in place of the amine, using 2.2 equivalents of the acid chloride and excess N,N-diisopropylethylamine in dichloromethane to give symmetrical diamides. The following compounds were prepared by this variation: N,N'-heptane-1,7-diylbis[N-(2-thienylmethyl)thiophene-2-carboxamide](5-20) from 5-19 and 2-thiophenecarbonyl chloride; N,N'-heptane-1,7-diylbis[N-(2-thienylmethyl)benzamide](5-21) from benzoyl chloride; N,N'-hexane-1,6-diylbis[N-(2-thienylmethyl)thiophene-2-carboxamide](5-26) from 5-25 and 2-thiophenecarbonyl chloride; N,N'-hexane-1,6-diylbis[N-(3-methoxybenzyl)thiophene-2-carboxamide](5-28) from 5-27 and 2-thiophenecarbonyl chloride; and N,N'-pentane-1,5-diyldithiophene-2-carboxamide (5-36) from cadaverine and 2-thiophenecarbonyl chloride.

In yet another variation, a symmetrical diacid chloride was used in place of the acid chloride, reacting with 2 equivalents of the amine hydrochloride and 6 equivalents of N,N-diisopropylethylamine. This variation of the procedure was used to prepare: N,N,N',N'-tetrakis(2-thienylmethyl) hexanediamide (6-9) from adipoyl chloride and 1-1; N,N,N',N'-tetrakis(3-methoxybenzyl)hexanediamide (6-10) from adipoyl chloride and 1-3; N,N,N',N'tetrakis(4-methoxybenzyl)hexanediamide (6-11) from adipoyl chloride and 1-6; (3E)-N,N,N',N'-tetrakis(2-thienylmethyl)hex-3-enediamide (6-14) from 6-13 and 1-1; N,N,N',N'-tetrakis(2-thienylmethyl)pentanediamide (6-15) from glutaryl chloride and 1-1; N,N,N',N'-tetrakis(4-methoxybenzyl)pentanediamide (6-16) from glutaryl chloride and 1-6; 2,2'-oxybis[N,N-bis(2-thienylmethyl)acetamide](6-17) from diglycolyl dichloride and 1-1; N,N,N',N'-tetrakis(2-thienylmethyl)octanediamide (6-18) from suberoyl chloride and 1-1; N,N,N',N'-tetrakis(2-thienylmethyl)heptanediamide (6-19) from pimeloyl chloride and 1-1; 2,2'-(1,3-phenylene)bis[N,N-bis(2-thienylmethyl)acetamide](6-22) from 6-21 and 1-1; N,N,N',N'-tetrakis(4-methoxybenzyl)heptanediamide (6-23) from pimeloyl chloride and 1-6; N,N,N',N'-tetrakis(4-methoxybenzyl)succinamide (6-24) from succinyl chloride and 1-6; N,N,N',N'-tetrakis(4-methoxybenzyl)octanediamide (6-26) from suberoyl chloride and 1-6; and N,N'-bis(4-methoxybenzyl)-N,N'-bis(2-thienylmethyl)hexanediamide (6-32) from adipoyl chloride and 1-42.

Example 32

Preparation of N,N-bis(2-thienylmethyl)-6-[(2-thienylmethyl)amino]hexanamide (3-105)

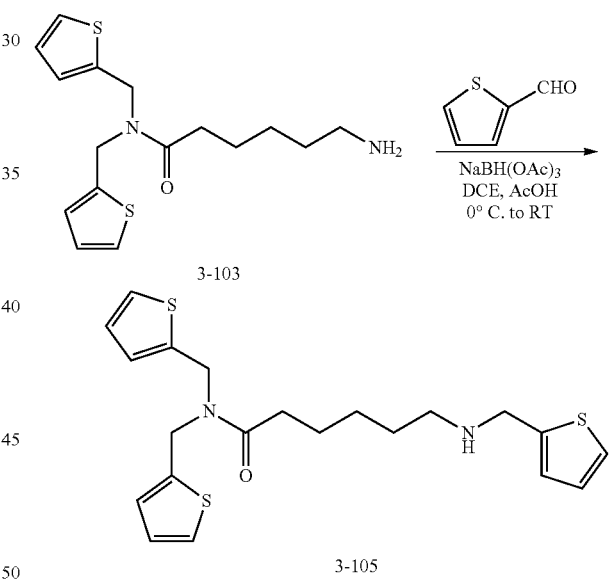

To a solution of 3-103 (170 mg, 0.53 mmol) and 2-thiophenecarboxaldehyde (0.044 mL, 0.48 mmol) in dichloroethane (2.7 mL) and acetic acid (0.18 mL, 3.2 mmol) at 0° C., sodium triacetoxyborohydride (337 mg, 1.6 mmol) was added. The ice bath was removed and the mixture was stirred overnight at room temperature. The reaction was diluted with saturated aqueous sodium bicarbonate and extracted with ethyl acetate (3 times). The organic phases were combined, washed successively with water and brine (twice), dried over magnesium sulfate, filtered, and concentrated under reduced pressure to give the title product 3-105 as a yellow oil (130 mg).

This procedure was also used to prepare N,N-bis(4-methoxybenzyl)-6-[(4-methoxybenzyl)amino]hexanamide (3-137) from 3-135 and p-anisaldehyde.

Example 33

Preparation of N-benzyl-N-{6-[bis(2-thienylmethyl)amino]-6-oxohexyl}thiophene-2-carboxamide (3-108)

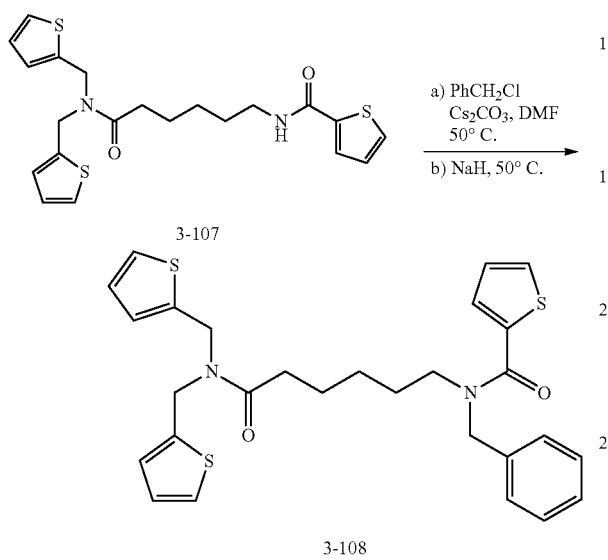

To a solution of 3-107 (50 mg, 0.12 mmol) in N,N-dimethylformamide (1 mL) at room temperature, cesium carbonate (113 mg, 0.35 mmol) was added. The mixture was stirred for one hour, benzyl chloride (0.015 mL, 0.13 mmol) was added and the reaction was heated to 50° C. overnight. Sodium hydride (60% dispersion in mineral oil, 5.2 mg, 0.13 mmol) was added and the reaction was heated to 50° C. overnight. The mixture was diluted with water, and extracted with ethyl acetate (twice). The organic phases were combined, washed successively with saturated aqueous sodium bicarbonate and brine, dried over magnesium sulfate, filtered, and concentrated under reduced pressure. The crude residue was purified by chromatography on silica gel eluting with hexanes:ethyl acetate to give the title compound 3-108 as a yellow oil (46 mg).

Example 34

Preparation of methyl(3R)-3-(1,3-benzodioxol-5-yl)-3-[({(2S)-1-[bis(2-thienylmethyl)amino]-1-oxohexan-2-yl}carbamoyl)amino]propanoate (3-122)

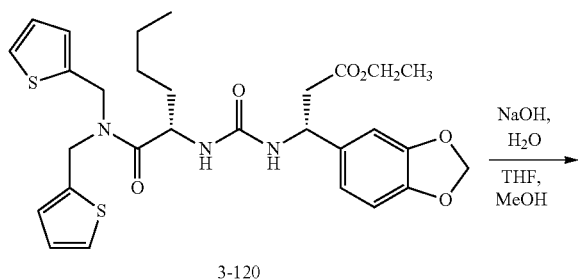

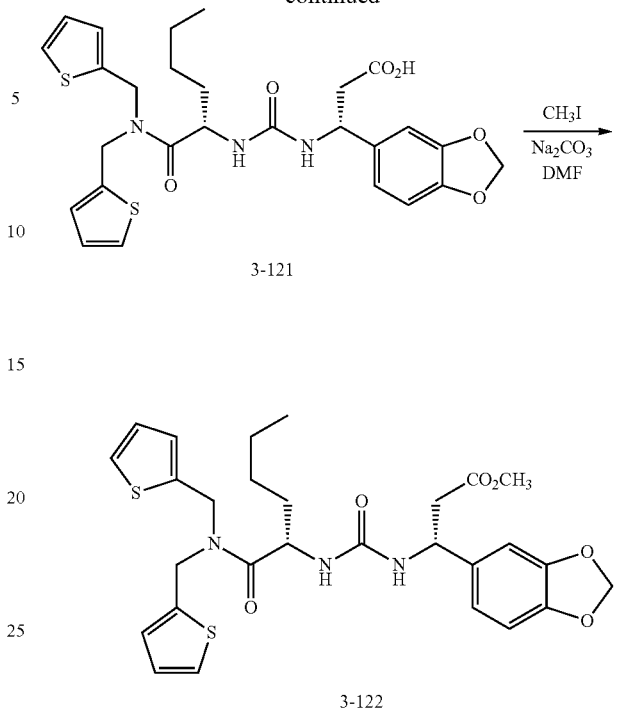

I. (3R)-3-(1,3-Benzodioxol-5-yl)-3-[({(2S)-1-[bis(2-thienylmethyl)amino]-1-oxohexan-2-yl}carbamoyl)amino]propanoic acid (3-121)

To a solution of 3-120 (85 mg, 0.14 mmol) in tetrahydrofuran (1.3 mL) aqueous sodium hydroxide (2N, 0.9 mL, 1.8 mmol) and methanol (0.4 mL) were added. The reaction was stirred 15 minutes, diluted with water, acidified with potassium hydrogen sulfate (1M), and extracted with ethyl acetate (twice). The organic layers were combined, washed with saturated brine, dried over magnesium sulfate, filtered, and concentrated under reduced pressure to give the title compound as a milky off-white syrup (69 mg).

This procedure was also used to prepare: (3R)-3-(1,3-benzodioxol-5-yl)-3-[({(2R)-1-[bis(2-thienylmethyl)amino]-1-oxohexan-2-yl}carbamoyl)amino]propanoic acid (3-127) from 3-126; and 4-[(tert-butoxycarbonyl)amino]butanoic acid (3-144) from 3-143; 4-(1,1-dioxido-1,2-thiazolidin-2-yl)butanoic acid (3-162) from 3-161; (5S)-6-[bis(2-thienylmethyl)amino]-5-[(tert-butoxycarbonyl)amino]-6-oxohexanoic acid (6-33) from 3-43; (acetyl{2-[bis(2-thienylmethyl)sulfamoyl]ethyl}amino)acetic acid (7-39) from 7-38; and (acetyl{2-[bis(4-methoxybenzyl)sulfamoyl]ethyl}amino)acetic acid (7-43) from 7-42.

Alternately, the workup was modified to allow for the isolation of aminoacids. Upon completion of hydrolysis of an aminoester, the reaction mixture was acidified with hydrochloric acid (2 N). Saturated aqueous sodium bicarbonate was added to the solution until it became cloudy. The precipitate was collected by filtration and additional sodium bicarbonate was added to the filtrate to precipitate more product, which was collected. The solids were combined and dried under vacuum. This modification was used to prepare: ({2-[bis(2-thienylmethyl)sulfamoyl]ethyl}amino)acetic acid (7-20) from 7-19; and 3-({2-[bis(2-thienylmethyl)sulfamoyl]ethyl}amino)propanoic acid (7-27) from 7-26.

II. Methyl(3R)-3-(1,3-benzodioxol-5-yl)-3-[({(2S)-1-[bis(2-thienylmethyl)amino]-1-oxohexan-2-yl}carbamoyl)amino]propanoate (3-122)

To a solution of 3-121 (69 mg, 0.12 mmol) in N,N-dimethylformamide (0.5 mL) at room temperature under a dry nitrogen atmosphere, sodium carbonate (30 mg, 0.28 mmol) and iodomethane (0.010 mL, 0.16 mmol) were added. The reaction was stirred 1 day and additional N,N-dimethylformamide (0.5 mL) and iodomethane (0.030 mL, 0.48 mmol) were added. The reaction was stirred for 5 days and additional iodomethane (0.020 mL, 0.32 mmol) was added. The reaction was stirred overnight, diluted with water and extracted with ethyl acetate:hexanes (1:1, four times). The organic layers were combined, washed with water (3 times) and saturated brine (twice), dried over magnesium sulfate, filtered, and concentrated under reduced pressure. The residue was purified by column chromatography on silica gel, eluting with hexanes:ethyl acetate (7:3 to 13:7) to give the title compound as a 3-122 as a light tan solid (56 mg).

This procedure was also used to prepare methyl(3R)-3-(1,3-benzodioxol-5-yl)-3-[({(2R)-1-[bis(2-thienylmethyl)amino]-1-oxohexan-2-yl}carbamoyl)amino]propanoate (3-129) from 3-128.

Example 35

Preparation of sodium (3R)-3-(1,3-benzodioxol-5-yl)-3-[({(2R)-1-[bis(2-thienylmethyl)amino]-1-oxohexan-2-yl}carbamoyl)amino]propanoate (3-128)

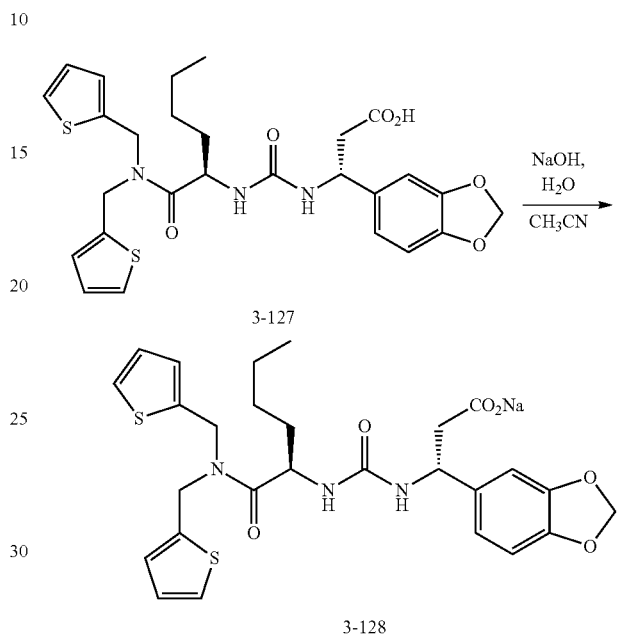

A solution of 3-127 (1.68 g, 3.01 mmol) in acetonitrile (30 mL) and aqueous sodium hydroxide (0.1000 N, 30.7 mL) was swirled, filtered and diluted with water (100 mL). The cloudy solution was frozen at −78° C. and lyophilized under reduced pressure to give the title compound as a 3-128 as an off-white solid (1.73 g).

Example 36

Preparation of 6-(1,1-dioxido-1,2-thiazolidin-2-yl)-N,N-bis(4-methoxybenzyl)hexanamide (3-151)

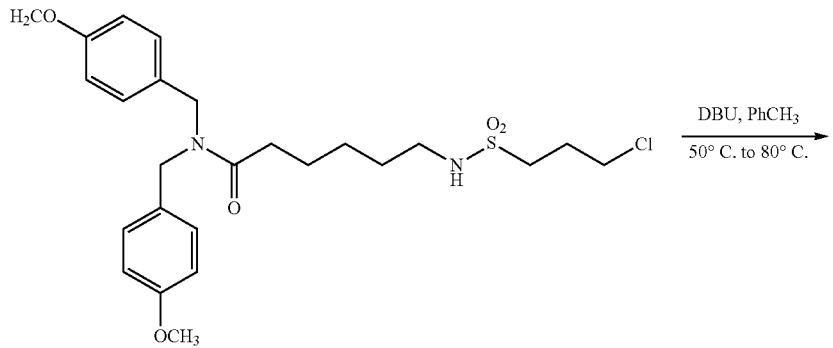

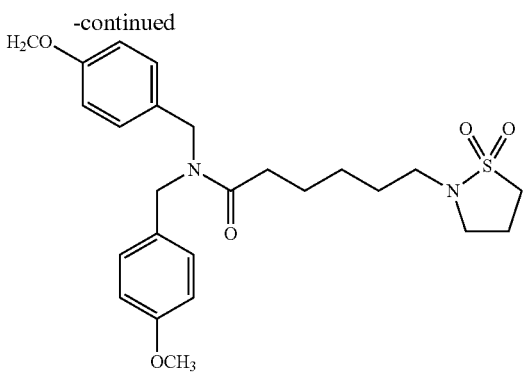

3-151

To a solution of 3-150 (85 mg, 0.17 mmol) in toluene (1.7 mL), 1,8-diazabicyclo[5.4.0]undec-7-ene (0.03 mL, 0.18 mmol was added. The mixture was heated to 50° C. for four hours, and then to 80° C. overnight. The reaction mixture was diluted with ethyl acetate and washed with aqueous HCl (0.5 N), water and brine. The organic layer was dried over magnesium sulfate, filtered and concentrated under reduced pressure. The residue was purified by automated column chromatography (Biotage®) on silica gel, eluting with hexanes:ethyl acetate to give the title compound 3-151 as clear oil (42 mg).

Example 37

Preparation of benzyl{(5S)-6-[bis(2-thienylmethyl)amino]-5-cyano-6-oxohexyl}carbamate (3-167)

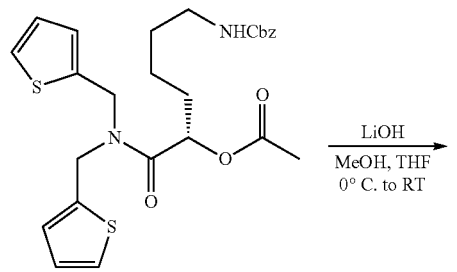

3-87

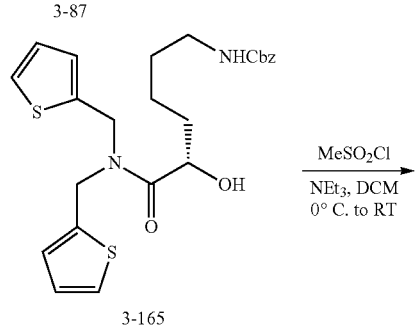

3-165

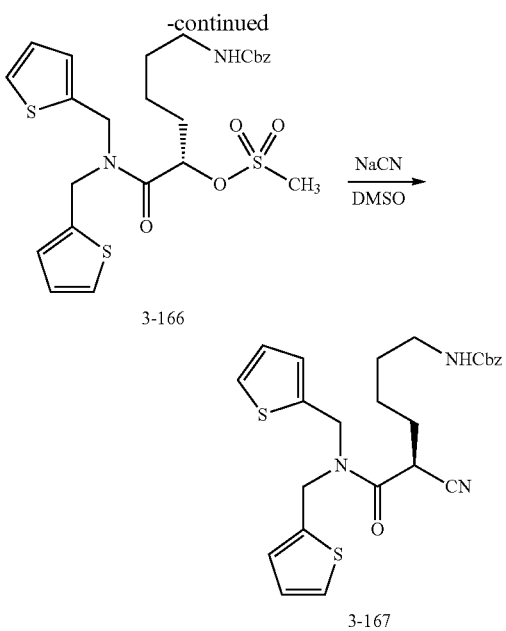

3-166

3-167

I. Benzyl{(5S)-6-[bis(2-thienylmethyl)amino]-5-hydroxy-6-oxohexyl}carbamate (3-165)

To a solution of 3-87 (446 mg, 0.87 mmol) in tetrahydrofuran (5 mL) at 0° C., lithium hydroxide (27 mg, 1.1 mmol) and methanol (2 mL) were added. The mixture was allowed to warm to room temperature and stirred overnight. The reaction mixture was diluted with dichloromethane and washed with saturated aqueous sodium bicarbonate and brine. The organic layer was dried over sodium sulfate, filtered and concentrated under reduced pressure to give the title compound 3-165 as cloudy off-white syrup (352 mg).

II. (2S)-6-{[(Benzyloxy)carbonyl]amino}-1-[bis(2-thienylmethyl)amino]-1-oxohexan-2-yl methanesulfonate (3-166)

To a solution of 3-165 (160 mg, 0.338 mmol) in dichloromethane (1.5 mL) and triethylamine (0.25 mL, 1.8 mmol)

cooled to 0° C., methanesulfonyl chloride (0.060 mL, 0.77 mmol) was added. The mixture was allowed to warm to room temperature, stirred overnight, and diluted with hexanes:ethyl acetate (1:1) and water. The organic layer was washed with saturated sodium bicarbonate (twice), water and brine, dried over magnesium sulfate, filtered and concentrated to give the title compound 3-166 as a light yellow syrup (140 mg).

III. Benzyl{(5S)-6-[bis(2-thienylmethyl)amino]-5-cyano-6-oxohexyl}carbamate (3-167)

A mixture of 3-166 (21 mg, 0.038 mmol) and sodium cyanide (3.8 mg, 0.078 mmol) in anhydrous dimethylsulfoxide (0.2 mL) was stirred at room temperature overnight. The mixture was diluted with water and extracted with ethyl acetate (three times). The combined organic layers were washed with water (twice) and brine, dried over magnesium sulfate, filtered and concentrated. The residue was purified by automated column chromatography (Biotage®) on silica gel, eluting with hexanes:ethyl acetate (3:1 to 3:2 with 1% methanol) to give the title compound 3-167 as a yellow syrup (10 mg). Alternately, other nucleophiles could be used in place of sodium cyanide and dimethylformamide as solvent. This variation was used to prepare: benzyl{(5R)-5-azido-6-[bis(2-thienylmethyl)amino]-6-oxohexyl}carbamate (3-168) from 3-166 and sodium azide; and S-{(2R)-6-{[(benzyloxy)carbonyl]amino}-1-[bis(2-thienylmethyl)amino]-1-oxohexan-2-yl}ethanethioate (3-169) from 3-166 and potassium thioacetate.

Example 38

Preparation of 4-azidobenzyl{(5S)-6-[bis(2-thienylmethyl)amino]-5-[(tert-butoxycarbonyl)amino]-6-oxohexyl}carbamate (3-171)

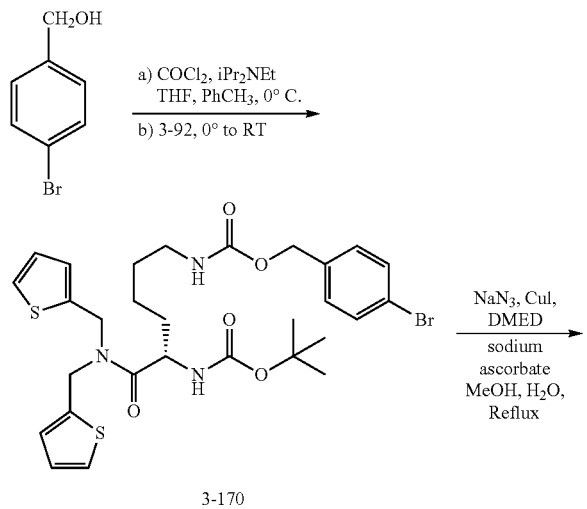

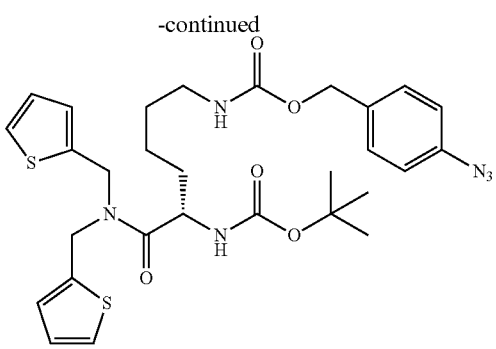

3-171

I. tert-Butyl[(2S)-1-[bis(2-thienylmethyl)amino]-6-({[(4-bromobenzyl)oxy]carbonyl}amino)-1-oxohexan-2-yl]carbamate (3-170)

To a solution of phosgene (20% in toluene, 1.0 mL, 1.89 mmol) in tetrahydrofuran (2 mL) at 0° C. under nitrogen, a solution of 4-bromobenzyl alcohol (301 mg, 1.61 mmol) and N,N-diisopropylethylamine (1.1 mL, 6.32 mmol) in tetrahydrofuran (1.5 mL) was added dropwise. The mixture was stirred at 0° C. for 30 minutes, then at room temperature for 75 minutes. To the resulting mixture, a solution of 3-92 (400 mg, 0.91 mmol) in tetrahydrofuran (2 mL) was added dropwise. The mixture was stirred overnight, then was diluted with hexanes:ethyl acetate (1:1) and washed with water, HCl (1 N), saturated aqueous sodium bicarbonate, water and brine. The organic layer was dried over sodium sulfate, filtered and concentrated under reduced pressure. The residue was purified by automated column chromatography (Biotage®) on silica gel, eluting with a hexanes:ethyl acetate gradient (4:1 to 1:3) to give the title compound 3-170 as an off-white solid (305 mg).

II. 4-Azidobenzyl{(5S)-6-[bis(2-thienylmethyl)amino]-5-[(tert-butoxycarbonyl)amino]-6-oxohexyl}carbamate (3-171)

To a suspension of copper(I) iodide (7.7 mg, 0.040 mmol) in 1:1 methanol:water (2 mL, sparged with N2 before use), N,N'-dimethylethylene diamine (DMED, 7.4 mg, 0.084 mmol), sodium ascorbate (2.2 mg, 0.011 mmol), and sodium azide (9.0 mg, 0.14 mmol) were added sequentially. The mixture was stirred at room temperature for 10 minutes then added to a solution of 3-170 (77 mg, 0.12 mmol) in 1:1 methanol:water (1 mL, sparged with N2 before use) under a dry nitrogen atmosphere. The mixture was heated to 80° C. for 6 hours, then cooled to room temperature, diluted with brine, and extracted with ethyl acetate. The organic layer was washed with brine, water, and brine, dried over sodium sulfate, filtered, and concentrated under reduced pressure. The residue was purified by automated silica gel chromatography (Biotage®), eluting with a hexanes:ethyl acetate gradient to give the title compound 3-171 as a colorless solid (60 mg).

This procedure was also used to prepare: tert-butyl[(2S)-1-[(4-azidobenzyl)(2-thienylmethyl)amino]-6-{[(benzyloxy)carbonyl]amino}-1-oxohexan-2-yl]carbamate (3-173) from 3-172; methyl(6S,10S)-2-(4-azidoobenzyl)-10-(1,3-benzodioxol-5-yl)-6-butyl-3,8-dioxo-1-(2-thienyl)-4-oxa-2,7,9-triazadodecan-12-oate (2-87) from 2-86; and (2S)-2-

{[(4-azidobenzyl)carbamoyl]amino}hexyl bis(2-thienylmethyl)carbamate (2-112) from 2-111.

Example 39

Preparation of N,N-bis(2-thienylmethyl)acetamide (4-1)

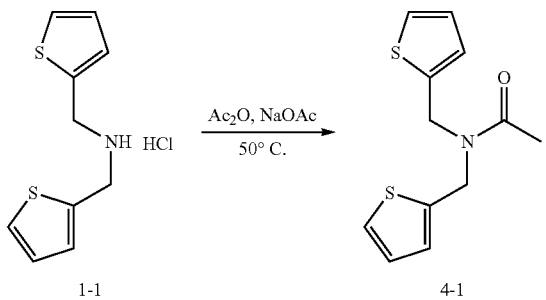 [SMILES: c1csc(CNCc2cccs2)c1 ; Cl ; CC(=O)N(Cc1cccs1)Cc1cccs1]

To a suspension of 1-1 (100 mg, 0.410 mmol) in acetic anhydride (2.0 mL), sodium acetate (0.5 g, 3.7 mmol) was added. The resulting mixture was stirred at 50° C. overnight, diluted with dichloromethane and saturated aqueous sodium bicarbonate, and stirred until all gas evolution had ceased. The aqueous layer was extracted with dichloromethane (twice). The organic layers were combined, dried over sodium sulfate, decanted, filtered through silica gel and concentrated to give the title compound 4-1 as an oil (73 mg).

Example 40

Preparation of 2-(morpholin-4-yl)-N,N-bis(2-thienylmethyl)ethanesulfonamide (4-49)

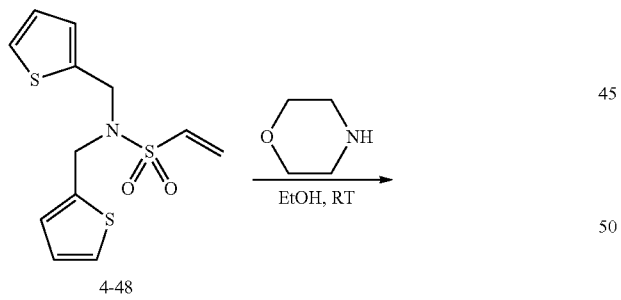

To a solution of 4-48 (100 mg, 0.33 mmol) in ethanol (3 mL), morpholine (0.29 mL, 3.3 mmol) was added. The mixture was stirred at room temperature overnight and was diluted with aqueous HCl (0.5 N) and extracted with ethyl acetate (twice). The organic layers were combined, washed with water, saturated aqueous sodium bicarbonate and brine, dried over magnesium sulfate, filtered and concentrated under reduced pressure. The residue was purified by chromatography on silica gel, eluting with hexanes:ethyl acetate to give the title compound 4-49 as an amber oil (23 mg).

This procedure was also used to prepare: N,N-bis(2-thienylmethyl)-2-[(2-thienylmethyl)amino]ethanesulfonamide (7-1) from 4-48 and 2-thiophenemethylamine; and N,N-bis(4-methoxybenzyl)-6-({[2-(morpholin-4-yl)ethyl]sulfonyl}amino)hexanamide (3-152) from 3-149 and morpholine.

Alternately, triethylamine (6.5 to 10 equivalents) could be added to the reaction. In some cases heating was required. This variation was used to prepare: 2-(butylamino)-N,N-bis(2-thienylmethyl)ethanesulfonamide (7-4) from 4-48 and n-butylamine; 2-amino-N,N-bis(2-thienylmethyl)ethanesulfonamide (7-13) from 4-48 and ammonia (2M in ethanol); 2-(methylamino)-N,N-bis(2-thienylmethyl)ethanesulfonamide (7-23) from 4-48 and methylamine (2.0 M in tetrahydrofuran); 3-({2-[bis(4-methoxybenzyl)sulfamoyethyl]ethyl}amino)-N,N-bis(2-thienylmethyl)propanamide (7-31) from 7-30 and 3-5 at 50° C.; 3-[{2-[bis(2-thienylmethyl)sulfamoyl]ethyl}(methyl)amino]-N,N-bis(2-thienylmethyl)propanamide (7-34) from 4-48 and 7-33 at 50° C.; 3-[{2-[bis(4-methoxybenzyl)sulfamoyl]ethyl}(methyl)amino]-N,N-bis(2-thienylmethyl)propanamide (7-35) from 7-30 and 7-33 at 50° C.; (2S)-2-({2-[bis(2-thienylmethyl)sulfamoyl]ethyl}amino)-N,N-bis(2-thienylmethyl)hexanamide (7-36) from 4-48 and 3-13 at 50° C.; and (2S)-2-({2-[bis(4-methoxybenzyl)sulfamoyl]ethyl}amino)-N,N-bis(2-thienylmethyl)hexanamide (7-37) from 7-30 and 3-13. This variation was also used when an amine hydrochloride was used as the nucleophile source. This modification was used to prepare: methyl({2-[bis(2-thienylmethyl)sulfamoyl]ethyl}amino)acetate (7-19) from 4-48 and glycine methyl ester hydrochloride at 90° C.; methyl 3-({2-[bis(2-thienylmethyl)sulfamoyl]ethyl}amino)propanoate (7-26) from 4-48 and -alanine methyl ester hydrochloride at 70° C. (some trans esterification occurred); and methyl({2-[bis(4-methoxybenzyl)sulfamoyl]ethyl}amino)acetate (7-41) from 7-30 and glycine methyl ester hydrochloride at 70° C. (reaction done in methanol).

Example 41

Preparation of methyl(2S)-6-{[(benzyloxy)carbonyl]amino}-2-[(2-thienylmethyl)amino]hexanoate (5-5)

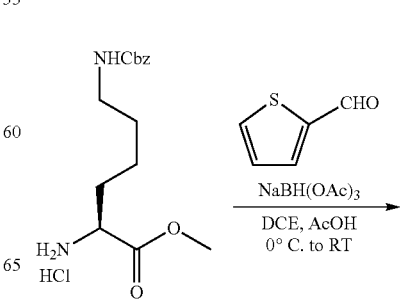

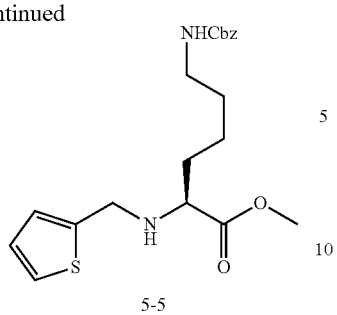

5-5

To a stirred solution of H-Lys(Z)—OMe.HCl (500 mg, 1.51 mmol) and 2-thiophenecarboxaldehyde (186 mg, 1.7 mmol) in dichloroethane (5 mL) and acetic acid (0.26 mL, 4.53 mmol) at 0° C., sodium triacetoxyborohydride (640 mg, 3.02 mmol) was added. The ice bath was removed and the reaction was stirred overnight at room temperature. The reaction was diluted with saturated aqueous sodium bicarbonate and extracted with ethyl acetate (three times). The organic phases were combined, washed successively with water and brine twice, dried over magnesium sulfate, filtered, and concentrated under reduced pressure. The residue was purified by chromatography on silica gel eluting with hexanes:ethyl acetate (9:1 to 1:1). The title product 5-5 was isolated as a clear oil (364 mg).

Alternately, a free amine can be used in place of the amine hydrochloride. This variation was used to prepare benzyl {(5S)-5-[(tert-butoxycarbonyl)amino]-6-[(2-thienylmethyl) amino]hexyl}carbamate (5-11) from 5-10 and 2-thiophenemethylamine.

Example 42

Preparation of benzyl{(5S)-5-[(tert-butoxycarbonyl) amino]-6-oxohexyl}carbamate (5-10)

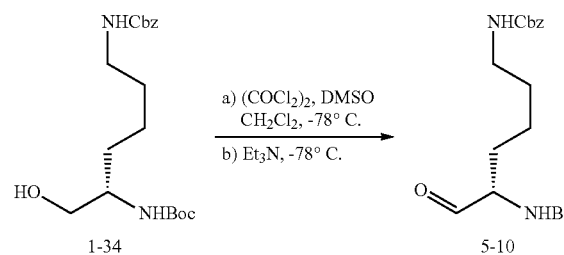

To a solution of oxalyl chloride (0.57 mL, 5.97 mmol) in dichloromethane (30 mL) at −78° C. under a nitrogen atmosphere, dimethylsulfoxide (0.85 mL) was added dropwise. After stirring for 10 minutes, the reaction was transferred using a cannula to a solution of 1-34 in dichloromethane (30 mL) at −78° C. under a nitrogen gas atmosphere. This solution was stirred at −78° C. for 30 minutes, triethylamine (1.7 mL, 11.9 mmol)) was added and the dry ice/acetone bath was removed. The reaction was stirred for 30 minutes while warming to room temperature, and diluted with dichloromethane and water. The aqueous layer was extracted with ethyl acetate twice. The organic phases were combined, washed successively with aqueous hydrochloric acid (0.5 N), saturated aqueous sodium bicarbonate and brine, dried over magnesium sulfate, filtered, and concentrated under reduced pressure to give the title compound 5-10 as an oil (1.38 g).

Example 43

Preparation of 5-[Bis(2-thienylmethyl)amino]-5-oxopentanoic acid (6-1)

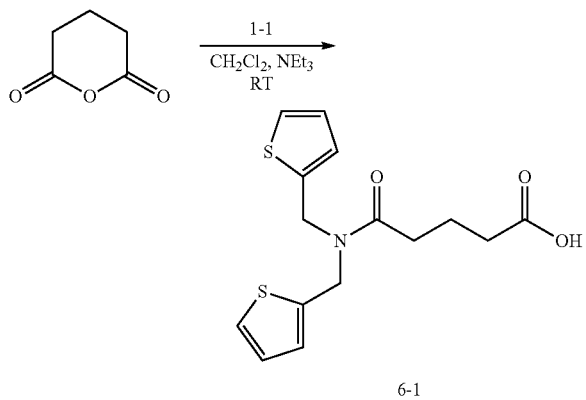

To a solution of glutaric anhydride (374 mg, 3.28 mmol) in dichloromethane (10 mL) and triethylamine (0.750 mL), 1-1 (811 mg, 3.28 mmol) was added. The reaction mixture was stirred at room temperature overnight, diluted with diethyl ether, and washed with dilute aqueous sodium bicarbonate (2 times). The combined aqueous layers were made acidic with aqueous HCl (2N), and extracted with diethyl ether. The diethyl ether extract of the acidic aqueous mixture was dried over sodium sulfate, filtered and concentrated under reduced pressure to give the title compound 6-1 as a clear oil (1.00 g).

Example 44

Preparation of (3E)-Hex-3-enedioyl dichloride (6-13)

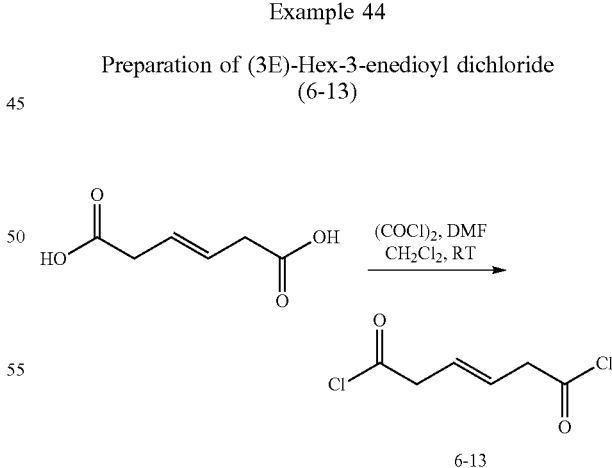

To a solution of trans-hydromuconic acid (186 mg, 1.29 mmol) in dichloromethane (6 mL) at room temperature, N,N-dimethylformamide (4-5 drops) and oxalyl chloride (0.275 mL neat, 3.2 mmol, dissolved in dichloromethane) were added sequentially. The mixture was stirred overnight and concentrated to dryness under reduced pressure. The residue was dissolved in dichloromethane (6 ml) to produce a stock solution which was used in subsequent reactions. This procedure was also used to prepare a stock solution of 2,2'-(1,3-phenylene)diacetyl chloride (6-21) from 1,3-phenylenediacetic acid.

Example 45

Preparation of 2-[{2-[bis(2-thienylmethyl)sulfamoyl]ethyl}(methyl)amino]-N,N-bis(2-thienylmethyl)acetamide (7-24)

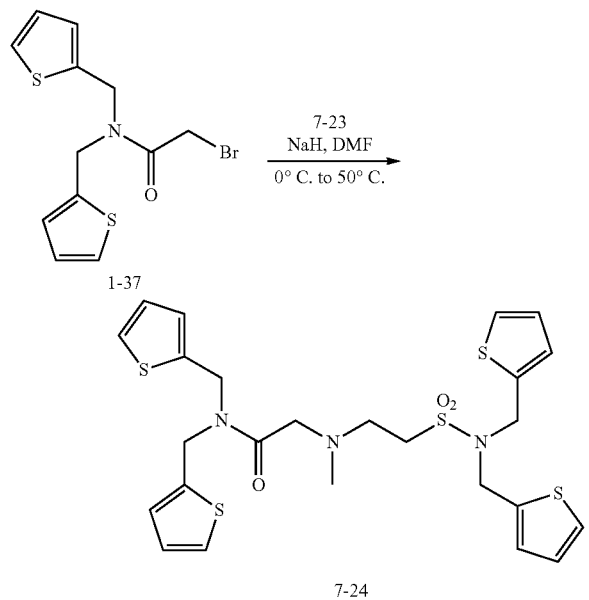

To a solution of 7-23 (155 mg, 0.47 mmol) in N,N-dimethylformamide (2 mL) cooled to 0° C. under a dry nitrogen atmosphere, sodium hydride (60% dispersion in mineral oil, 21 mg, 0.52 mmol) was added. The mixture was stirred for 10 minutes and a solution of 1-37 (172 mg, 0.52 mmol) in N,N-dimethylformamide (1 mL) was added. The resulting mixture was heated to 50° C. overnight, diluted with water, and extracted twice with ethyl acetate. The combined organic layers were washed with HCl (0.5 N), water, saturated aqueous sodium bicarbonate, and brine, dried over magnesium sulfate, filtered and concentrated under reduced pressure. The residue was purified by automated silica gel chromatography (Biotage®), eluting with a hexanes:ethyl acetate gradient to give the title compound 7-24 as a slightly yellow oil (170 mg).

This procedure was also used to prepare: 3-[{2-[bis(2-thienylmethyl)amino]-2-oxoethyl}(butyl)amino]-N,N-bis(2-thienylmethyl)propanamide (7-22) from 3-155 and 1-37; and 2-[{2-[bis(2-thienylmethyl)sulfamoyl]ethyl}(butyl)amino]-N,N-bis(2-thienylmethyl)acetamide (7-25) from 7-4 and 1-37.

Example 46

Adhesion Assays

Assays were performed according to procedures previously described (Vanderslice, P., D. G. Woodside, A. R. Caivano, E. R. Decker, C. L. Munsch, S. J. Sherwood, W. S. Lejeune, Y. J. Miyamoto, B. W. McIntyre, R. G. Tilton, and R. A. Dixon. Potent in vivo suppression of inflammation by selectively targeting the high affinity conformation of integrin alpha4beta1. Biochem Biophys Res Commun 400:619-624.) Assays to evaluate enhanced cell binding mediated by $\iota_1\iota$ v. L. and used K562-1 cells binding to CS1-BSA, K562 cells binding to fibronectin, HUVEC binding to vitronectin, HSB cells binding to ICAM-1, and K562-cells binding to MAdCAM-1, respectively. For each assay, the cells expressed the appropriate integrin receptor either in recombinant form (K562-1, K562-) or endogenously (K562-1, HUVEC-v.HSB). 96-well Pro-Bind plates were coated directly with adhesion substrate (fibronectin, vitronectin, CS1-BSA, VCAM-1, ICAM-1 or MAdCAM-1) at 4° C. overnight. The concentration of substrate protein added to the wells was a sub-optimal dose for cell adhesion (~EC10) as previously determined by dose dependent binding curves. Wells were blocked with 1% BSA at room temperature for 2 hours and then washed with binding buffer prior to the addition of cells. Integrin-expressing cells were labeled with calcein-AM (Molecular Probes) for 30 min at 37° C. HUVEC were trypsinized and resuspended in culture media prior to labeling. Cells were resuspended in binding buffer. Compounds were dissolved in DMSO to make a 100 mM stock solution. Serial dilutions were made in DMSO such that the working compound concentrations were at 100×. Compounds were then diluted 1:100 in binding buffer containing the cells to yield the desired working concentrations and a final DMSO concentration of 1%, and 2×105 cells dispensed into each well. The binding buffer was TBS, pH 7.4 with 1 mM MnCl2 for all assays. Following 30 min incubation at 37° C., the wells were washed with the appropriate binding buffer and the number of cells bound was quantitated on a TECAN Ultra384 or SAFIRE2 fluorescent plate reader. EC50 is defined as the concentration of compound required to achieve 50% of the maximal response.

For the following compounds, which are referred to by their identification numbers in the foregoing Examples, EC50<10 µM: 2-3, 2-5, 2-8, 2-9, 2-11, 2-18, 2-20, 2-21, 2-24, 2-38, 2-52, 2-56, 2-60, 2-62, 2-63, 2-66, 2-67, 2-69, 2-70, 2-72, 2-74, 2-76, 2-80, 2-86, 2-87, 2-89, 2-91, 2-93, 2-95, 2-97, 2-98, 2-100, 2-102, 2-110, 2-111, 2-112, 2-116, 2-118, 2-120, 3-6, 3-15, 3-16, 3-25, 3-26, 3-27, 3-28, 3-31, 3-32, 3-33, 3-36, 3-45, 3-47, 3-48, 3-49, 3-50, 3-52, 3-54, 3-58, 3-61, 3-62, 3-64, 3-65, 3-68, 3-69, 3-70, 3-72, 3-73, 3-74, 3-75, 3-76, 3-77, 3-78, 3-79, 3-80, 3-82, 3-83, 3-85, 3-87, 3-88, 3-90, 3-93, 3-95, 3-96, 3-99, 3-104, 3-106, 3-108, 3-110, 3-111, 3-112, 3-113, 3-115, 3-118, 3-122, 3-129, 3-131, 3-132, 3-133, 3-134, 3-138, 3-139, 3-140, 3-147, 3-150, 3-158, 3-167, 3-168, 3-169, 3-173, 3-175, 3-176, 4-14, 4-15, 4-26, 4-40, 4-43, 4-46, 4-47, 5-2, 5-4, 5-6, 5-9, 5-12, 5-13, 5-14, 5-15, 5-16, 5-17, 5-18, 5-20, 5-21, 5-26, 5-28, 5-30, 5-33, 6-3, 6-5, 6-6, 6-9, 6-10, 6-11, 6-14, 6-15, 6-16, 6-17, 6-18, 6-19, 6-20, 6-22, 6-23, 6-24, 6-25, 6-26, 6-27, 6-28, 6-29, 6-30, 6-32, 6-34, 7-3, 7-6, 7-11, 7-14, 7-15, 7-16, 7-17, 7-18, 7-21, 7-22, 7-24, 7-28, 7-29, 7-31, 7-34, 7-35, 7-36, 7-40, and 7-44.

For the following compounds, 10 µM≤EC50≤30 µM: 2-13, 2-19, 2-22, 2-23, 2-25, 2-26, 2-36, 2-41, 2-46, 2-51, 2-54, 2-78, 2-103, 2-105, 3-1, 3-7, 3-9, 3-10, 3-12, 3-14, 3-19, 3-29, 3-30, 3-34, 3-51, 3-56, 3-59, 3-53, 3-81, 3-94, 3-97, 3-107, 3-109, 3-116, 3-117, 3-136, 3-151, 3-152, 3-153, 3-164, 3-174, 4-4, 4-9, 4-13, 4-25, 4-29, 4-30, 4-35, 5-8, 6-2, 6-7, 6-8, and 7-37.

For the following compounds, EC50>30 µM: 2-27, 2-39, 2-40, 2-42, 2-43, 2-44, 2-45, 2-47, 2-48, 2-49, 2-50, 2-53, 2-82, 2-84, 2-107, 3-3, 3-18, 3-21, 3-22, 3-23, 3-24, 3-37, 3-38, 3-39, 3-40, 3-41, 3-43, 3-55, 3-60, 3-89, 3-100, 3-114, 3-124, 3-125, 3-130, 3-156, 3-163, 3-170, 3-171, 3-172, 4-2, 4-33, 4-42, 4-44, 4-45, 4-49, 5-22, 5-24, 5-32, 6-31, 7-2, 7-7, 7-10, and 7-25.

While many embodiments of the disclosed agonist compounds are synthetic compounds of formula I, in some embodiments an agonist compound is formed by in vivo conversion of a precursor compound to a disclosed compound. For example, a disclosed compound may exist as a stereoisomer wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of some agonist compounds may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Various embodiments of the disclosed agonist compounds may exist in unsolvated or solvated forms, including hydrated forms, such as hemi-hydrates. In general, the solvated forms, with pharmaceutically acceptable solvents such as water and ethanol among others are equivalent to the unsolvated forms for the purposes of this disclosure. Pharmaceutical compositions containing the disclosed agonist compounds are described below.

Pharmaceutical Compositions

The compounds described herein may be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq. The salts may be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

In some embodiments, basic addition salts are prepared in situ during the final isolation and purification of a disclosed compound by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a disclosed agonist compound include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated in some embodiments.

Actual dosage levels of active ingredients in the pharmaceutical compositions may be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used for various therapeutic treatments, a therapeutically effective amount of one or more of the disclosed compounds be employed in pure form or, where such forms exist, in pharmaceutically acceptable salt, ester or pro-drug form. In some cases, the compound is administered as a pharmaceutical composition containing the compound of interest in combination with one or more pharmaceutically acceptable excipients. The phrase "therapeutically effective amount" of a disclosed agonist compound means a sufficient amount of the compound to treat disorders, at a reasonable benefit/risk ratio applicable to any medical treatment. It will be understood, however, that the total daily usage of the disclosed compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the disclosed compounds administered to a human or lower animal may range from about 0.0001 to about 1000 mg/kg/day. For purposes of oral administration, in some embodiments doses are in the range of from about 0.001 to about 5 mg/kg/day. If desired, the effective daily dose can be divided into multiple doses for purposes of administration; consequently, single dose compositions may contain such amounts or submultiples thereof to make up the daily dose.

In some instances, a pharmaceutical composition comprises one or more of the disclosed compounds formulated together with one or more non-toxic pharmaceutically acceptable carriers. The pharmaceutical compositions may be specially formulated for oral administration in solid or liquid form, for parenteral injection or for rectal administration.

A disclosed pharmaceutical compositions may be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion. In some implementations, a pharmaceutical composition comprises a disclosed compound and a physiologically tolerable or acceptable diluent, carrier, adjuvant or vehicle, which are collectively referred to herein as diluents, for parenteral injection, for intranasal delivery, for oral administration in solid or liquid form, for rectal or topical administration, or the like.

In some instances, a composition is delivered through a catheter for local delivery at a target site, via an intracoronary stent (a tubular device composed of a fine wire mesh), or via a biodegradable polymer. In some embodiments, an agonist compound is complexed to a ligand such as an antibody, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Proper fluidity can be maintained, for example, by the use of coating materials such as lecithin, by the maintenance of the required particle size in the case of dispersions and by the use of surfactants.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline foam. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients. Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents. Compositions for rectal or vaginal administration are preferably suppositories which can be prepared by mixing one or more of the disclosed compounds with suitable non-irritating excipients or carriers such as cocoa butter, polyethylene glycol or a suppository wax which are solid at room temperature but liquid at body temperature and therefore melt in the rectum or vaginal cavity and release the active compound.

For some applications, a disclosed compound is administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. In some embodiments, a composition in liposome form contains, in addition to a disclosed agonist compound, stabilizers, preservatives, excipients and the like. The preferred lipids are natural and synthetic phospholipids and phosphatidyl cholines (lecithins) used separately or together. Methods of forming liposomes are known in the art. See, for example, Prescott, Ed., Methods in Cell Biology, Volume XIV, Academic Press, New York, N.Y. (1976), p. 33 et seq.

The term "pharmaceutically acceptable pro-drugs" as used herein represents those pro-drugs of the disclosed compounds which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the disclosed compounds. Pro-drugs according to certain embodiments may be rapidly transformed in vivo to the parent compound of the above formula, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

While the preferred embodiments have been shown and described, modifications thereof can be made by one skilled in the art without departing from the spirit and teachings of the invention. The embodiments described herein are exemplary and representative, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims. All patents, patent applications and publications cited herein are hereby incorporated herein by reference to the extent that they provide materials, methods and explanatory details supplementary to those set forth herein.

What is claimed is:
1. A compound selected from the group consisting of methyl (6S,10S)-10-(1,3-benzodioxol-5-yl)-6-butyl-3, 8-dioxo-1-(2-thienyl)-2-(2-thienylmethyl)-4-oxa-2,7,9-triazadodecan-12-oate; methyl (6S,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl (6S,10S)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; methyl (6S,10S)-10-(1,3-benzodioxol-5-yl)-6-butyl-9-methyl-3,8-dioxo-1-(2-thienyl)-2-(2-thienylmethyl)-4-oxa-2,7,9-triazadodecan-12-oate; ethyl (6S,10R)-10-(1,3-benzodioxol-5-yl)-6-butyl-7-methyl-3,8-dioxo-1-(2-thienyl)-2-(2-thienylmethyl)-4-oxa-2,7,9-triazadodecan-12-oate; methyl (10S)-10-(1,3-benzodioxol-5-yl)-3,8-dioxo-1-(2-thienyl)-2-(2-thienylmethyl)-4-oxa-2,7,9-triazadodecan-12-oate; methyl 3,8-dioxo-1-(2-thienyl)-2-(2-thienylmethyl)-4-oxa-2,7,9-triazadodecan-12-oate; methyl (6S,10S)-10-(1,3-benzodioxol-5-yl)-6-butyl-2-methyl-3,8-dioxo-1-(2-thienyl)-4-oxa-2,7,9-triazadodecan-12-oate; methyl (6S)-6-butyl-3,8-dioxo-1-(2-thienyl)-2-(2-thienylmethyl)-4-oxa-2,7,9-triazadodecan-12-oate; (2S)-2-{[(1,3-benzodioxol-5-ylmethyl)carbamoyl]amino}hexyl bis(2-thienylmethyl)carbamate; methyl (6S,10S)-6-butyl-3,8-dioxo-10-phenyl-1-(2-thienyl)-2-(2-thienylmethyl)-4-oxa-2,7,9-triazadodecan-12-oate; (2S)-2-({[(1S)-1-(1,3-benzodioxol-5-yl)-3-hydroxypropyl]carbamoyl}amino) hexyl bis(2-thienylmethyl)carbamate; (2S)-2-[(benzylcarbamoyl)amino]hexyl bis(2-thienylmethyl) carbamate; (2S)-2-[(morpholin-4-ylcarbonyl)amino]hexyl bis(2-thienylmethyl)carbamate; (2S)-2-{[(3-methoxypropyl)carbamoyl]amino}hexyl bis(2-thienylmethyl)carbamate; (2S)-2-{[(2-methoxyethyl)carbamoyl]amino}hexyl bis(2-thienylmethyl)carbamate; tert-butyl [(2S)-1-{[bis(2-thienylmethyl)carbamoyl]oxy}hexan-2-yl]carbamate; (2S)-2-[(tert-butylcarbamoyl)amino]hexyl bis(2-thienylmethyl) carbamate; (2S)-2-[(isopropylcarbamoyl)amino]hexyl bis(2-thienylmethyl)carbamate; (2S)-2-[(methylcarbamoyl) amino]hexyl bis(2-thienylmethyl)carbamate; tert-butyl [(2R)-1-{[bis(2-thienylmethyl)carbamoyl]oxy}hexan-2-yl] carbamate; benzyl {(5S)-6-{[bis(2-thienylmethyl)carbamoyl]oxy}-5-[(tert-butoxycarbonyl)amino]hexyl}carbamate; methyl (9S,13S)-13-(1,3-benzodioxol-5-yl)-9-({[bis(2-thienylmethyl)carbamoyl]oxy}methyl)-3,11-dioxo-1-phenyl-2-oxa-4,10,12-triazapentadecan-15-oate; (2S)-2-acetamidohexyl bis(2-thienylmethyl)carbamate; methyl (6R,10S)-10-(1,3-benzodioxol-5-yl)-6-butyl-3,8-dioxo-1-(2-thienyl)-2-(2-thienylmethyl)-4-oxa-2,7,9-triazadodecan-12-oate; methyl (6R,10R)-10-(1,3-benzodioxol-5-yl)-6-butyl-3,8-dioxo-1-(2-thienyl)-2-(2-thienylmethyl)-4-oxa-2,7,9-triazadodecan-12-oate; methyl {[bis(2-thienylmethyl)carbamoyl] (methyl)amino}acetate; methyl {[bis(2-thienylmethyl) carbamoyl](butyl)amino}acetate; tert-butyl {[bis(2-thienylmethyl)carbamoyl](butyl)amino}acetate; benzyl {(5S)-6-{[bis(4-methoxybenzyl)carbamoyl]oxy}-5-[(tert-butoxycarbonyl)amino]hexyl}carbamate; tert-butyl [(2S)-1-{[bis(4-methoxybenzyl)carbamoyl]oxy}hexan-2-yl]carbamate; methyl (6S,10S)-10-(1,3-benzodioxol-5-yl)-6-butyl-2-(4-methoxybenzyl)-1-(4-methoxyphenyl)-3,8-dioxo-4-oxa-2,7,9-triazadodecan-12-oate; (2S)-2-({[(1S)-1-(1,3-benzodioxol-5-yl)-3-hydroxypropyl] carbamoyl}amino)hexyl bis(4-methoxybenzyl)carbamate; (2S)-2-[(tert-butoxycarbonyl)amino]hexyl dibenzylcarbamate; methyl (6S,10S)-10-(1,3-benzodioxol-5-yl)-2-benzyl-6- butyl-3,8-dioxo-1-phenyl-4-oxa-2,7,9-triazadodecan-12-oate; tert-butyl [(2S)-1-{[bis(4-methylbenzyl)carbamoyl]oxy}hexan-2-yl]carbamate; methyl (6S,10S)-10-(1,3-benzodioxol-5-yl)-6-butyl-2-(4-methylbenzyl)-1-(4-methylphenyl)-3,8-dioxo-4-oxa-2,7,9-triazadodecan-12-oate; tert-butyl [(2S)-1-{[bis(4-chlorobenzyl)carbamoyl]oxy}hexan-2-yl]carbamate; methyl (6S,10S)-10-(1,3-benzodioxol-5-yl)-6-butyl-2-(4-chlorobenzyl)-1-(4-chlorophenyl)-3,8-dioxo-4-oxa-2,7,9-triazadodecan-12-oate; (2S)-2-[(tert-butoxycarbonyl)amino]hexyl (4-bromobenzyl)(2-thienylmethyl)carbamate; methyl (6S,10S)-10-(1,3-benzodioxol-5-yl)-2-(4-bromobenzyl)-6-butyl-3,8-dioxo-1-(2-thienyl)-4-oxa-2,7,9-triazadodecan-12-oate; methyl (6S,10S)-2-(4-azidoobenzyl)-10-(1,3-benzodioxol-5-yl)-6-butyl-3,8-dioxo-1-(2-thienyl)-4-oxa-2,7,9-triazadodecan-12-oate; (2S)-2-[(tert-butoxycarbonyl)amino]hexyl phenyl(2-thienylmethyl)carbamate; methyl (6S,10S)-10-(1,3-benzodioxol-5-yl)-6-butyl-3,8-dioxo-2-phenyl-1-(2-thienyl)-4-oxa-2,7,9-triazadodecan-12-oate; tert-butyl [(2S)-1-{[bis(3-thienylmethyl)carbamoyl]oxy}hexan-2-yl]carbamate; methyl (6S,10S)-10-(1,3-benzodioxol-5-yl)-6-butyl-3,8-dioxo-1-(3-thienyl)-2-(3-thienylmethyl)-4-oxa-2,7,9-triazadodecan-12-oate; benzyl [(5S)-5-[(tert-butoxycarbonyl)amino]-6-{[butyl(2-thienylmethyl)carbamoyl]oxy}hexyl]carbamate; (2S)-2-[(tert-butoxycarbonyl)amino]hexyl butyl(2-thienylmethyl)carbamate; methyl (3S,7S)-3-(1,3-benzodioxol-5-yl)-7-butyl-5,10-dioxo-11-(2-thienylmethyl)-9-oxa-4,6,11-triazapentadecan-1-oate; benzyl [(5S)-5-[(tert-butoxycarbonyl)amino]-6-{[(2-methoxyethyl)(2-thienylmethyl)carbamoyl]oxy}hexyl]carbamate; (2S)-2-[(tert-butoxycarbonyl)amino]hexyl (2-methoxyethyl)(2-thienylmethyl)carbamate; methyl (9S,13S)-13-(1,3-benzodioxol-5-yl)-9-butyl-6,11-dioxo-5-(2-thienylmethyl)-2,7-dioxa-5,10,12-triazapentadecan-15-oate; (2S)-2-[({3-[(methylsulfonyl)amino]benzyl}carbamoyl)amino]hexyl (2-methoxyethyl)(2-thienylmethyl)carbamate; (2S)-2-{[(4-bromobenzyl)carbamoyl]amino}hexyl bis(2-thienylmethyl)carbamate; (2S)-2-{[(4-azidobenzyl)carbamoyl]amino}hexyl bis(2-thienylmethyl)carbamate; tert-butyl [(2S)-1-{[bis(2-thienylmethyl)carbamoyl]thio}hexan-2-yl]carbamate; and methyl (6S,10S)-10-(1,3-benzodioxol-5-yl)-6-butyl-3,8-dioxo-1-(2-thienyl)-2-(2-thienylmethyl)-4-thia-2,7,9-triazadodecan-12-oate.

\* \* \* \* \*